US012746224B2

(12) United States Patent
Quitterer et al.

(10) Patent No.: US 12,746,224 B2
(45) **Date of Patent: *Sep. 29, 2026**

(54) COMPOUNDS FOR TREATING CNS- AND NEURODEGENERATIVE DISEASES

(71) Applicant: ETH ZURICH, Zurich (CH)

(72) Inventors: Ursula Quitterer, Zurich (CH); Said Abdalla, Mainz (DE)

(73) Assignee: ETH ZURICH, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/040,011

(22) PCT Filed: Mar. 15, 2019

(86) PCT No.: PCT/EP2019/056565

§ 371 (c)(1), (2) Date: Sep. 21, 2020

(87) PCT Pub. No.: WO2019/179890

PCT Pub. Date: Sep. 26, 2019

(65) Prior Publication Data

US 2021/0015793 A1 Jan. 21, 2021

(30) Foreign Application Priority Data

Mar. 19, 2018 (EP) .................................... 18162579

(51) Int. Cl.

*A61K 31/4025* (2006.01)
*A61K 31/506* (2006.01)
*A61P 25/24* (2006.01)
*A61P 25/28* (2006.01)

(52) U.S. Cl.

CPC ........ *A61K 31/4025* (2013.01); *A61K 31/506* (2013.01); *A61P 25/24* (2018.01); *A61P 25/28* (2018.01)

(58) Field of Classification Search

CPC ... A61K 31/4025; A61K 31/506; A61P 25/24; A61P 25/28; A61P 25/00; C07D 417/12; C07D 405/06; C07D 403/04; C07D 405/04; C07D 405/12

See application file for complete search history.

(56) References Cited

U.S. PATENT DOCUMENTS

| | | | | |
|---|---|---|---|---|
| 5,591,762 | A | 1/1997 | Hauel et al. | |
| 5,840,746 | A | 11/1998 | Ducharme et al. | |
| 2005/0119329 | A1* | 6/2005 | Godel | A61P 25/28 548/530 |
| 2005/0234095 | A1 | 10/2005 | Xie et al. | |
| 2006/0223812 | A1 | 10/2006 | Mandelkow et al. | |
| 2009/0269301 | A1* | 10/2009 | Thormann | A61P 25/24 514/397 |
| 2011/0224254 | A1* | 9/2011 | Heiser | C07D 401/14 546/199 |
| 2012/0237475 | A1 | 9/2012 | Heiser et al. | |
| 2015/0335671 | A1 | 11/2015 | Gavathiotis et al. | |

FOREIGN PATENT DOCUMENTS

| | | | | |
|---|---|---|---|---|
| IE | 20070466 | * | 3/2009 | A61K 31/352 |
| WO | WO 2002/030892 | A1 | 4/2002 | |
| WO | WO 2005123688 | A2 | 12/2005 | |
| WO | WO 2008/055945 | A1 | 5/2008 | |
| WO | WO 2008/116092 | A1 | 9/2008 | |
| WO | WO 2010/081783 | A1 | 7/2010 | |
| WO | WO 2010137350 | A1 | 12/2010 | |
| WO | WO 2012080727 | A2 | 6/2012 | |
| WO | WO 2014/025942 | A1 | 2/2014 | |
| WO | WO 2018/002437 | A1 | 1/2018 | |
| WO | WO 2018/130537 | A1 | 7/2018 | |

OTHER PUBLICATIONS

Waldschmidt et al. (Bioorganic & Medicinal Chemistry Letters 28 (2018) p. 1507-1515, S1-25).*
Kubinyi (3D QSAR in Drug Design: Ligand-Protein Interactions and Molecular Similarity, vol. 2-3, Springer, 1998, 800 pages) p. 243-44 provided.*
Wermuth, The Practice of Medicinal Chemsitry, 2d ed. (2003), 768 pages. Chs. 9-10 provided.*
Larbig et al. (J. Comb. Chem. 2006, 8, 480-490).*
Korczyn et al. Journal of Alzheimer's Disease, vol. 29, Issue 2 Mar. 20, 2012 (abstract).*
Mayo Clinic Alzheimer's disease wayback machine 2017.*
Waldschmidt et al. (Bioorganic & Medicinal Chemistry Letters 28 (2018) p. 1507-1515, S1-25) (Year: 2018).*
Kubinyi (3D QSAR in Drug Design: Ligand-Protein Interactions and Molecular Similarity, vol. 2-3, Springer, 1998, 800 pages) p. 243-44 provided. (Year: 1998).*
Wermuth, The Practice of Medicinal Chemsitry, 2d ed. (2003), 768 pages. Chs. 9-10 provided. (Year: 2003).*
McGonigle et al., Biochemical Pharmacology 87 (2014), 162-171. https://doi.org/10.1016/j.bcp.2013.08.006 (Year: 2014).*
Korczyn et al. Journal of Alzheimer's Disease, vol. 29, Issue 2 Mar. 20, 2012 (abstract). (Year: 2012).*
Mayo Clinic Alzheimer's disease wayback machine 2017. (Year: 2017).*
Sparks et al. (2018). What do you know about Parkinson's disease? https://newsnetwork.mayoclinic.org/discussion/what-do-you-know-about-parkinsons-disease/ (Year: 2018).*
Larbig et al. J. Comb. Chem. 2006, 8, 480-490. (Year: 2006).*

(Continued)

*Primary Examiner* — James H Alstrum-Acevedo
*Assistant Examiner* — Chantal Adlam
(74) *Attorney, Agent, or Firm* — Bryan D. Zerhusen, Esq.; Nicholas R. Herrel, Esq.; CANTOR COLBURN LLP

(57) ABSTRACT

The present invention is directed to compounds and corresponding pharmaceutical formulations for use in the medical treatment of CNS- and neurodegenerative diseases, for example, for use in the treatment and prophylaxis of familial or sporadic Alzheimer's disease. The invention further relates to corresponding methods of treatment and to a method for determining treatment progression or outcome of senescence and anti-aging treatment based on the detection and/or quantification of Membrane Palmitoylated Protein 1 (MPP1).

8 Claims, 19 Drawing Sheets

Figure 1:
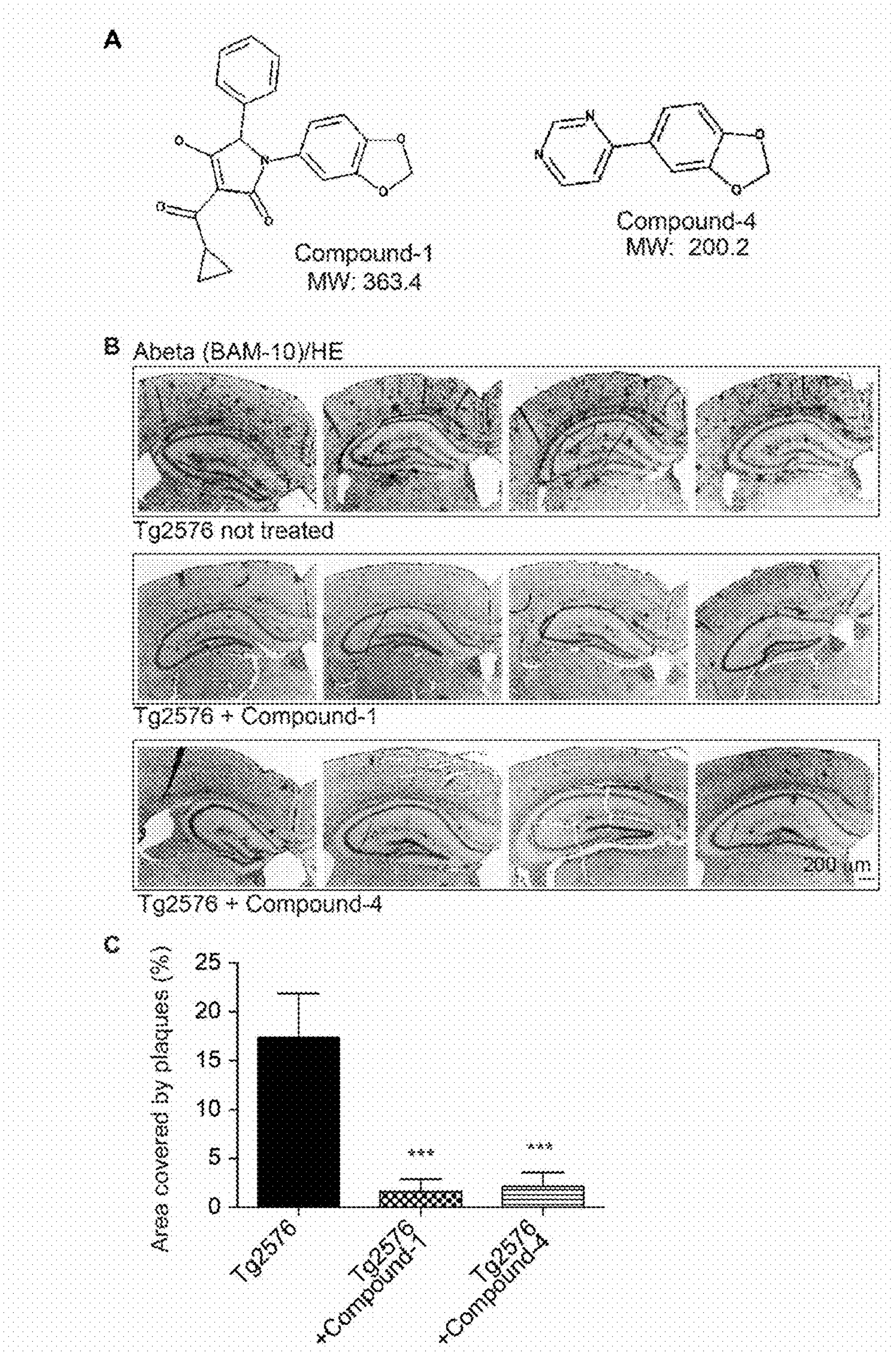

Specification includes a Sequence Listing.

(56) References Cited

OTHER PUBLICATIONS

Guccione, Manuela, et al., G-Protein-Coupled Receptor Kinase 2 (GRK2) Inhibitors: Current Trends and Future Perspectives, Journal of Medicinal Chemistry, vol. 59, No. 10, Jul. 8, 2016.
Starosyla, S. A. et al. "Identification of apoptosis signal-regulating kinase 1 (ASK1) inhibitors among the derivatives of benzothiazole-2yl-3-hydroxy-5-phenyl-1,5-dihydro-pyrrol-2-one", Bioorganic & medicinal Chemistry, 2015, 23, 2489-2497.
Zheng, Y. et al. "Structure of CC chemokine receptor 2 with orthosteric and allosteric antagonists", Nature, 2016, 540, 458-461.
International Search Report and Written Opinion for PCT/EP2019/056565, dated Aug. 12, 2019.
Potashkin, Judith A., et al., Biosignatures for Parkingson's Diseae and Atypical Parkinsonian Disorders Patients, PLOS One, vol. 7, No. 8, Aug. 27, 2012.
Damont, A., et al., Hydrogen/deuterium exchange mass spectrometry in the world of small molecules, Nov. 19, 2021, Mass Spec Rev. 2021, e21765, pp. 1-32.
Documentation Compounds, Jun. 21, 2018, UTH 4454.
Schilling S, et al., Glutaminyl cyclase inhibition attenuates pyroglutamate Abeta and Alzheimer's disease-like pathology. Nat Med. Oct. 2008;14(10):1106-11. doi: 10.1038/nm.1872. Epub Sep. 28, 2008. PMID: 18836460.
Shin-ichi Kawano, et al., Analysis of keto-enol tautomers of curcumin by liquid chromatography/mass spectrometry, Chinese Chemical Letters, vol. 24, Issue 8, Jun. 2013,pp. 685-687,ISSN 1001-8417, https://doi.org/10.1016/j.cclet.2013.05.006.
Traven, V., et al.,—Keto-Enol Tautomerism, NMR Spectra, and HD Exchange of 4-Hydroxycoumarins, Can. J. Chem. 75: pp. 377-385, Jan. 1997.
Xu C, Wang YN, Wu H. Glutaminyl Cyclase, Diseases, and Development of Glutaminyl Cyclase Inhibitors. J Med Chem. May 27, 2021;64(10):6549-6565. doi: 10.1021/acs.jmedchem.1c00325. Epub May 17, 2021. PMID: 34000808.
Wilson RS, Leurgans SE, Boyle PA, Schneider JA, Bennett DA. Neurodegenerative basis of age-related cognitive decline. Neurology. Sep. 21, 2010;75(12):1070-8. doi: 10.1212/WVNL.0b013e3181f39adc. (EX 59).
Wszołek ZK, Słowiński J, Golan M, Dickson DW. Frontotemporal dementia and parkinsonism linked to chromosome 17. Folia Neuropathol. 2005;43(4):258-70. (EX 43).
Xie B, Shi X, et al., Y. Association between atherosclerosis and Alzheimer's disease: A systematic review and meta-analysis. Brain Behav. Apr. 2020;10(4):e01601. doi: 10.1002/brb3.1601. (EX 68).
Zeng XS, Geng WS, Jia JJ, Chen L, Zhang PP. Cellular and Molecular Basis of Neurodegeneration in Parkinson Disease. Front Aging Neurosci. Apr. 17, 2018;10:109. doi: 10.3389/fnagi.2018.00109. (EX 42).
Zhu C, Aguzzi A. Prion protein and prion disease at a glance. J Cell Sci. Sep. 1, 2021;134(17):jcs245605. doi: 10.1242/jcs.245605. (EX 53).
Wingo TS, et al., Shared mechanisms across the major psychiatric and neurodegenerative diseases. Nat Commun. Jul. 26, 2022;13(1):4314. doi: 10.1038/s41467-022-31873-5. (EX 4).
Wentz E., et al., Thirty years after anorexia nervosa onset, serum neurofilament light chain protein concentration indicates neuronal injury, European Child & Adolescent Psychiatry Jan. 2021) 30:1907-1915 (EX 15).
Bano D, Zanetti F, et al., Neurodegenerative processes in Huntington's disease. Cell Death Dis. Nov. 10, 2011;2(11): e228. doi: 10.1038/cddis.2011.112. (EX 50).
Becker S, et al,, Risk of neurodegenerative disease or dementia in adults with attention-deficit/hyperactivity disorder: a systematic review. Front Psychiatry. Aug. 17, 2023;14:1158546. doi: 10.3389/fpsyt.2023.1158546 (EX 73).
Beehuspoteea N, , et al, Exploring the relationship between ADHD and dementia. Progress in Neurology and Psychiatry, vol. 27. Iss. 2 2023, 5-9. https://doi.org/10.1002/pnp.784. (EX 74).
Brodtmann A, , et al, Neurodegeneration Over 3 Years Following Ischaemic Stroke: Findings From the Cognition and Neocortical Volume After Stroke Study. Front Neurol. Oct. 22, 2021;12:754204. doi: 10.3389/fneur.2021.754204. (EX 27).
Burtscher J, et al., The Muscle-Brain Axis and Neurodegenerative Diseases: The Key Role of Mitochondria in Exercise-Induced Neuroprotection. Int J Mol Sci. Jun. 17, 2021;22(12):6479. doi: 10.3390/ijms22126479. (EX 22).
Colín-Castelán D, et al., Associations between atherosclerosis and neurological diseases, beyond ischemia-induced cerebral damage. Rev Endocr Metab Disord. Mar. 2019;20(1):15-25. doi: 10.1007/s11154-019-09486-z. (EX 69).
Dickson DW. Pick's disease: a modern approach. Brain Pathol. Apr. 1998;8(2):339-54. doi: 10.1111/j.1750-3639.1998. tb00158.x. (EX 49).
Djafar JV, et al., Childhood Dementia: A Collective Clinical Approach to Advance Therapeutic Development and Care. Pediatr Neurol. Feb. 2023;139:76-85. doi: 10.1016/j.pediatrneurol.2022.11.015. (EX 75).
Dodd, W.S., et al., Traumatic Brain Injury and Secondary Neurodegenerative Disease, Traumatic Care 2022, pp. 511-522, Sep. 26, 2022 (EX 24).
Duman RS. Neuronal damage and protection in the pathophysiology and treatment of psychiatric illness: stress and depression. Dialogues Clin Neurosci. 2009;11(3):239-55. doi: 10.31887/DCNS.2009.11.3/rsduman. (EX 19).
Feldman EL, et al., Diabetic neuropathy. Nat Rev Dis Primers. Jun. 13, 2019;5(1):42. doi: 10.1038/s41572-019-0097-9. (EX 57).
Guo C, et al., Substance abuse and neurodegenerative diseases: focus on ferroptosis. Arch Toxicol. Jun. 2023;97 (6):1519-1528. doi: 10.1007/s00204-023-03505-4. (EX 17).
Guo H, et al., Neurobiological Links between Stress, Brain Injury, and Disease. Oxid Med Cell Longev. May 25, 2022;2022:8111022. doi: 10.1155/2022/8111022. (EX 71).
Hampel H, et al., The Amyloid-β Pathway in Alzheimer's Disease. Mol Psychiatry. Oct. 2021;26(10):5481-5503. doi: 10.1038/s41380-021-01249-0. (EX 10).
Hobday A L, Parmar M S (Sep. 28, 2021) The Link Between Diabetes Mellitus and Tau Hyperphosphorylation: Implications for Risk of Alzheimer's Disease. Cureus 13(9): e18362. DOI 10.7759/cureus.18362 (EX 56).
Iadecola C. Atherosclerosis and neurodegeneration: unexpected conspirators in Alzheimer's dementia. Arterioscler Thromb Vasc Biol. Nov. 1, 2003;23(11):1951-3. doi: 10.1161/01.ATV.0000102660.99744.85. (EX 29).
Iadecola C. The overlap between neurodegenerative and vascular factors in the pathogenesis of dementia. Acta Neuropathol. Sep. 2010;120(3):287-96. doi: 10.1007/s00401-010-0718-6. (EX 40).
Ichikawa-Escamilla E, et al., Progressive Supranuclear Palsy Syndrome: An Overview. IBRO Neurosci Rep. May 6, 2024;16:598-608. doi: 10.1016/j.ibneur.2024.04.008. (EX 47).
Jongsiriyanyong S, et al., Mild Cognitive Impairment in Clinical Practice: A Review Article. Am J Alzheimers Dis Other Demen. Dec. 2018;33(8):500-507. doi: 10.1177/1533317518791401. (EX 66).
Keon M, et al., Destination Amyotrophic Lateral Sclerosis. Front Neurol. Mar. 29, 2021;12:596006. doi: 10.3389/fneur.2021.596006. (EX 37).
Kim SE, et al., Interaction between Alzheimer's Disease and Cerebral Small Vessel Disease: A Review Focused on Neuroimaging Markers. Int J Mol Sci. Sep. 10, 2022;23(18):10490. doi: 10.3390/ijms231810490. (EX 41).
Kovacs GG, et al., .Tau pathology in Creutzfeldt-Jakob disease revisited. Brain Pathol. May 2017;27(3):332-344. doi: 10.1111/bpa.12411. (EX 52).
Lendahl U, et al., . Emerging links between cerebrovascular and neurodegenerative diseases—a special role for pericytes. EMBO Rep. Nov. 5, 2019;20(11):e48070. doi: 10.15252/embr.201948070. (EX 25).
Ling H, et al., Astrogliopathy predominates the earliest stage of corticobasal degeneration pathology. Brain. Dec. 2016;139(Pt 12):3237-3252. doi: 10.1093/brain/aww256. (EX 48).

(56) References Cited

OTHER PUBLICATIONS

Liu G, Shen C, Qiu A. Amyloid-β accumulation in relation to functional connectivity in aging: A longitudinal study. Neuroimage. Jul. 15, 2023;275:120146. doi: 10.1016/j.neuroimage.2023.120146. (EX 60).
Martins IJ, et al., . Molecular Insights into Appetite Control and Neuroendocrine Disease as Risk Factors for Chronic Diseases in Western Countries. Open Journal of Endocrine and Metabolic Diseases, 2013, 3, 11-33. http://dx.doi.ogr/10.4236/ojemd.2013.35A002. (EX 61).
McEwen BS. The neurobiology of stress: from serendipity to clinical relevance. Brain Res. Dec. 15, 2000;886 (1-2):172-189. doi: 10.1016/s0006-8993(00)02950-4. (EX 72).
Mendelsohn AR, et al., . The Danger of Being Too Sympathetic: Norepinephrine in Alzheimer's Disease and Graying of Hair. Rejuvenation Res. Feb. 2020;23(1):68-72. doi: 10.1089/rej.2020.2309. (EX 62).
Mirab SM, et ak,m A Sexual and Reproductive Problems Associated with Neurodegenerative Disorders: A Narrative Review (EX 63).
Napoli C, Palinski W. Neurodegenerative diseases: insights into pathogenic mechanisms from atherosclerosis. Neurobiol Aging. Mar. 2005;26(3):293-302. doi: 10.1016/j.neurobiolaging.2004.02.031. (EX 30).
Outeiro TF, et al., Dementia with Lewy bodies: an update and outlook. Mol Neurodegener. Jan. 21, 2019;14(1):5. doi: 10.1186/s13024-019-0306-8. (EX 46).
Pacholko A, Iadecola C. Hypertension, Neurodegeneration, and Cognitive Decline. Hypertension. May 2024;81 (5):991-1007. doi: 10.1161/HYPERTENSIONAHA.123.21356. (EX 28).
Paolini Paoletti et al., The Contribution of Small Vessel Disease to Neurodegeneration: Focus on Alzheimer's Disease, Parkinson's Disease and Multiple Sclerosis. Int J Mol Sci. May 7, 2021;22(9):4958. doi: 10.3390/ijms22094958. (EX 32).
Piccinni A, eta al., Neurodegeneration, β-amyloid and mood disorders: state of the art and future perspectives. Int J Geriatr Psychiatry. Jul. 2013;28(7):661-71. doi: 10.1002/gps.3879. (EX 11).
Power BD, Looi JC. The thalamus as a putative biomarker in neurodegenerative disorders. Aust N Z J Psychiatry. Jun. 2015;49(6):502-18. doi: 10.1177/0004867415585857. (EX 51).
Qiu Q, Chen J, Xu N, Zhou X, Ye C, Liu M, Liu Z. Effects of autonomic nervous system disorders on male infertility. Front Neurol. Oct. 23, 2023;14:1277795. doi: 10.3389/fneur.2023.1277795. (EX 65).
Rabin JS, et al., Cerebral amyloid angiopathy interacts with neuritic amyloid plaques to promote tau and cognitive decline. Brain. Aug. 27, 2022;145(8):2823-2833. doi: 10.1093/brain/awac178. (EX 31).
Radulovic J, Ivkovic S, Adzic M. From chronic stress and anxiety to neurodegeneration: Focus on neuromodulation of the axon initial segment. Handb Clin Neurol. 2022;184:481-495. doi: 10.1016/B978-0-12-819410-2.00025-4. (EX 12).
Risacher SL, Saykin AJ. Neuroimaging biomarkers of neurodegenerative diseases and dementia. Semin Neurol. Sep. 2013;33(4):386-416. doi: 10.1055/s-0033-1359312. (EX 2).
Roy ARK, Datta S, Hardy E, Sturm VE, Kramer JH, Seeley WW, Rankin KP, Rosen HJ, Miller BL, Perry DC. Behavioural subphenotypes and their anatomic correlates in neurodegenerative disease. Brain Commun. Feb. 27, 2023;5(2):fcad038. doi: 10.1093/braincomms/fcad038. (EX 14).
Rundek T, Tolea M, Ariko T, Fagerli EA, Camargo CJ. Vascular Cognitive Impairment (VCI). Neurotherapeutics. Jan. 2022;19(1):68-88. doi: 10.1007/s13311-021-01170-y. (EX 67).
Sandi D, et al. Neurodegeneration in Multiple Sclerosis: Symptoms of Silent Progression, Biomarkers and Neuroprotective Therapy-Kynurenines Are Important Players. Molecules. Jun. 5, 2021;26(11):3423. doi: 10.3390/molecules26113423. (EX 39).
Segobin S, Ambler M, Laniepce A, Platel H, Chételat G, Groussard M, Pitel AL. Korsakoff's Syndrome and Alzheimer's Disease-Commonalities and Specificities of Volumetric Brain Alterations within Papez Circuit. J Clin Med. Apr. 27, 2023;12(9):3147. doi: 10.3390/jcm12093147. (EX 45).
Shaw PJ. Molecular and cellular pathways of neurodegeneration in motor neurone disease. J Neurol Neurosurg Psychiatry. Aug. 2005;76(8):1046-57. doi: 10.1136/jnnp.2004.048652. (EX 34).
Sobue G, Ishigaki S, Watanabe H. Pathogenesis of Frontotemporal Lobar Degeneration: Insights From Loss of Function Theory and Early Involvement of the Caudate Nucleus. Front Neurosci. Jul. 12, 2018;12:473. doi: 10.3389/fnins.2018.00473. (EX 44).
Stone WS, Phillips MR, Yang LH, Kegeles LS, Susser ES, Lieberman JA. Neurodegenerative model of schizophrenia: Growing evidence to support a revisit. Schizophr Res. May 2022;243:154-162. doi: 10.1016/j.schres.2022.03.004. (EX 3).
Sumien N, et at al., . Neurodegenerative Disease: Roles for Sex, Hormones, and Oxidative Stress. Endocrinology. Nov. 1, 2021;162(11):bqab185. doi: 10.1210/endocr/bqab185. (EX 64).
Turner V, Husain M. Anhedonia in Neurodegenerative Diseases. Curr Top Behav Neurosci. 2022;58:255-277. doi: 10.1007/7854_2022_352. (EX 21).
Wallace DR. HIV-associated neurotoxicity and cognitive decline: Therapeutic implications. Pharmacol Ther. Jun. 2022;234:108047. doi: 10.1016/j.pharmthera.2021.108047. (EX 55).
Wilson DM 3rd, Cookson MR, Van Den Bosch L, Zetterberg H, Holtzman DM, Dewachter I. Hallmarks of neurodegenerative diseases. Cell. Feb. 16, 2023;186(4):693-714. doi: 10.1016/j.cell.2022.12.032. (EX 1).
Hou, Y., et al., Ageing as a risk factor for neurodegenerative disease, Nature Reviews |Neurology| Oct. 2019 | vol. 15, pp. 565-581.
"Alzheimer's Disease", Alzheimer's Disease: Symptoms & Treatment, Cleveland Clinic, 2025, 19 pages, https://my.clevelandclinic.org/health/diseases/9164-alzheimers-disease 1 von.
Alla et al., "Identification of membrane palmitoylated protein 1 (MPP1) as a heart-failure-promoting protein triggered by cardiovascular risk factors and aging", Biochemical Pharmacology 217 (2023) 115789.
Balough et al., "Hallmarks of female reproductive aging inphysiologic aging mice", Nature Aging, vol. 4, Dec. 2024, 1711-1730.
Bellelli et al, "Hallmarks of aging and Alzheimer's Disease pathogenesis: Paving the route for new therapeutic targets", Elsevier, Ageing Research Reviews 106 (2025) 102699, 16 pages.
Kisling et al., "Prevention Strategies", StatPearls—NCBI Bookshelf, Aug. 1, 2023, 4 pages.
Pino et al., "The effects of aging on semen parameters and sperm DNA fragmentation" JBRA Assisted Reproduction 2020;24(1):82-86doi: 10.5935/1518-0557.20190058.
Sharma, S, et al., The chronic unpredictable mild stress (CUMS) Paradigm: Bridging the gap in depression research from bench to bedside, Brain Research 1843 (Jul. 2024) 149123.
Thal et al., "Paroxetine Is a Direct Inhibitor of G Protein-Coupled Receptor Kinase 2 and Increases Myocardial Contractility", ACS Chem. Biol. 2012, 7, 1830-1839.
Yang et al., "Depression, Depression Treatments, and Risk ofIncident Dementia: A Prospective Cohort Study of 354,313 Participants" Society of Biological Psychiatry. Biological Psychiatry May 1, 2023; 93:802-809.

* cited by examiner

A

Compound-1F
(C21H16FNO5; MW 381.36)
1-(1,3-Benzodioxol-5-yl)-4-(cyclopropanecarbonyl)-
-2-(4-fluorophenyl)-3-hydroxy-2H-pyrrol-5-one Compound-1F Human PBMN cells Healthy human research participants Healthy human research participants, repeated oral dosing of Compound-1F (60 mg/d)

```
                              SEQUENCE LISTING


<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: oligonucleotide primer MPP1-forward

<400> SEQUENCE: 1

cgcctttcat tgtgttcatt gcacctactg                                       30


<210> SEQ ID NO 2
<211> LENGTH: 18
<212> TYPE: DNA
<213> ORGANISM: Artificial Sequence
<220> FEATURE:
<223> OTHER INFORMATION: oligonucleotide primer Sp6-reverse

<400> SEQUENCE: 2

tagaaggcac agtcgagg                                                    18
```

COMPOUNDS FOR TREATING CNS- AND NEURODEGENERATIVE DISEASES

RELATED APPLICATIONS

This application is a National Stage of PCT/EP2019/056565, filed: 15 Mar. 2019, titled: COMPOUNDS FOR TREATING CNS-AND NEURODEGENERATIVE DISEASES, published as International Patent Application No. WO 2019/179890 A1, which claims the benefit and priority to European Patent Application No. 18162579.9, filed on 19 Mar. 2018, all of which are incorporated by reference in their entirety for all purposes.

INCORPORATION BY REFERENCE

In compliance with 37 C.F.R. § 1.52 (e) (5), the sequence information contained in electronic file name: 50669PCT_Sequence_Listing_ST25.txt; size 1 KB; created on: 14 Mar. 2019; using Patent-In 3.5 is hereby incorporated herein by reference in its entirety.

The present invention is directed to compounds and corresponding pharmaceutical formulations for use in the medical treatment of CNS- and neurodegenerative diseases, for example, for use in the treatment and prophylaxis of familial or sporadic Alzheimer's disease. The invention further relates to corresponding methods of treatment and to a method for determining treatment progression or outcome of senescence and anti-aging treatment based on the detection and/or quantification of Membrane Palmitoylated Protein 1 (MPP1).

Alzheimer's disease (AD), the most frequent form of dementia, is a protein aggregation-associated disease. Age is the best-established risk factor for AD, and with increasing life expectancy, the incidence of AD is increasing worldwide. Treatment options for AD are limited. Currently, there are only four different drugs approved for the treatment of AD: three different acetylcholinesterase inhibitors, which enhance the availability of the cognition-enhancing acetylcholine, and the NMDA receptor antagonist, memantine, (Kulshreshtha & Piplani, Neurol. Sci. 37, 1403-1435, 2016). All these drugs cannot halt disease progression and relief AD symptoms only for a short time period. Therefore, there is an urgent need for disease-modifying treatment approaches. A possible target is the aberrant protein aggregation process leading finally to Abeta (amyloid-beta) plaque formation and/or accumulation of insoluble Abeta peptides. However, approaches that only interfere with Abeta plaque formation and/or accumulation of insoluble Abeta peptides have not demonstrated efficacy in retarding AD progression, and even showed major side effects (Kulshreshtha & Piplani, 2016). The underlying reason could be the fact that the sole increase in Abeta aggregates does not cause substantial neuronal loss (AbdAlla et al., J. Biol. Chem. 284, 6554-6565, 2009; AbdAlla et al., J. Biol. Chem. 284, 6566-6574, 2009).

New approaches could possibly target Abeta-independent factors with neuropathological relevance in AD, e.g. Tau hyperphosphorylation, neurodegenerative AT2 receptor aggregation, the excessive generation of reactive oxygen species (ROS), inflammation and ACE-dependent angiotensin II AT1 receptor activation (Kulshreshtha & Piplani, 2016); AbdAlla et al., J. Biol. Chem. 284, 6554-6565 (2009); AbdAlla et al., J. Biol. Chem. 284, 6566-6574 (2009); AbdAlla et al., Int. J. Mol. Sci. 14, 16917-16942 (2013); AbdAlla et al., Biomed. Res. Int. 2015: 917156 (2015)). In addition, environmental factors such as chronic mild stress, which also play a major role in the progression of neurodegenerative symptoms, need to be considered (AbdAlla et al., J. Biol. Chem. 284, 6554-6565 (2009); AbdAlla et al., J. Biol. Chem. 284, 6566-6574 (2009); Briones et al., Br. J. Pharmacol. 165, 897-907 (2012); AbdAlla et al., Biomed. Res. Int. 2015:917156 (2015)).

Mitochondrial dysfunction and mitochondrial damage has been identified as common factor underlying all major neurodegenerative and ageing-induced pathomechanisms (Valero T, Curr. Pharm. Des. 20, 5507-5509 (2014); Onyango et al., Aging Dis 7, 201-214 (2016); Onyango, Neural Regen Res. 13, 19-25 (2018); Jeong S. Mol. Cells 40, 613-620 (2017)). But to date, there are no successful approaches, which can treat mitochondrial dysfunction (Frozza et al., Front. Neurosci. 12:37 (2018)).

The problem underlying the present invention is the identification and provision of new compounds for use in the medical treatment of CNS- (central nervous system) and neurodegenerative diseases such as, for example, but not limited to dementia-associated CNS- and neurodegenerative disorders, preferably CNS- and neurodegenerative disease-associated schizophrenia with dementia, psychiatric disorders (e.g. Alzheimer's disease, schizophrenia, mood and anxiety disorders) and behavioral disorders (e.g. anorexia nervosa and substance use disorder), depression-associated CNS- and neurodegenerative disorders, preferably depression and depression-related symptoms, preferably anhedonia and anorexia, and muscle wasting, brain injury, preferably traumatic brain injury, cerebrovascular disease-induced neurodegeneration (i.e. ischemic stroke-induced neurodegeneration, hypertension-induced neurodegeneration, atherosclerosis-induced neurodegeneration, amyloid angiopathy-induced neurodegeneration), and preferably small-vessel cerebrovascular disease, motor neuron disease, ALS (amyotrophic lateral sclerosis), multiple sclerosis, familial and sporadic forms of Alzheimer's Disease, vascular dementia, Morbus Parkinson, chromosome-17-linked Morbus Parkinson, frontotemporal dementia, Korsakoff's psychosis, Lewy Body diseases, progressive supranuclear palsy, corticobasal degeneration, Pick's disease, Huntington's disease, thalamic degeneration, prion-associated diseases, preferably Creutzfeld-Jacob disease, HIV-associated dementia, diabetes-induced neuropathy, neurodegenerative symptoms of ageing, preferably loss of appetite or greying of hair, and the decline of male and female fertility, cognitive-related disorders, mild cognitive impairment, age-associated memory impairment, age-associated cognitive decline, vascular cognitive impairment, central and peripheral neuronal symptoms of atherosclerosis and ischemia, stress-related CNS- and neurodegenerative disorders, attention deficit disorders, attention deficit hyperactivity disorders, memory disturbances in children, and progeria infantilis.

In a first aspect, the problem underlying the present invention is solved by a compound according to Formula (I) or (II):

Formula (I)

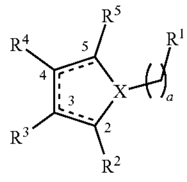

-continued

Formula (II)

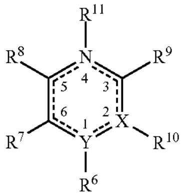

wherein:

the dotted lines between positions (2), (3), (4) and (5) in Formula (I) and between positions (1), (2), (3), (4), (5) and (6) in Formula (II) represent single bonds or double bonds between the respective positions;

X is selected from the group consisting of N and C;

Y is selected from the group consisting of S and C, with the proviso that when Y is C, X is N;

a is an integer between 0 and 15, preferably between 0 and 10, more preferably between 0 and 5, most preferably is 0 or 1;

$R^1$ is selected from the group consisting of (i) hydrogen, hydroxyl, F, C, Br and oxo, preferably if X is not N or if X is N and a is not 0, $R^1$ is selected from the group consisting of hydroxyl, F, Cl, Br and oxo;

(ii) linear or branched, substituted or non-substituted $(C_{1-10})$alkyl ether, $(C_{2-10})$alkenyl ether, $(C_{2-10})$alkynyl ether and $(C_{4-10})$carbocyclic ether;

(iii) linear or branched, substituted or non-substituted $(C_{1-10})$alkyl, preferably $(C_{1-5})$alkyl, more preferably methyl, ethyl and propyl, most preferably methyl, $(C_{2-10})$alkenyl and $(C_{2-10})$alkynyl;

(iv) substituted or non-substituted carbocycle selected from the group consisting of $(C_{3-10})$carbocycle, preferably $(C_3)$carbocycle and $(C_{5-6})$carbocycle, preferably aromatic $(C_6)$carbocycle, more preferably a non-substituted phenyl and a para-substituted phenyl that is substituted by a substituent selected from the group consisting of C, F, Br, substituted or non-substituted methyl, preferably —$(CF_3)$, ethyl, propyl and cyclopropyl; and (v) substituted or non-substituted $(C_{3-6})$heterocycle and $(C_7\text{-}C_{10})$carbo- or heterobicycle having 1 to 3 heteroatoms each independently selected from N, O and S, preferably substituted or non-substituted $(C_7)$heterobicycle having 2 heteroatoms selected from N and S, more preferably substituted or non-substituted indazolyl, benzimidazolyl and benzodioxolyl, preferably indazolyl, benzimidazolyl and benzodioxolyl connected via position (5) or (6), more preferably via position (6) of the indazolyl or benzodioxolyl or position (5) of the benzimidazolyl;

$R^2$ is selected from the group consisting of (i) hydrogen, hydroxyl, O—$R^{14}$, —O—C(=O)—$R^{14}$, F, C, Br and oxo wherein $R^{14}$ is selected from the group consisting of (aa) linear or branched, substituted or non-substituted $(C_{1-10})$alkyl, preferably $(C_{1-5})$alkyl, more preferably methyl, ethyl and propyl, most preferably methyl, $(C_{2-10})$alkenyl, and $(C_2\ )$alkynyl;

(bb) substituted or non-substituted aromatic or non-aromatic $(C_{3-10})$carbocycle, preferably $(C_{3-6})$cycloalkyl, more preferably $(C_3)$carbocycle and $(C_6)$ carbocycle, preferably $(C_6)$carbocycle, more preferably phenyl that is mono-substituted in para position by $(C_3)$carbocycle or —$(CF_3)$ or di-substituted in meta position by $(C_3)$carbocycle or —$(CF_3)$; and (cc) substituted or non-substituted aromatic or non-aromatic, preferably aromatic, $(C_{3-6})$heterocycle having 1 to 3 heteroatoms each independently selected from N, O and S;

(ii) linear or branched, substituted or non-substituted $(C_{1-10})$alkyl, preferably $(C_{1-5})$alkyl, more preferably methyl, ethyl and propyl, most preferably methyl, $(C_2\ )$alkenyl, $(C_{2-10})$alkynyl, and $(C_{3-10})$carbocycle, preferably $(C_{3-6})$cycloalkyl;

(iii) linear or branched, substituted or non-substituted $(C_{1-10})$alkyl ether, $(C_{2-10})$alkenyl ether, $(C_{2-10})$alkynyl ether and $(C_{4-10})$carbocyclic ether; and (iv) substituted or non-substituted $(C_{3-6})$heterocycle and $(C_7\text{-}C_{10})$carbo- or heterobicycle having 1 to 3 heteroatoms each independently selected from N, O and S, preferably substituted or non-substituted $(C_7)$ heterobicycle having 2 heteroatoms selected from N and S, more preferably substituted or non-substituted indazolyl, benzimidazolyl and benzodioxolyl, preferably indazolyl, benzimidazolyl and benzodioxolyl connected via position (5) or (6) of the indazolyl, benzodioxolyl or benzimidazolyl;

$R^3$ and $R^4$ are independently selected from the group consisting of (i) hydrogen, —O—$R^{14}$, —O—C(=O)—$R^{14}$, F, C, Br and oxo, wherein $R^{14}$ is selected from the group consisting of (aa) linear or branched, substituted or non-substituted $(C_{1-10})$alkyl, preferably $(C_{1-5})$alkyl, more preferably methyl, ethyl and propyl, most preferably methyl, $(C_{2-10})$alkenyl, and $(C_2\ )$alkynyl;

(bb) substituted or non-substituted aromatic or non-aromatic $(C_{3-10})$carbocycle, preferably $(C_{3-6})$cycloalkyl, more preferably $(C_3)$carbocycle and $(C_6)$ carbocycle, preferably $(C_6)$carbocycle, more preferably phenyl that is mono-substituted in para position by $(C_3)$carbocycle or —$(CF_3)$ or di-substituted in meta position by $(C_3)$carbocycle or —$(CF_3)$; and (cc) substituted or non-substituted aromatic or non-aromatic, preferably aromatic, $(C_{3-6})$heterocycle having 1 to 3 heteroatoms each independently selected from N, O and S;

(ii) linear or branched, substituted or non-substituted $(C_{1-10})$alkyl, preferably $(C_{1-5})$alkyl, more preferably methyl, ethyl and propyl, most preferably methyl, $(C_2\ )$alkenyl, $(C_{2-10})$alkynyl and $(C_{3-10})$carbocycle, preferably substituted or non-substituted $(C_{3-6})$cycloalkyl and $(C_{3-6})$heterocycle having 1 to 3 heteroatoms each independently selected from N, O and S;

(iii) linear or branched, substituted or non-substituted $(C_{1-10})$alkyl ether, $(C_{2-10})$alkenyl ether, $(C_{2-10})$alkynyl ether and $(C_{4-10})$carbocyclic ether;

(iv)

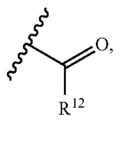

wherein $R^{12}$ is selected from the group consisting of (aa) hydrogen, hydroxyl, substituted or non-substituted N, F, Cl and Br;

(bb) linear or branched, substituted or non-substituted $(C_{1-10})$alkyl, preferably $(C_{1-5})$alkyl, more preferably methyl, ethyl and propyl, most preferably methyl, $(C_{2-10})$alkenyl, and $(C_{2}\ )$alkynyl;

(cc) substituted or non-substituted aromatic or non-aromatic $(C_{3-10})$carbocycle, preferably $(C_{3-6})$cycloalkyl, more preferably $(C_3)$carbocycle and $(C_6)$ carbocycle, preferably $(C_6)$carbocycle, more preferably phenyl that is mono-substituted in para position by $(C_3)$carbocycle or —$(CF_3)$ or di-substituted in meta position by $(C_3)$carbocycle or —$(CF_3)$; and (dd) substituted or non-substituted aromatic or non-aromatic, preferably aromatic, $(C_{3-6})$heterocycle having 1 to 3 heteroatoms each independently selected from N, O and S; and (v)

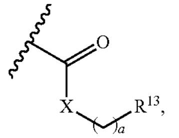

wherein X is N or C, a is an integer between 0 and 15, preferably between 0 and 10, more preferably between 0 and 5, most preferably is 0 or 1, and $R^{13}$ is selected from the group consisting of (aa) hydrogen, hydroxyl, F, Cl and Br;

(bb) linear or branched, substituted or non-substituted $(C_{1-10})$alkyl, preferably $(C_{1-5})$alkyl, more preferably methyl, ethyl and propyl, most preferably methyl, $(C_{2-10})$alkenyl and $(C_{2}\ )$alkynyl;

(cc) substituted or non-substituted $(C_{3-10})$carbocycle, preferably $(C_{3-6})$cycloalkyl, $(C_7\text{-}C_{10})$carbo- or heterobicycle and $(C_{3-6})$heterocycle having 1 to 3 heteroatoms each independently selected from N, O and S.

more preferably, for $R^3$, $R^{13}$ is $(C_7)$heterobicycle having 2 heteroatoms selected from N and S, most preferably substituted or non-substituted indazolyl, benzimidazolyl and benzodioxolyl, preferably indazolyl, benzimidazolyl and benzodioxolyl connected via position (5) or (6), more preferably via position (5) of the indazolyl and benzodioxolyl or position (6) of the benzimidazolyl, and most preferably, for $R^4$, $R^{13}$ is substituted or non-substituted aromatic $(C_6)$carbocycle, preferably $(C_6)$carbocycle that is mono- or di-substituted in meta position by $(C_3)$-carbocycle or —$(CF_3)$, or mono-substituted in para position by $(C_3)$-carbocycle or —$(CF_3)$; and (dd) linear or branched, substituted or non-substituted $(C_{1-10})$alkyl ether, $(C_{2-10})$alkenyl ether, $(C_{2-10})$alkynyl ether and $(C_{4-10})$carbocyclic ether;

wherein, if positions (2), (3) and/or (4) of the ring of Formula (I) are $sp^3$-hybridized, $R^2$ and $R^4$ and/or $R^3$ and $R^4$ are preferably in cis or trans configuration to each other, more preferably in trans configuration, preferably, $R^2$ is (R)- or (S)-, $R^3$ is (R)- or (S)- and/or $R^4$ is (R)- or (S)-configured, more preferably, $R^2$ is (R)-, $R^3$ is (R)- and/or $R^4$ is (R)-configured, or $R^2$ is (S)-, $R^3$ is (S)- and/or $R^4$ is (S)-configured.

$R^5$ and $R^9$ are selected from the group consisting of (i) hydrogen, hydroxyl, F, Cl, Br and oxo, with the proviso that $R^9$ is not oxo if X is N and Y is C;

(ii) linear or branched, substituted or non-substituted $(C_{1-10})$alkyl ether, $(C_{2-10})$alkenyl ether, $(C_{2-10})$alkynyl ether and $(C_{4-10})$carbocyclic ether;

(iii) linear or branched, substituted or non-substituted $(C_{1-10})$alkyl, preferably $(C_{1-5})$alkyl, more preferably methyl, ethyl and propyl, most preferably methyl, $(C_{2-10})$alkenyl and $(C_{2-10})$alkynyl;

(iv) substituted or non-substituted $(C_{3-10})$carbocycle, preferably substituted or non-substituted $(C_3)$carbocycle, substituted or non-substituted aromatic $(C_6)$ carbocycle, more preferably cyclopenta-2,4-dien-1-yl and aromatic $(C_6)$carbocycle, most preferably phenyl that is non-substituted or substituted in para position by a substituent selected from the group consisting of Cl, F, Br, substituted or non-substituted methyl, preferably —$(CF_3)$, ethyl, propyl and cyclopropyl; and (v) $(C_{3-6})$heterocycle having 1 to 3 heteroatoms each independently selected from N, O and S, preferably substituted or non-substituted imidazolyl and pyrazolyl, more preferably imidazolyl and pyrazolyl connected via imidazolyl-/pyrazolyl-position-(1)-nitrogen to the rings of Formula (I);

wherein, if position (5) of the ring of Formula (I) is $sp^3$-hybridized, $R^5$ is preferably (S)- or (R)-configured, more preferably (R)-configured;

and wherein, if position (3) of the ring of Formula (II) is $sp^3$-hybridized, $R^9$ is preferably (S)- or (R)-configured, more preferably (S)-configured;

$R^6$ and $R^{11}$ are independently selected from the group consisting of (i) linear or branched, substituted or non-substituted $(C_{1-10})$alkyl ether, $(C_{2-10})$alkenyl ether, $(C_{2-10})$alkynyl ether and $(C_{4-10})$carbocyclic ether;

(ii) linear or branched, substituted or non-substituted $(C_{1-10})$alkyl, preferably $(C_{1-5})$alkyl, more preferably methyl, ethyl and propyl, most preferably methyl, $(C_{2-10})$alkenyl and $(C_{2-10})$alkynyl;

(iii) substituted or non-substituted carbocycle selected from the group consisting of $(C_{3-10})$carbocycle, preferably $(C_3)$carbocycle and $(C_{5-6})$carbocycle, more preferably aromatic $(C_6)$carbocycle, most preferably phenyl that is non-substituted or mono- or di-substituted in meta and para position by a substituent selected from the group consisting of C, F, Br, substituted or non-substituted methyl, ethyl, propyl and cyclopropyl; and (iv) substituted or non-substituted $(C_{3-6})$heterocycle and $(C_7\text{-}C_{10})$carbo- or heterobicycle having 1 to 3 heteroatoms each independently selected from N, O and S, preferably substituted or non-substituted $(C_7)$ heterobicycle having 2 heteroatoms selected from N and S, most preferably substituted or non-substituted indazolyl, benzimidazolyl and benzodioxolyl, preferably indazolyl, benzimidazolyl and benzodioxolyl connected via position (5) or (6), more preferably via position (6) of the indazolyl or benzodioxolyl or position (5) of the benzimidazolyl, wherein $R^6$ is not present if Y is S; and/or wherein $R^{11}$ is absent if the ring of Formula (II) has a double bond between positions (4) and (5) or between positions (3) and (4) of the ring of Formula (II), and with the proviso that $R^6$ is not 1,2,4-triazolyl if X is N, Y is C and the ring of Formula (II) is aromatic;

$R^7$ is selected from the group consisting of (i) hydrogen, hydroxyl, F, Cl, Br and oxo;

(ii) linear or branched, substituted or non-substituted $(C_{1-10})$alkyl, preferably $(C_{1-5})$alkyl, more preferably methyl, ethyl and propyl, most preferably methyl, $(C_{2}\ \ )$alkenyl, $(C_{2-10})$alkynyl and $(C_{3-10})$carbocycle, preferably $(C_{3-6})$cycloalkyl and $(C_{3-6})$heterocycle having 1 to 3 heteroatoms each independently selected from N, O and S;

(iii) linear or branched, substituted or non-substituted $(C_{1-10})$alkyl ether, $(C_{2-10})$alkenyl ether, $(C_{2-10})$alkynyl ether and $(C_{4-10})$carbocyclic ether; and (iv)

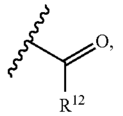

wherein $R^1$ is selected from the group consisting of (aa) hydrogen, hydroxyl, substituted or non-substituted N, F, Cl and Br;

(bb) linear or branched, substituted or non-substituted $(C_{1-10})$alkyl, preferably $(C_{1-5})$alkyl, more preferably methyl, ethyl and propyl, most preferably methyl, $(C_{2-10})$alkenyl, $(C_{2-10})$alkynyl and aromatic or non-aromatic $(C_{3-10})$carbocycle, preferably $(C_{3-6})$cycloalkyl, more preferably $(C_3)$carbocycle, most preferably aromatic $(C_6)$carbocycle that is mono-substituted in para position by $(C_3)$ carbocycle or —$(CF_3)$ or di-substituted in meta position by $(C_3)$carbocycle or —$(CF_3)$; and (cc) substituted or non-substituted, aromatic or non-aromatic, preferably aromatic, $(C_{3-6})$heterocycle having 1 to 3 heteroatoms each independently selected from N, O and S;

$R^8$ is selected from the group defined above for $R^7$, the group further comprising (i)

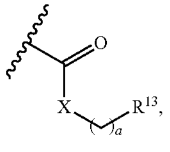

wherein X is N or C, a is an integer between 0 and 15, preferably between 0 and 10, more preferably between 0 and 5, most preferably is 0 or 1, and $R^3$ is selected from the group consisting of (aa) hydrogen, hydroxyl, F, Cl and Br;

(bb) linear or branched, substituted or non-substituted $(C_{1-10})$alkyl, preferably $(C_{1-5})$alkyl, more preferably methyl, ethyl and propyl, most preferably methyl, $(C_{2-10})$alkenyl and $(C_{2}\ \ )$alkynyl;

(cc) substituted or non-substituted $(C_{3-10})$carbocycle, preferably $(C_{3-6})$cycloalkyl, $(C_7\text{-}C_{10})$carbo- or heterobicycle and $(C_{3-6})$heterocycle having 1 to 3 heteroatoms each independently selected from N, O and S, more preferably substituted or non-substituted $(C_7)$heterobicycle having 2 heteroatoms selected from N and S, most preferably substituted or non-substituted indazolyl, benzimidazolyl and benzodioxolyl, preferably indazolyl and benzodioxolyl connected via position (5) or (6), more preferably via position (5) of the indazolyl and benzodioxolyl or position (6) of the benzimidazolyl, most preferably substituted or non-substituted aromatic $(C_6)$carbocycle, preferably $(C_6)$carbocycle that is mono- or di-substituted in meta position by $(C_3)$-carbocycle or —$(CF_3)$ or mono-substituted in para position by $(C_3)$-carbocycle or —$(CF_3)$; and (dd) linear or branched, substituted or non-substituted $(C_{1-10})$alkyl ether, $(C_{2-10})$alkenyl ether, $(C_{2-10})$alkynyl ether and $(C_{4-10})$carbocyclic ether;

with the proviso that $R^8$ is not 1,2,4-triazolyl if X is N, Y is C and the ring of Formula (II) is aromatic, and wherein, if position (5) of the ring of Formula (II) is $sp^3$-hybridized, $R^8$ is preferably (R)- or (S)-configured, more preferably (R)-configured;

$R^{10}$ is absent or selected from the group consisting of (i) hydrogen;

(ii) methyl; and (iii) cyclopropyl or phenyl that is mono-substituted in para position by a substituent selected from the group consisting of H, C, F, Br, methyl, —$(CF_3)$ and cyclopropyl;

wherein one or more of $R^2$, $R^3$, $R^4$, $R^5$, $R^6$, $R^7$, $R^8$, $R^9$, $R^{10}$ and $R^{11}$ are either directly attached to the rings of Formulas (I) or (II) or are attached to a linker between $R^2$, $R^3$, $R^4$, $R^5$, $R^6$, $R^7$, $R^8$, $R^9$, $R^{10}$ and/or $R^{11}$ and the rings of Formulas (I) or (II), wherein the linker is selected from the group consisting of linear or branched, substituted or non-substituted $(C_{1-10})$ alkyl ether, $(C_{2-10})$alkenyl ether, $(C_{2-10})$alkynyl ether, $(C_{4-10})$carbocyclic ether, linear or branched, substituted or non-substituted $(C_{1-10})$alkyl, $(C_{2}\ \ )$ alkenyl and $(C_{2}\ \ )$alkynyl;

and pharmaceutically acceptable salts or solvates thereof;

for use in the medical treatment of CNS- and neurodegenerative diseases.

It was found that the herein-defined compounds inhibit major neuropathological features of CNS- and neurodegenerative diseases and aging such as but not limited to AD, for example, (I) Abeta plaque formation, Tau hyperphosphorylation, neuronal degeneration and neuronal loss in Tg2576 AD mice as a model of familial AD (FAD), (II) Tau hyperphosphorylation and symptoms of depression in the chronic unpredictable mild stress (CUMS) model of sporadic AD, ageing and depression, (III) Tau hyperphosphorylation in the Tg-TauP301L transgenic model of tauopathy, and (IV) the aging-induced decline in male and female fertility.

For more detail, reference is made to the Examples and Figures further below.

The term medical treatment of CNS- and neurodegenerative diseases, as used herein, means prevention/prophylaxis and/or treatment of any disease, disorder or symptoms associated with a malfunction of the peripheral and/or central nervous system.

In a preferred embodiment, the compound for use in the present invention is a compound, wherein in Formula (I), a double bond is present between positions (3) and (4), or between positions (2) and (3) and between positions (4) and (5), or no double bond is present in the ring; and in Formula (II), no double bond is present in the ring or the ring is aromatic;

and/or a is 0 or 1; and/or $R^1$ is selected from the group consisting of (i) hydrogen;

(ii) linear or branched, substituted or non-substituted $(C_{1-5})$alkyl, more preferably methyl, ethyl and propyl, most preferably methyl;

(iii) substituted or non-substituted cyclopropyl and phenyl, preferably substituted phenyl, more preferably phenyl that is mono-substituted in para position by a substituent selected from the group consisting of H, C, F, Br, methyl, —$(CF_3)$ and cyclopropyl; and (iv) substituted or non-substituted, preferably mono-, di-, tri- or tetra-fluorinated indazolyl, benzimidazolyl and benzodioxolyl connected via position (5) or (6), preferably via position (6) of the indazolyl and benzodioxolyl or position (5) of the benzimidazolyl.

In a further preferred embodiment, the compound for use according to the present invention is a compound, wherein $R^2$ is selected from the group consisting of (i) hydrogen or oxo;

(ii) linear or branched, substituted or non-substituted $(C_{1-5})$alkyl, more preferably methyl, ethyl and propyl, most preferably methyl; and (iii) substituted or non-substituted indazolyl, benzimidazolyl and benzodioxolyl, preferably indazolyl, benzimidazolyl and benzodioxolyl connected via position (5) or (6) of the indazolyl, benzodioxolyl and benzimidazolyl; and/or $R^3$ is selected from the group consisting of (i) hydrogen;

(ii) linear or branched, substituted or non-substituted $(C_{1-5})$alkyl, more preferably methyl, ethyl and propyl, most preferably methyl;

(iii)

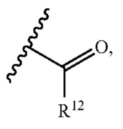

wherein $R^{12}$ is selected from the group consisting of (aa) N; and (bb) substituted or non-substituted, preferably substituted by F, cyclopropyl and phenyl, preferably phenyl that is mono-substituted in para position by cyclopropyl or —$(CF_3)$ or di-substituted in meta position by cyclopropyl or —$(CF_3)$ in each meta position; and (iv)

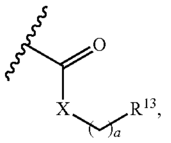

wherein X is N, a is 1 and $R^{13}$ is selected from the group consisting of substituted or non-substituted, preferably non-substituted indazolyl, benzimidazolyl and benzodioxolyl connected via position (6) or (5) of indazolyl, benzimidazolyl and benzodioxolyl, preferably via position (5) of the indazolyl and benzodioxolyl or position (6) of the benzimidazolyl;

and/or $R^4$ is selected from the group consisting of (i) hydrogen and hydroxyl;

(ii) linear or branched, substituted or non-substituted $(C_{1-5})$alkyl, more preferably methyl, ethyl and propyl, most preferably methyl;

(iii)

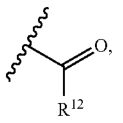

wherein $R^{12}$ is selected from the group consisting of (aa) N; and (bb) substituted or non-substituted cyclopropyl and phenyl, preferably phenyl that is mono-substituted in para or meta position by cyclopropyl or —$(CF_3)$, or di-substituted in meta position by cyclopropyl or —$(CF_3)$ in each meta position; and (iv)

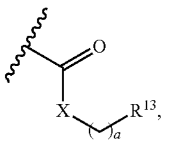

wherein X is N, a is 1 and $R^1$ is phenyl that is mono- or di-substituted in each meta position by cyclopropyl or —$(CF_3)$ or mono-substituted in para position by cyclopropyl or —$(CF_3)$;

wherein, if positions (2), (3) and/or (4) of the ring of Formula (I) are $sp^3$-hybridized $R^2$ and $R^4$ and/or $R^3$ and $R^4$ are preferably in cis or trans configuration to each other, more preferably in trans configuration, preferably, $R^2$ is (R)- or (S)-, $R^3$ is (R)- or (S)- and/or $R^4$ is (R)- or (S)-configured, more preferably, $R^2$ is (R)-, $R^3$ is (R)- and/or $R^4$ is (R)-configured, or $R^2$ is (S)-, $R^3$ is (S)- and/or $R^4$ is (S)-configured; and/or $R^5$ is selected from the group consisting of (i) hydrogen;

(ii) linear or branched, substituted or non-substituted $(C_5)$alkyl, more preferably methyl, ethyl and propyl, most preferably methyl;

(iii) substituted or non-substituted cyclopropyl and phenyl, preferably substituted phenyl, more preferably phenyl that is mono-, di-, tri- or tetrafluorinated, most preferably mono-substituted in para position by a substituent selected from the group consisting of H, Cl, F, Br, methyl, —($CF_3$) and cyclopropyl;

(iv) cyclopenta-2,4-dien-1-yl; and (v) substituted or non-substituted, preferably non-substituted imidazolyl and pyrazolyl connected via the imidazolyl-/pyrazolyl-position-(1)-nitrogen to the ring of Formula (I);

wherein, if position (5) of the ring of Formula (I) is $sp^3$-hybridized, $R^5$ is preferably (R)- or (S)-configured, more preferably (R)-configured; and/or $R^6$ and $R^{11}$ are independently selected from the group consisting of substituted or non-substituted, preferably mono-, di-, tri- or tetrafluorinated indazolyl, benzimidazolyl and benzodioxolyl connected via position (6) or (5), preferably via position (6) of the indazolyl and benzodioxolyl or position (5) of the benzimidazolyl;

wherein $R^6$ is not present if Y is S; and/or wherein $R^{11}$ is absent if the ring of Formula (II) has a double bond between positions (4) and (5) or between positions (3) and (4) of the ring of Formula (II); and/or $R^1$ and $R^8$ are independently selected from the group consisting of (i) hydrogen or fluorine;

(ii) linear or branched, substituted or non-substituted $(C_{1-5})$alkyl, more preferably methyl, ethyl and propyl, most preferably methyl; and (iii)

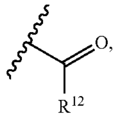

wherein $R^{12}$ is selected from the group consisting of (aa) N; and (bb) substituted or non-substituted cyclopropyl and phenyl, preferably phenyl that is mono-substituted in para position by cyclopropyl or —($CF_3$), or di-substituted in meta position by cyclopropyl or —($CF_3$) in each meta position;

wherein, for R, the group further comprises

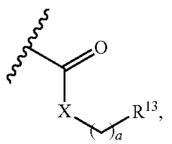

wherein X is N, a is 1 and $R^{12}$ is selected from the group consisting of substituted or non-substituted, preferably non-substituted indazolyl, benzimidazolyl and benzodioxolyl connected via position (6) or (5), preferably via position (5) of the indazolyl and benzodioxolyl or position (6) of the benzimidazolyl; and wherein, if position (5) of the ring of Formula (II) is $sp^3$-hybridized, $R^8$ is preferably (R)- or (S)-configured, more preferably (R)-configured; and/or $R^9$ is selected from the group consisting of (i) hydrogen, fluorine, methyl and cyclopropyl; and (ii) substituted or non-substituted phenyl, preferably phenyl that is substituted in para position by a substituent selected from the group consisting of H, Cl, F, Br, methyl, —($CF_3$) and cyclopropyl; and wherein, if position (3) of the ring of Formula (II) is $sp^3$-hybridized, $R^9$ is preferably (R)- or (S)-configured, more preferably (S)-configured; and/or $R^{10}$ is absent or selected from the group consisting of (i) hydrogen;

(ii) methyl; and (iii) cyclopropyl and phenyl that is mono-substituted in para position by a substituent selected from the group consisting of H, C, F, Br, methyl, —($CF_3$) and cyclopropyl, wherein $R^{10}$ is absent if X is C and/or if the ring of Formula (II) has a double bond between positions (1) and (2) or between positions (2) and (3) of the ring of Formula (II).

In a further preferred embodiment, the compound for use according to the present invention is a compound of Formula (I), wherein a double bond is located between positions (3) and (4) (Formula Ia)

Formula (Ia)

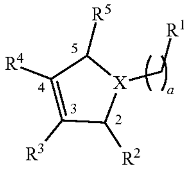

wherein X is N and a is 0, and wherein $R^1$ is selected from the group consisting of substituted or non-substituted indazolyl, benzimidazolyl and benzodioxolyl, preferably mono-, di-, tri- or tetrafluorinated benzodioxolyl, connected via position (6) or (5), preferably via position (6) of the indazolyl and benzodioxolyl or position (5) of the benzimidazolyl; and/or $R^2$ is oxo; and/or $R^3$ is selected from the group consisting of (i) hydrogen;

(ii) methyl; and (iii)

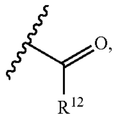

wherein $R^{12}$ is selected from the group consisting of (aa) N; and (bb) cyclopropyl, fluorinated cyclopropyl, and phenyl that is mono-substituted in para position by cyclopropyl or —($CF_3$), or di-substituted in meta position by cyclopropyl or —($CF_3$) in each meta position; and/or $R^4$ is hydroxyl; and/or $R^5$ is selected from the group consisting of (i) hydrogen;

(ii) methyl;

(iii) cyclopropyl and phenyl that is mono, di-, tri- or tetra-substituted or mono-substituted in para position by a substituent selected from the group consisting of H, Cl, F, Br, methyl, —($CF_3$) and cyclopropyl;

(iv) cyclopenta-2,4-dien-1-yl; and (v) imidazolyl and pyrazolyl connected via the imidazolyl-/pyrazolyl-position-(1)-nitrogen to the ring of Formula (I);

wherein $R^5$ is preferably (R)- or (S)-configured, more preferably (R)-configured.

In a further preferred embodiment, the compound for use according to the present invention is a compound of Formula (I), wherein two double bonds are located between positions (2) and (3) and between positions (4) and (5), respectively (Formula Ib)

Formula (Ib)

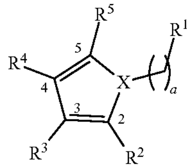

wherein X is N or C, preferably N, a is 0 or 1, preferably a is 0 if X is C, and wherein $R^1$ is selected from the group consisting of indazolyl, benzimidazolyl and benzodioxolyl connected via position (5) or (6), preferably via position (6) of the indazolyl and benzodioxolyl or position (5) of the benzimidazolyl; and/or $R^2$ is selected from the group consisting of (i) hydrogen; and (ii) methyl; and/or $R^3$ is selected from the group consisting of (i) hydrogen;

(ii) methyl; and (iii)

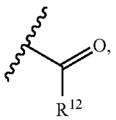

wherein $R^{12}$ is selected from the group consisting of (aa) N; and (bb) cyclopropyl and phenyl that is mono-substituted in para position by cyclopropyl or —($CF_3$), or di-substituted in meta position by cyclopropyl or —($CF_3$) in each meta position; and/or $R^4$ is hydrogen; and/or $R^5$ is selected from the group consisting of (i) hydrogen;

(ii) methyl; and (iii) cyclopropyl and phenyl that is mono-substituted in para position by a substituent selected from the group consisting of H, C, F, Br, methyl, —($CF_3$) and cyclopropyl.

In a further preferred embodiment, the compound for use according to the present invention is a compound of Formula (I), wherein the bonds in the five-membered ring of Formula (I) are fully saturated (Formula Ic)

Formula (Ic)

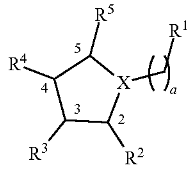

wherein X is N, a is 0 and wherein $R^1$ is selected from the group consisting of (i) hydrogen;

(ii) methyl; and (iii) cyclopropyl and phenyl that is mono-substituted in para position by a substituent selected from the group consisting of H, C, F, Br, methyl, —($CF_3$) and cyclopropyl; and/or $R^2$ is selected from the group consisting of (i) hydrogen; and (ii) indazolyl, benzimidazolyl and benzodioxolyl, preferably indazolyl, benzimidazolyl and benzodioxolyl connected via position (5) or (6), more preferably via position (5) of the indazolyl and benzodioxolyl or position (6) of the benzimidazolyl if $R^3$ is not methyl, most preferably via position (6) of the indazolyl and benzodioxolyl or position (5) of the benzimidazolyl if $R^3$ is methyl; and/or $R^3$ is selected from the group consisting of (i) hydrogen or methyl; and (ii)

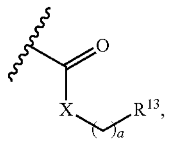

wherein X is N, a is 1 and $R^{13}$ is selected from the group consisting of indazolyl, benzimidazolyl and benzodioxolyl connected via position (6) or (5) of indazolyl, benzimidazolyl and benzodioxolyl, preferably via position (5) of the indazolyl and benzodioxolyl or position (6) of the benzimidazolyl; and/or $R^4$ is selected from the group consisting of (i) hydrogen;

(ii) methyl;

(iii)

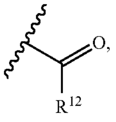

wherein $R^{12}$ is selected from the group consisting of (aa) N; and (bb) cyclopropyl and phenyl that is mono-substituted in para position by cyclopropyl or —($CF_3$), or di-substituted in meta position by cyclopropyl or —($CF_3$) in each meta position; and (iv)

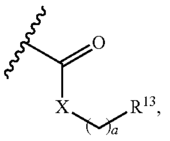

wherein X is N, a is 1 and $R^{13}$ is phenyl that is mono-substituted in meta position by cyclopropyl or —($CF_3$), or di-substituted in each meta position by cyclopropyl or —($CF_3$), or mono-substituted in para position by cyclopropyl or —($CF_3$);

wherein, $R^2$ and $R^4$ and/or $R^3$ and $R^4$ are preferably in a trans configuration to each other, preferably, $R^2$ is (S)-, $R^3$ is (S)- and $R^4$ is (R)-configured; and/or $R^5$ is hydrogen.

In a further preferred embodiment, the compound for use according to the present invention is a compound of Formula (II), wherein the bonds within the ring of Formula (II) are fully saturated (Formula IIa)

Formula (IIa)

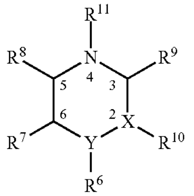

wherein X is C, Y is S and wherein $R^6$ is not present; and/or $R^7$ is selected from the group consisting of (i) hydrogen;

(ii) methyl; and (iii)

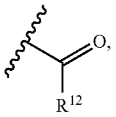

wherein $R^1$ is selected from the group consisting of (aa) N; and (bb) cyclopropyl or phenyl mono-substituted in para position by cyclopropyl or —($CF_3$) or di-substituted in meta position by cyclopropyl or —($CF_3$) in each meta position; and/or $R^8$ is selected from the group consisting of (i) hydrogen and methyl; and (ii)

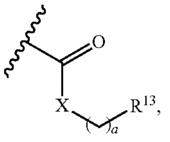

wherein X is N, a is 1 and $R^1$ is selected from the group consisting of indazolyl, benzimidazolyl and benzodioxolyl connected via position (6) or (5), preferably via position (5) of the indazolyl and benzodioxolyl or position (6) of the benzimidazolyl;

wherein $R^8$ is preferably (R)- or (S)-configured, more preferably (R)-configured; and/or $R^9$ is selected from the group consisting of (i) hydrogen, methyl and cyclopropyl; and (ii) phenyl that is mono-substituted in para position by a substituent selected from the group consisting of H, Cl, F, Br, methyl, —($CF_3$) and cyclopropyl;

wherein $R^9$ is preferably (R)- or (S)-configured, more preferably (S)-configured; and/or $R^{10}$ is hydrogen; and/or $R^{11}$ is hydrogen or selected from the group consisting of indazolyl, benzimidazolyl and benzodioxolyl connected via position (6) or (5), preferably via position (6) of the indazolyl and benzodioxolyl or position (5) of the benzimidazolyl.

In a further preferred embodiment, the compound for use according to the present invention is a compound of Formula (II), wherein the ring of Formula (II) is aromatic (Formula IIb)

Formula (IIb)

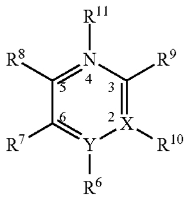

wherein X is N, Y is C and wherein $R^6$ is selected from the group consisting of substituted or non-substituted indazolyl, benzimidazolyl and benzodioxolyl, preferably mono-, di-, tri- or tetrafluorinated benzodioxolyl, connected via position (6) or (5), preferably via position (6) of the indazolyl and benzodioxolyl or position (5) of the benzimidazolyl; and/or $R^7$ and $R^8$ are independently selected from the group consisting of (i) hydrogen or fluorine;

(ii) methyl; and (iii)

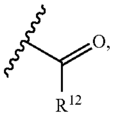

wherein $R^1$ is selected from the group consisting of (aa) N; and (bb) cyclopropyl and phenyl that is mono-substituted in para position by cyclopropyl or —($CF_3$), or di-substituted in meta position by cyclopropyl or —($CF_3$) in each meta position;

and/or $R^9$ is hydrogen or fluorine; and/or $R^{10}$ and/or $R^1$ are absent.

In a further preferred embodiment, the compound for use according to the present invention is a compound of Formula (II), wherein two double bonds are located between positions (1) and (6) and between positions (4) and (5), respectively (Formula IIc)

Formula (IIc)

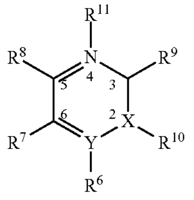

wherein X is N, Y is C and wherein $R^6$ is selected from the group consisting of indazolyl, benzimidazolyl and benzodioxolyl connected via position (6) or (5), preferably via position (6) of the indazolyl and benzodioxolyl or position (5) of the benzimidazolyl; and/or $R^7$ and $R^8$ are independently selected from the group consisting of hydrogen and methyl;

and/or $R^9$ is hydrogen; and/or $R^{10}$ is selected from the group consisting of (i) hydrogen;

(ii) methyl; and (iii) cyclopropyl and phenyl that is mono-substituted in para position by a substituent selected from the group consisting of H, C, F, Br, methyl, —($CF_3$) and cyclopropyl; and/or $R^{11}$ is absent.

In a further preferred embodiment, the compound for use according to the present invention is a compound, wherein $R^1$ is selected from the group consisting of hydrogen, methyl,

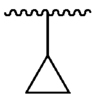 , 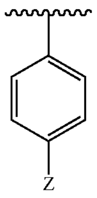 , 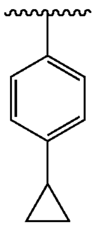 , 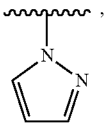 ,

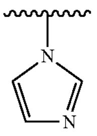 , 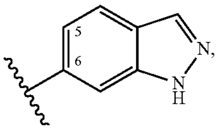

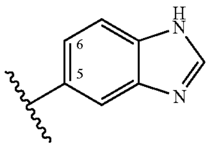 and 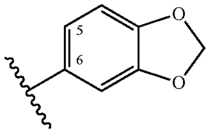

Z = H, Me, ($CF_3$), F, Cl, Br wherein optionally all free carbon ring positions are selected from hydrogen or fluorine, and/or $R^2$ is selected from the group consisting of hydrogen, oxo, methyl,

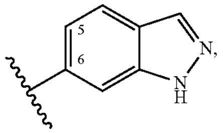 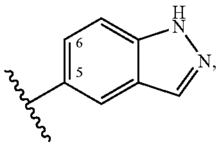

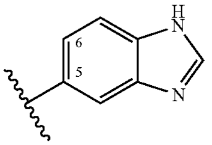 , 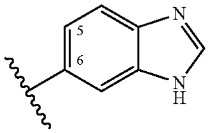 and

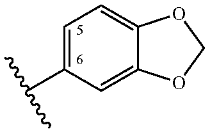

and/or $R^3$ is selected from the group consisting of hydrogen, methyl,

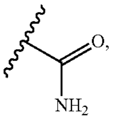 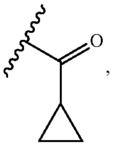 , 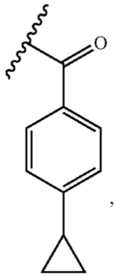 , 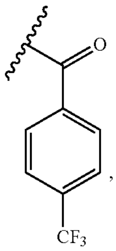 ,

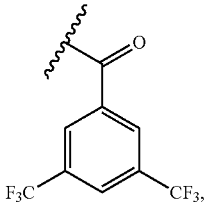 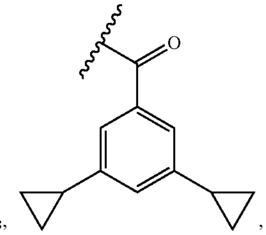 ,

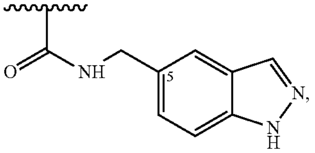

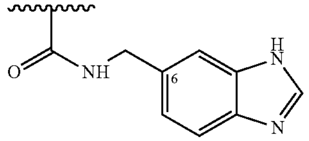 and

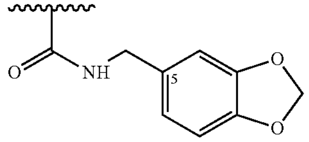

wherein optionally all free carbon ring positions are selected from hydrogen or fluorine, and/or $R^4$ is selected from the group consisting of hydrogen, hydroxyl, methyl,

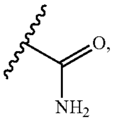
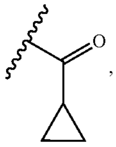
,
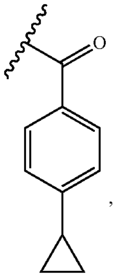
,
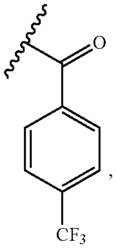
,
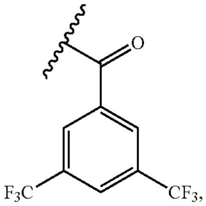
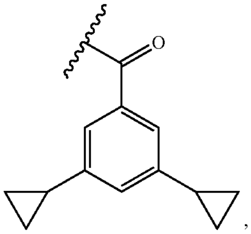
,
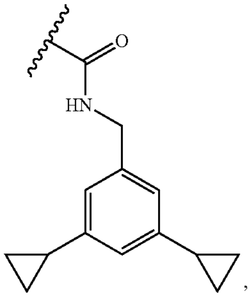
,
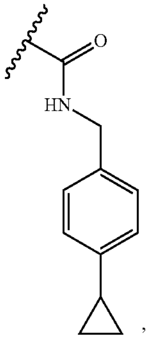
,
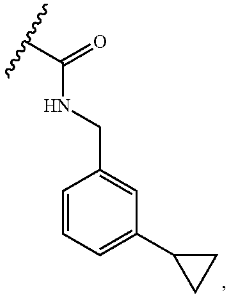
,
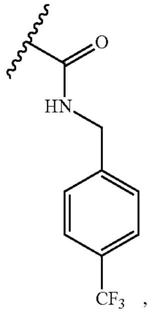
,
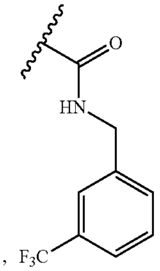
and
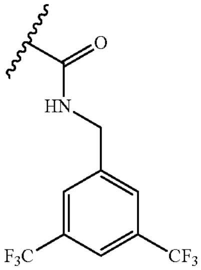

wherein, $R^4$ and/or $R^3$ and $R^4$ are preferably in cis or trans configuration to each other, more preferably in trans configuration, preferably, $R^2$ is (R)- or (S)-, $R^3$ is (R)- or (S)- and/or $R^4$ is (R)- or (S)-configured, more preferably, $R^2$ is (R)-, $R^3$ is (R)- and/or $R^4$ is (R)-configured, or $R^2$ is or (S)-, $R^3$ is (S)- and/or $R^4$ is (S)-configured, and/or $R^5$ and $R^9$ are selected from the group consisting of hydrogen, fluorine, methyl, cyclopenta-2,4-dien-1-yl,

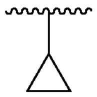
,
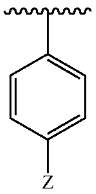
,
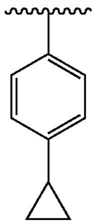
,
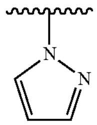
, and
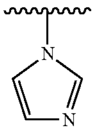

Z = H, Me, ($CF_3$), F, Cl, Br wherein $R^9$ is preferably not cyclopenta-2,4-dien-1-yl, wherein, if position (5) of the ring of Formula (I) is $sp^3$-hybridized, $R^5$ is preferably (R)- or (S)-configured, more preferably (R)-configured, wherein optionally all free carbon ring positions are selected from hydrogen or fluorine, and wherein $R^9$ is preferably (R)- or (S)-configured, more preferably (R)-configured, and/or $R^6$ is not present if Y is S, and if Y is C, $R^6$ is selected from the group consisting of

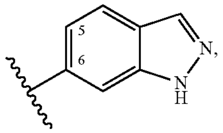
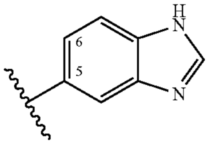
and
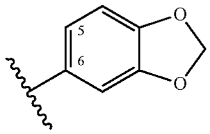

wherein optionally all free carbon ring positions are selected from hydrogen or fluorine, and/or $R^7$ and $R^8$ are selected from the group consisting of hydrogen, fluorine, methyl,

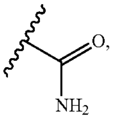
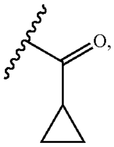
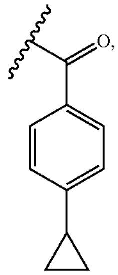
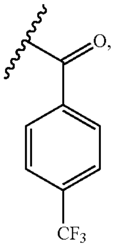

-continued

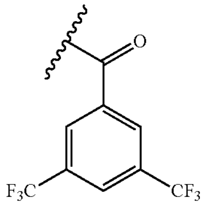

and

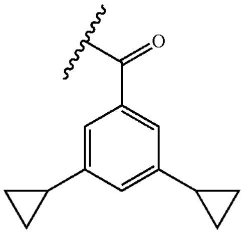

wherein $R^8$ is additionally selected from the group consisting of

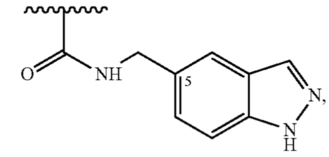

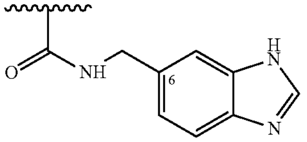

and

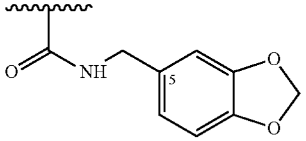

and wherein $R^8$ is preferably (R)- or (S)-configured, more preferably (R)-configured; and/or $R^{10}$ is absent or selected from the group consisting of hydrogen, methyl,

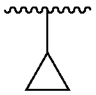

,

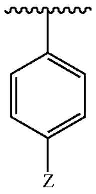

and

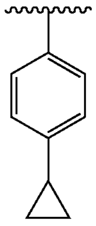

,

Z = H, Me, ($CF_3$), F, Cl, Br wherein $R^{10}$ is absent if X is C and/or if the ring of Formula (II) has a double bond between positions (1) and (2) or between positions (2) and (3) of the ring of Formula (II), and/or $R^{11}$ is absent or selected from the group consisting of hydrogen,

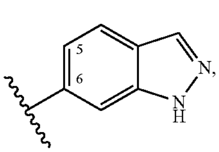

,

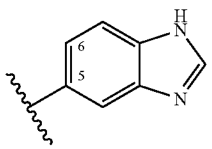

and

-continued

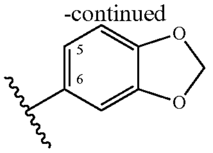

, wherein $R^{11}$ is absent if the ring of Formula (II) has a double bond between positions (4) and (5) or between positions (3) and (4) of the ring of Formula (II).

In a further preferred embodiment, the compound for use according to the present invention is a compound selected from the group consisting of:

(i) a First Residue Selected from the Group Consisting of 1-(1,3-benzodioxol-5-yl)-3-hydroxy-5-oxo-2-methyl-2H-pyrrol-4-yl, 1-(1,3-benzodioxol-5-yl)-2-cyclopropyl-3-hydroxy-5-oxo-2H-pyrrol-4-yl, 1-(1,3-benzodioxol-5-yl)-3-hydroxy-5-oxo-2H-pyrrol-4-yl, 1-(1,3-benzodioxol-5-yl)-2-(cyclopenta-2,4-dien-1-yl)-5-oxo-3-hydroxy-2H-pyrrol-4-yl, 1-(1,3-benzodioxol-5-yl)-3-hydroxy-5-oxo-2-(pyrazol-1-yl)-2H-pyrrol-4-yl, 1-(1,3-benzodioxol-5-yl)-3-hydroxy-5-oxo-2-(imidazol-1-yl)-2H-pyrrol-4-yl, 1-(1,3-benzodioxol-5-yl)-3-hydroxy-5-oxo-2-phenyl-2H-pyrrol-4-yl, 1-(1,3-benzodioxol-5-yl)-3-hydroxy-5-oxo-2-(p-tolyl)-2H-pyrrol-4-yl, 1-(1,3-benzodioxol-5-yl)-2-(4-chlorophenyl)-3-hydroxy-5-oxo-2H-pyrrol-4-yl, 1-(1,3-benzodioxol-5-yl)-2-(4-fluorophenyl)-3-hydroxy-5-oxo-2H-pyrrol-4-yl, 1-(1,3-benzodioxol-5-yl)-2-(4-bromophenyl)-3-hydroxy-5-oxo-2H-pyrrol-4-yl, 1-(1,3-benzodioxol-5-yl)-2-(4-cyclopropylphenyl)-3-hydroxy-5-oxo-2H-pyrrol-4-yl, 1-(1,3-benzodioxol-5-yl)-3-hydroxy-5-oxo-2-[4-(trifluoromethyl)phenyl]-2H-pyrrol-4-yl, 3-hydroxy-1-(1H-indazol-6-yl)-5-oxo-2-[4-(trifluoromethyl)phenyl]-2H-pyrrol-4-yl, 3-hydroxy-1-(1H-indazol-6-yl)-5-oxo-2-phenyl-2H-pyrrol-4-yl, 3-hydroxy-1-(1H-indazol-6-yl)-5-oxo-2-(p-tolyl)-2H-pyrrol-4-yl, 2-(4-chlorophenyl)-3-hydroxy-1-(1H-indazol-6-yl)-5-oxo-2H-pyrrol-4-yl, 2-(4-fluorophenyl)-3-hydroxy-1-(1H-indazol-6-yl)-5-oxo-2H-pyrrol-4-yl, 2-(4-bromophenyl)-3-hydroxy-1-(1H-indazol-6-yl)-5-oxo-2H-pyrrol-4-yl, 2-(4-cyclopropylphenyl)-3-hydroxy-1-(1H-indazol-6-yl)-5-oxo-2H-pyrrol-4-yl, 2-cyclopropyl-3-hydroxy-1-(1H-indazol-6-yl)-5-oxo-2H-pyrrol-4-yl, 3-hydroxy-1-(1H-indazol-6-yl)-5-oxo-2-methyl-2H-pyrrol-4-yl, 3-hydroxy-1-(1H-indazol-6-yl)-5-oxo-2H-pyrrol-4-yl, 3-hydroxy-1-(1H-indazol-6-yl)-5-oxo-2-(pyrazol-1-yl)-2H-pyrrol-4-yl, 2-(cyclopenta-2,4-dien-1-yl)-3-hydroxy-1-(1H-indazol-6-yl)-5-oxo-2H-pyrrol-4-yl, 3-hydroxy-2-(imidazol-1-yl)-1-(1H-indazol-6-yl)-5-oxo-2H-pyrrol-4-yl, 1-(1H-benzimidazol-5-yl)-3-hydroxy-5-oxo-2-dimethyl-2H-pyrrol-4-yl,
1-(1H-benzimidazol-5-yl)-2-cyclopropyl-3-hydroxy-5-oxo-2H-pyrrol-4-yl,
1-(1H-benzimidazol-5-yl)-3-hydroxy-5-oxo-2-(pyrazol-1-yl)-2H-pyrrol-4-yl,
1-(1H-benzimidazol-5-yl)-3-hydroxy-5-oxo-2H-pyrrol-4-yl,
1-(1H-benzimidazol-5-yl)-3-hydroxy-5-oxo-2-(imidazol-1-yl)-2H-pyrrol-4-yl,
1-(1H-benzimidazol-5-yl)-2-(cyclopenta-2,4-dien-1-yl)-3-hydroxy-5-oxo-2H-pyrrol-4-yl,
1-(1H-benzimidazol-5-yl)-2-(4-fluorophenyl)-3-hydroxy-5-oxo-2H-pyrrol-4-yl,
1-(1H-benzimidazol-5-yl)-3-hydroxy-5-oxo-2-[4-(trifluoromethyl)phenyl]-2H-pyrrol-4-yl,
1-(1H-benzimidazol-5-yl)-3-hydroxy-5-oxo-2-phenyl-2H-pyrrol-4-yl,
1-(1H-benzimidazol-5-yl)-3-hydroxy-5-oxo-2-(p-tolyl)-2H-pyrrol-4-yl,
1-(1H-benzimidazol-5-yl)-2-(4-chlorophenyl)-3-hydroxy-5-oxo-2H-pyrrol-4-yl,
1-(1H-benzimidazol-5-yl)-2-(4-bromophenyl)-3-hydroxy-5-oxo-2H-pyrrol-4-yl,
1-(1H-benzimidazol-5-yl)-2-(4-cyclopropylphenyl)-3-hydroxy-5-oxo-2H-pyrrol-4-yl,
wherein the numbering of the 2H-pyrrole ring is as follows:

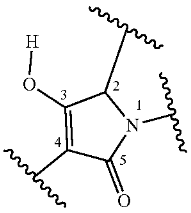
, 1-(1,3-benzodioxol-5-ylmethyl)-2-methyl-5-(p-tolyl)pyrrol-3-yl,
1-(1,3-benzodioxol-5-ylmethyl)-5-(4-chlorophenyl)-2-methyl-pyrrol-3-yl,
1-(1,3-benzodioxol-5-ylmethyl)-5-(4-fluorophenyl)-2-methyl-pyrrol-3-yl,
1-(1,3-benzodioxol-5-ylmethyl)-2-methyl-5-[4-(trifluoromethyl)phenyl]pyrrol-3-yl,
1-(1,3-benzodioxol-5-ylmethyl)-5-(4-bromophenyl)-2-methyl-pyrrol-3-yl,
1-(1,3-benzodioxol-5-ylmethyl)-5-(4-cyclopropylphenyl)-2-methyl-pyrrol-3-yl,
1-(1,3-benzodioxol-5-ylmethyl)-2-methyl-5-phenyl-pyrrol-3-yl,
1-(1,3-benzodioxol-5-ylmethyl)-5-phenyl-pyrrol-3-yl,
1-(1,3-benzodioxol-5-ylmethyl)-5-(p-tolyl)pyrrol-3-yl,
1-(1,3-benzodioxol-5-ylmethyl)-5-(4-fluorophenyl)pyrrol-3-yl,
1-(1,3-benzodioxol-5-ylmethyl)-5-[4-(trifluoromethyl)phenyl]pyrrol-3-yl,
1-(1,3-benzodioxol-5-ylmethyl)-5-(4-chlorophenyl)pyrrol-3-yl,
1-(1,3-benzodioxol-5-ylmethyl)-5-(4-bromophenyl)pyrrol-3-yl,
1-(1,3-benzodioxol-5-ylmethyl)-5-(4-cyclopropylphenyl)pyrrol-3-yl,
1-(1,3-benzodioxol-5-ylmethyl)-2,5-dimethyl-pyrrol-3-yl,
1-(1,3-benzodioxol-5-ylmethyl)-2-methyl-pyrrol-3-yl,
1-(1,3-benzodioxol-5-ylmethyl)-5-cyclopropyl-2-methyl-pyrrol-3-yl,
1-(1,3-benzodioxol-5-ylmethyl)pyrrol-3-yl,
1-(1,3-benzodioxol-5-ylmethyl)-5-methyl-pyrrol-3-yl,
1-(1,3-benzodioxol-5-ylmethyl)-5-cyclopropyl-pyrrol-3-yl,
1-(1H-indazol-6-ylmethyl)-2-methyl-5-phenyl-pyrrol-3-yl,
1-(1H-indazol-6-ylmethyl)-2-methyl-5-(p-tolyl)pyrrol-3-yl,
5-(4-chlorophenyl)-1-(1H-indazol-6-ylmethyl)-2-methyl-pyrrol-3-yl,
5-(4-fluorophenyl)-1-(1H-indazol-6-ylmethyl)-2-methyl-pyrrol-3-yl,
1-(1H-indazol-6-ylmethyl)-2-methyl-5-[4-(trifluoromethyl)phenyl]pyrrol-3-yl,
5-(4-bromophenyl)-1-(1H-indazol-6-ylmethyl)-2-methyl-pyrrol-3-yl,
5-(4-cyclopropylphenyl)-1-(1H-indazol-6-ylmethyl)-2-methyl-pyrrol-3-yl,
1-(1H-indazol-6-ylmethyl)-5-phenyl-pyrrol-3-yl,
1-(1H-indazol-6-ylmethyl)-5-(p-tolyl)pyrrol-3-yl,
5-(4-fluorophenyl)-1-(1H-indazol-6-ylmethyl)pyrrol-3-yl,
1-(1H-indazol-6-ylmethyl)-5-[4-(trifluoromethyl)phenyl]pyrrol-3-yl,
5-(4-chlorophenyl)-1-(1H-indazol-6-ylmethyl)pyrrol-3-yl,
5-(4-bromophenyl)-1-(1H-indazol-6-ylmethyl)pyrrol-3-yl,
5-(4-cyclopropylphenyl)-1-(1H-indazol-6-ylmethyl)pyrrol-3-yl,
5-cyclopropyl-1-(1H-indazol-6-ylmethyl)-2-methyl-pyrrol-3-yl,
1-(1H-indazol-6-ylmethyl)-2-methyl-pyrrol-3-yl,
1-(1H-indazol-6-ylmethyl)-2,5-dimethyl-pyrrol-3-yl,
1-(1H-indazol-6-ylmethyl)pyrrol-3-yl,
5-cyclopropyl-1-(1H-indazol-6-ylmethyl)pyrrol-3-yl,
1-(1H-indazol-6-ylmethyl)-5-methyl-pyrrol-3-yl,
1-(1H-benzimidazol-5-ylmethyl)-2-methyl-5-phenyl-pyrrol-3-yl,
1-(1H-benzimidazol-5-ylmethyl)-2-methyl-5-(p-tolyl)pyrrol-3-yl,
1-(1H-benzimidazol-5-ylmethyl)-2-methyl-5-(p-tolyl)pyrrol-3-yl,
1-(1H-benzimidazol-5-ylmethyl)-5-(4-fluorophenyl)-2-methyl-pyrrol-3-yl,
1-(1H-benzimidazol-5-ylmethyl)-5-(4-cyclopropylphenyl)-2-methyl-pyrrol-3-yl,
1-(1H-benzimidazol-5-ylmethyl)-5-(4-bromophenyl)-2-methyl-pyrrol-3-yl,
1-(1H-benzimidazol-5-ylmethyl)-2-methyl-5-[4-(trifluoromethyl)phenyl]pyrrol-3-yl,
1-(1H-benzimidazol-5-ylmethyl)-5-phenyl-pyrrol-3-yl,
1-(1H-benzimidazol-5-ylmethyl)-5-(p-tolyl)pyrrol-3-yl,
1-(1H-benzimidazol-5-ylmethyl)-5-[4-(trifluoromethyl)phenyl]pyrrol-3-yl,
1-(1H-benzimidazol-5-ylmethyl)-5-(4-chlorophenyl)pyrrol-3-yl,
1-(1H-benzimidazol-5-ylmethyl)-5-(4-fluorophenyl)pyrrol-3-yl,
1-(1H-benzimidazol-5-ylmethyl)-5-(4-bromophenyl)pyrrol-3-yl,
1-(1H-benzimidazol-5-ylmethyl)-5-(4-cyclopropylphenyl)pyrrol-3-yl,
1-(1H-benzimidazol-5-ylmethyl)-2,5-dimethyl-pyrrol-3-yl,
1-(1H-benzimidazol-5-ylmethyl)-2-methyl-pyrrol-3-yl,
1-(1H-benzimidazol-5-ylmethyl)-5-cyclopropyl-2-methyl-pyrrol-3-yl,
1-(1H-benzimidazol-5-ylmethyl)-5-methyl-pyrrol-3-yl,
1-(1H-benzimidazol-5-ylmethyl)pyrrol-3-yl,
1-(1H-benzimidazol-5-ylmethyl)-5-cyclopropyl-pyrrol-3-yl, 1-(1,3-benzodioxol-5-yl)-5-(p-tolyl)pyrrol-3-yl,
1-(1,3-benzodioxol-5-yl)-5-phenyl-pyrrol-3-yl,
1-(1,3-benzodioxol-5-yl)-5-(4-fluorophenyl)pyrrol-3-yl,
1-(1,3-benzodioxol-5-yl)-5-[4-(trifluoromethyl)phenyl]pyrrol-3-yl,
1-(1,3-benzodioxol-5-yl)-5-(4-bromophenyl)pyrrol-3-yl,
1-(1,3-benzodioxol-5-yl)-5-(4-chlorophenyl)pyrrol-3-yl,
1-(1,3-benzodioxol-5-yl)-5-(4-cyclopropylphenyl)pyrrol-3-yl,
1-(1,3-benzodioxol-5-yl)-2-methyl-5-(p-tolyl)pyrrol-3-yl,
1-(1,3-benzodioxol-5-yl)-2-methyl-5-phenyl-pyrrol-3-yl,
1-(1,3-benzodioxol-5-yl)-5-(4-fluorophenyl)-2-methyl-pyrrol-3-yl,
1-(1,3-benzodioxol-5-yl)-2-methyl-5-[4-(trifluoromethyl)phenyl]pyrrol-3-yl,
1-(1,3-benzodioxol-5-yl)-5-(4-chlorophenyl)-2-methyl-pyrrol-3-yl,
1-(1,3-benzodioxol-5-yl)-5-(4-bromophenyl)-2-methyl-pyrrol-3-yl,
1-(1,3-benzodioxol-5-yl)-5-(4-cyclopropylphenyl)-2-methyl-pyrrol-3-yl,
1-(1,3-benzodioxol-5-yl)-2,5-dimethyl-pyrrol-3-yl,
1-(1,3-benzodioxol-5-yl)-2-methyl-pyrrol-3-yl,
1-(1,3-benzodioxol-5-yl)-5-cyclopropyl-2-methyl-pyrrol-3-yl,
1-(1,3-benzodioxol-5-yl)-5-methyl-pyrrol-3-yl,
1-(1,3-benzodioxol-5-yl)pyrrol-3-yl,
1-(1,3-benzodioxol-5-yl)-5-cyclopropyl-pyrrol-3-yl,
1-(1H-indazol-6-yl)-5-(p-tolyl)pyrrol-3-yl,
5-(4-chlorophenyl)-1-(1H-indazol-6-yl)pyrrol-3-yl,
5-(4-bromophenyl)-1-(1H-indazol-6-yl)pyrrol-3-yl,
5-(4-fluorophenyl)-1-(1H-indazol-6-yl)pyrrol-3-yl,
1-(1H-indazol-6-yl)-5-phenyl-pyrrol-3-yl,
5-(4-cyclopropylphenyl)-1-(1H-indazol-6-yl)pyrrol-3-yl,
1-(1H-indazol-6-yl)-5-[4-(trifluoromethyl)phenyl]pyrrol-3-yl,
1-(1H-indazol-6-yl)-2-methyl-5-(p-tolyl)pyrrol-3-yl,
5-(4-chlorophenyl)-1-(1H-indazol-6-yl)-2-methyl-pyrrol-3-yl,
5-(4-bromophenyl)-1-(1H-indazol-6-yl)-2-methyl-pyrrol-3-yl,
5-(4-fluorophenyl)-1-(1H-indazol-6-yl)-2-methyl-pyrrol-3-yl,
1-(1H-indazol-6-yl)-2-methyl-5-phenyl-pyrrol-3-yl,
5-(4-cyclopropylphenyl)-1-(1H-indazol-6-yl)-2-methyl-pyrrol-3-yl,
1-(1H-indazol-6-yl)-2-methyl-5-[4-(trifluoromethyl)phenyl]pyrrol-3-yl,
1-(1H-indazol-6-yl)-2,5-dimethyl-pyrrol-3-yl,
1-(1H-indazol-6-yl)-2-methyl-pyrrol-3-yl,
5-cyclopropyl-1-(1H-indazol-6-yl)-2-methyl-pyrrol-3-yl,
1-(1H-indazol-6-yl)-5-methyl-pyrrol-3-yl,
1-(1H-indazol-6-yl)pyrrol-3-yl,
5-cyclopropyl-1-(1H-indazol-6-yl)pyrrol-3-yl,
1-(1H-benzimidazol-5-yl)-5-(p-tolyl)pyrrol-3-yl,
1-(1H-benzimidazol-5-yl)-5-(4-chlorophenyl)pyrrol-3-yl,
1-(1H-benzimidazol-5-yl)-5-(4-bromophenyl)pyrrol-3-yl,
1-(1H-benzimidazol-5-yl)-5-(4-fluorophenyl)pyrrol-3-yl,
1-(1H-benzimidazol-5-yl)-5-phenyl-pyrrol-3-yl,
1-(1H-benzimidazol-5-yl)-5-(4-cyclopropylphenyl)pyrrol-3-yl,
1-(1H-benzimidazol-5-yl)-5-[4-(trifluoromethyl)phenyl]pyrrol-3-yl,
1-(1H-benzimidazol-5-yl)-2-methyl-5-(p-tolyl)pyrrol-3-yl,
1-(1H-benzimidazol-5-yl)-5-(4-chlorophenyl)-2-methyl-pyrrol-3-yl,
1-(1H-benzimidazol-5-yl)-5-(4-bromophenyl)-2-methyl-pyrrol-3-yl,
1-(1H-benzimidazol-5-yl)-5-(4-fluorophenyl)-2-methyl-pyrrol-3-yl,
1-(1H-benzimidazol-5-yl)-2-methyl-5-phenyl-pyrrol-3-yl,
1-(1H-benzimidazol-5-yl)-5-(4-cyclopropylphenyl)-2-methyl-pyrrol-3-yl,
1-(1H-benzimidazol-5-yl)-2-methyl-5-[4-(trifluoromethyl)phenyl]pyrrol-3-yl,
1-(1H-benzimidazol-5-yl)-2,5-dimethyl-pyrrol-3-yl,
1-(1H-benzimidazol-5-yl)-2-methyl-pyrrol-3-yl,
1-(1H-benzimidazol-5-yl)-5-cyclopropyl-2-methyl-pyrrol-3-yl,
1-(1H-benzimidazol-5-yl)-5-methyl-pyrrol-3-yl,
1-(1H-benzimidazol-5-yl)pyrrol-3-yl,
1-(1H-benzimidazol-5-yl)-5-cyclopropyl-pyrrol-3-yl,
wherein the numbering of the pyrrole ring is as follows:

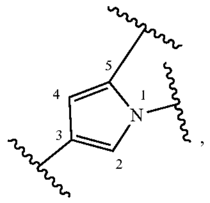 [SMILES: *c1cc(*)n(*)c1]

(3R)-3-(1,3-benzodioxol-5-ylmethylcarbamoyl)-5-phenyl-thiomorpholin-2-yl,
(3R)-3-(1,3-benzodioxol-5-ylmethylcarbamoyl)-5-(p-tolyl)thiomorpholin-2-yl,
(3R)-3-(1,3-benzodioxol-5-ylmethylcarbamoyl)-5-(4-fluorophenyl)thiomorpholin-2-yl,
(3R)-3-(1,3-benzodioxol-5-ylmethylcarbamoyl)-5-(4-bromophenyl)thiomorpholin-2-yl,
(3R)-3-(1,3-benzodioxol-5-ylmethylcarbamoyl)-5-(4-chlorophenyl)thiomorpholin-2-yl,
(3R)-3-(1,3-benzodioxol-5-ylmethylcarbamoyl)-5-(4-cyclopropylphenyl)thiomorpholin-2-yl,
(3R)-3-(1,3-benzodioxol-5-ylmethylcarbamoyl)-5-[4-(trifluoromethyl)phenyl]thio-morpholin-2-yl,
(3R)-3-(1H-indazol-5-ylmethylcarbamoyl)-5-phenyl-thiomorpholin-2-yl,
(3R)-3-(1H-indazol-5-ylmethylcarbamoyl)-5-(p-tolyl)thiomorpholin-2-yl,
(3R)-5-(4-fluorophenyl)-3-(1H-indazol-5-ylmethylcarbamoyl)thiomorpholin-2-yl,
(3R)-5-(4-bromophenyl)-3-(1H-indazol-5-ylmethylcarbamoyl)thiomorpholin-2-yl,
(3R)-5-(4-chlorophenyl)-3-(1H-indazol-5-ylmethylcarbamoyl)thiomorpholin-2-yl,
(3R)-5-(4-cyclopropylphenyl)-3-(1H-indazol-5-ylmethylcarbamoyl)thiomorpholin-2-yl,
(3R)-3-(1H-indazol-5-ylmethylcarbamoyl)-5-[4-(trifluoromethyl)phenyl]thiomorpholin-2-yl,
(3R)-3-(3H-benzimidazol-5-ylmethylcarbamoyl)-5-phenyl-thiomorpholin-2-yl,
(3R)-3-(3H-benzimidazol-5-ylmethylcarbamoyl)-5-(p-tolyl)thiomorpholin-2-yl,
(3R)-3-(3H-benzimidazol-5-ylmethylcarbamoyl)-5-(4-fluorophenyl)thiomorpholin-2-yl,
(3R)-3-(3H-benzimidazol-5-ylmethylcarbamoyl)-5-[4-(trifluoromethyl)phenyl]thio-morpholin-2-yl,
(3R)-3-(3H-benzimidazol-5-ylmethylcarbamoyl)-5-(4-bromophenyl)thiomorpholin-2-yl, (3R)-3-(3H-benzimidazol-5-ylmethylcarbamoyl)-5-(4-chlorophenyl)thiomorpholin-2-yl,
(3R)-3-(3H-benzimidazol-5-ylmethylcarbamoyl)-5-(4-cyclopropylphenyl)thio-morpholin-2-yl,
4-(1,3-benzodioxol-5-yl)-5-(4-fluorophenyl)thiomorpholin-2-yl,
4-(1,3-benzodioxol-5-yl)-5-(4-bromophenyl)thiomorpholin-2-yl,
4-(1,3-benzodioxol-5-yl)-5-(4-chlorophenyl)thiomorpholin-2-yl,
4-(1,3-benzodioxol-5-yl)-5-methyl-thiomorpholin-2-yl,
4-(1,3-benzodioxol-5-yl)-5-cyclopropyl-thiomorpholin-2-yl,
4-(1,3-benzodioxol-5-yl)-5-(4-cyclopropylphenyl)thiomorpholin-2-yl,
4-(1,3-benzodioxol-5-yl)-5-(p-tolyl)thiomorpholin-2-yl,
4-(1,3-benzodioxol-5-yl)-5-phenyl-thiomorpholin-2-yl,
4-(1,3-benzodioxol-5-yl)-5-[4-(trifluoromethyl)phenyl] thiomorpholin-2-yl,
4-(1,3-benzodioxol-5-yl)thiomorpholin-2-yl,
4-(1,3-benzodioxol-5-yl)-5-(4-fluorophenyl)-3-methyl-thiomorpholin-2-yl,
4-(1,3-benzodioxol-5-yl)-5-(4-bromophenyl)-3-methyl-thiomorpholin-2-yl,
4-(1,3-benzodioxol-5-yl)-5-(4-chlorophenyl)-3-methyl-thiomorpholin-2-yl,
4-(1,3-benzodioxol-5-yl)-3,5-dimethyl-thiomorpholin-2-yl,
4-(1,3-benzodioxol-5-yl)-5-cyclopropyl-3-methyl-thiomorpholin-2-yl,
4-(1,3-benzodioxol-5-yl)-5-(4-cyclopropylphenyl)-3-methyl-thiomorpholin-2-yl,
4-(1,3-benzodioxol-5-yl)-3-methyl-5-(p-tolyl)thiomorpholin-2-yl,
4-(1,3-benzodioxol-5-yl)-3-methyl-5-phenyl-thiomorpholin-2-yl,
4-(1,3-benzodioxol-5-yl)-3-methyl-5-[4-(trifluoromethyl) phenyl]thiomorpholin-2-yl,
4-(1,3-benzodioxol-5-yl)-3-methyl-thiomorpholin-2-yl,
5-(4-fluorophenyl)-4-(1H-indazol-6-yl)thiomorpholin-2-yl,
5-(4-bromophenyl)-4-(1H-indazol-6-yl)thiomorpholin-2-yl,
5-(4-chlorophenyl)-4-(1H-indazol-6-yl)thiomorpholin-2-yl,
4-(1H-indazol-6-yl)-5-methyl-thiomorpholin-2-yl,
5-cyclopropyl-4-(1H-indazol-6-yl)thiomorpholin-2-yl,
5-(4-cyclopropylphenyl)-4-(1H-indazol-6-yl)thiomorpholin-2-yl,
4-(1H-indazol-6-yl)-5-(p-tolyl)thiomorpholin-2-yl,
4-(1H-indazol-6-yl)-5-phenyl-thiomorpholin-2-yl,
4-(1H-indazol-6-yl)-5-[4-(trifluoromethyl)phenyl]thiomorpholin-2-yl,
4-(1H-indazol-6-yl)thiomorpholin-2-yl,
5-(4-fluorophenyl)-4-(1H-indazol-6-yl)-3-methyl-thiomorpholin-2-yl,
5-(4-bromophenyl)-4-(1H-indazol-6-yl)-3-methyl-thiomorpholin-2-yl,
5-(4-chlorophenyl)-4-(1H-indazol-6-yl)-3-methyl-thiomorpholin-2-yl,
4-(1H-indazol-6-yl)-3,5-dimethyl-thiomorpholin-2-yl,
5-(4-cyclopropylphenyl)-4-(1H-indazol-6-yl)-3-methyl-thiomorpholin-2-yl,
4-(1H-indazol-6-yl)-3-methyl-5-(p-tolyl)thiomorpholin-2-yl,
4-(1H-indazol-6-yl)-3-methyl-5-phenyl-thiomorpholin-2-yl,
5-cyclopropyl-4-(1H-indazol-6-yl)-3-methyl-thiomorpholin-2-yl,
4-(1H-indazol-6-yl)-3-methyl-thiomorpholin-2-yl,
4-(1H-indazol-6-yl)-3-methyl-5-[4-(trifluoromethyl)phenyl]thiomorpholin-2-yl,
4-(1H-benzimidazol-5-yl)-5-(4-fluorophenyl)thiomorpholin-2-yl,
4-(1H-benzimidazol-5-yl)-5-(4-bromophenyl)thiomorpholin-2-yl,
4-(1H-benzimidazol-5-yl)-5-(4-chlorophenyl)thiomorpholin-2-yl,
4-(1H-benzimidazol-5-yl)-5-methyl-thiomorpholin-2-yl,
4-(1H-benzimidazol-5-yl)-5-cyclopropyl-thiomorpholin-2-yl,
4-(1H-benzimidazol-5-yl)-5-(4-cyclopropylphenyl)thiomorpholin-2-yl,
4-(1H-benzimidazol-5-yl)-5-(p-tolyl)thiomorpholin-2-yl,
4-(1H-benzimidazol-5-yl)-5-phenyl-thiomorpholin-2-yl,
4-(1H-benzimidazol-5-yl)-5-[4-(trifluoromethyl)phenyl] thiomorpholin-2-yl,
4-(1H-benzimidazol-5-yl)thiomorpholin-2-yl,
4-(1H-benzimidazol-5-yl)-5-(4-fluorophenyl)-3-methyl-thiomorpholin-2-yl,
4-(1H-benzimidazol-5-yl)-5-(4-bromophenyl)-3-methyl-thiomorpholin-2-yl,
4-(1H-benzimidazol-5-yl)-5-(4-chlorophenyl)-3-methyl-thiomorpholin-2-yl,
4-(1H-benzimidazol-5-yl)-3,5-dimethyl-thiomorpholin-2-yl,
4-(1H-benzimidazol-5-yl)-5-cyclopropyl-3-methyl-thiomorpholin-2-yl,
4-(1H-benzimidazol-5-yl)-5-(4-cyclopropylphenyl)-3-methyl-thiomorpholin-2-yl,
4-(1H-benzimidazol-5-yl)-3-methyl-5-(p-tolyl)thiomorpholin-2-yl,
4-(1H-benzimidazol-5-yl)-3-methyl-5-phenyl-thiomorpholin-2-yl,
4-(1H-benzimidazol-5-yl)-3-methyl-5-[4-(trifluoromethyl) phenyl]thiomorpholin-2-yl,
4-(1H-benzimidazol-5-yl)-3-methyl-thiomorpholin-2-yl,
wherein the numbering of the thiomorpholine ring is as follow:

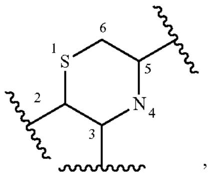
,

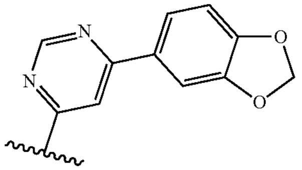
6-(1,3-benzodioxol-5-yl)pyrimidin-4-yl
,

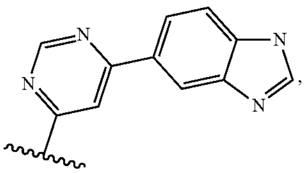
6-(1H-benzimidazol-5-yl)pyrimidin-4-yl

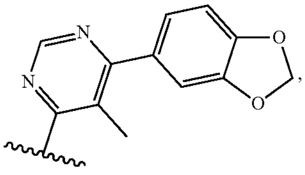
6-(1,3-benzodioxol-5-yl)-5-methyl-pyrimidin-4-yl

-continued

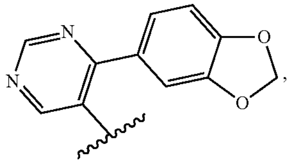

4-(1,3-benzodioxol-5-yl) pyrimidin-5-yl

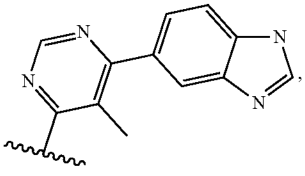

6-(1H-benzimidazol-5-yl)-5-methyl-pyrimidin-4-yl

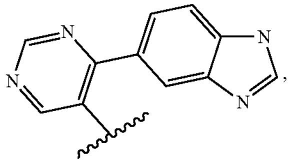

4-(1H-benzimidazol-5-yl) pyrimidin-5-yl

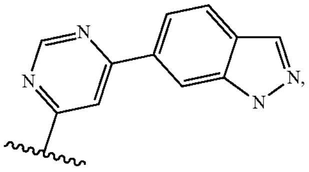

6-(1H-indazol-6-yl)pyrimidin-4-yl

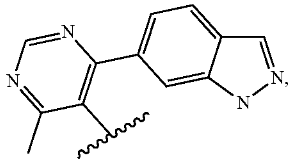

and 6-(1H-indazol-6-yl)-4-methyl-pyrimidin-5-yl

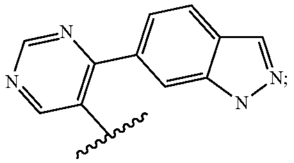

6-(1H-indazol-6-yl)pyrimidin-5-yl covalently bound to a second residue selected from the group consisting of hydrogen, methyl,

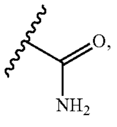
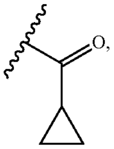
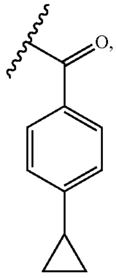
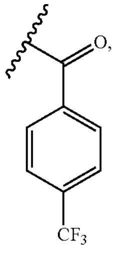

-continued

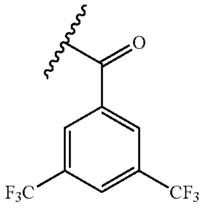

and

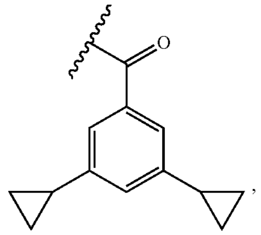

and (ii) a first residue selected from the group consisting of 6-(1,3-benzodioxol-5-yl)-2H-pyrimidin-1-yl, 6-(1,3-benzodioxol-5-yl)-4-methyl-2H-pyrimidin-1-yl, 6-(1H-benzimidazol-5-yl)-2H-pyrimidin-1-yl, 6-(1H-benzimidazol-5-yl)-4-methyl-2H-pyrimidin-1-yl, 6-(1,3-benzodioxol-5-yl)-4,5-dimethyl-2H-pyrimidin-1-yl, 6-(1,3-benzodioxol-5-yl)-5-methyl-2H-pyrimidin-1-yl, 6-(1H-benzimidazol-5-yl)-4,5-dimethyl-2H-pyrimidin-1-yl, 6-(1H-indazol-6-yl)-2H-pyrimidin-1-yl, 6-(1H-indazol-6-yl)-4-methyl-2H-pyrimidin-1-yl, 6-(1H-benzimidazol-5-yl)-5-methyl-2H-pyrimidin-1-yl, 6-(1H-indazol-6-yl)-4,5-dimethyl-2H-pyrimidin-1-yl, 6-(1H-indazol-6-yl)-5-methyl-2H-pyrimidin-1-yl, wherein the 2H-pyrimidine ring is numbered as follows:

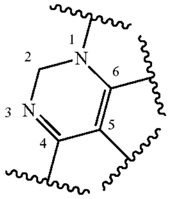

(4R)-3-(1,3-benzodioxol-5-ylmethylcarbamoyl)-4-[[3-(trifluoromethyl)phenyl]methyl-carbamoyl]pyrrolidin-1-yl,
(4R)-3-(1,3-benzodioxol-5-ylmethylcarbamoyl)-4-[[3,5-bis(trifluoromethyl)phenyl]-methylcarbamoyl]pyrrolidin-1-yl,
(4R)-3-(1,3-benzodioxol-5-ylmethylcarbamoyl)-4-[[4-(trifluoromethyl)phenyl]methyl-carbamoyl]pyrrolidin-1-yl,
(4R)-3-(1,3-benzodioxol-5-ylmethylcarbamoyl)-4-[[3-(cyclopropylphenyl)phenyl]-methylcarbamoyl]pyrrolidin-1-yl,
(4R)-3-(1,3-benzodioxol-5-ylmethylcarbamoyl)-4-[[3,5-bis(cyclopropylphenyl)phenyl]-methylcarbamoyl]pyrrolidin-1-yl,
(4R)-3-(1,3-benzodioxol-5-ylmethylcarbamoyl)-4-[[4-(cyclopropylphenyl)phenyl]-methylcarbamoyl]pyrrolidin-1-yl,
(4R)-3-(1H-indazol-5-ylmethylcarbamoyl)-4-[[3-(trifluoromethyl)phenyl]methyl-carbamoyl]pyrrolidin-1-yl,
(4R)-3-(1H-indazol-5-ylmethylcarbamoyl)-4-[[3,5-bis(trifluoromethyl)phenyl]methyl-carbamoyl]pyrrolidin-1-yl,
(4R)-3-(1H-indazol-5-ylmethylcarbamoyl)-4-[[4-(trifluoromethyl)phenyl]methyl-carbamoyl]pyrrolidin-1-yl,
(4R)-3-(1H-indazol-5-ylmethylcarbamoyl)-4-[[3-(cyclopropyl)phenyl]methyl-carbamoyl]pyrrolidin-1-yl,
(4R)-3-(1H-indazol-5-ylmethylcarbamoyl)-4-[[3,5-bis(cyclopropyl)phenyl]methyl-carbamoyl]pyrrolidin-1-yl,
(4R)-3-(1H-indazol-5-ylmethylcarbamoyl)-4-[[4-(cyclopropyl)phenyl]methyl-carbamoyl]pyrrolidin-1-yl, (4R)-3-(3H-benzimidazol-5-ylmethylcarbamoyl)-4-[[3-(trifluoromethyl)phenyl]methyl-carbamoyl]pyrrolidin-1-yl, (4R)-3-(3H-benzimidazol-5-ylmethylcarbamoyl)-4-[[3,5-bis(trifluoromethyl)phenyl]-methylcarbamoyl]pyrrolidin-1-yl, (4R)-3-(3H-benzimidazol-5-ylmethylcarbamoyl)-4-[[4-(trifluoromethyl)phenyl]methyl-carbamoyl]pyrrolidin-1-yl, (4R)-3-(3H-benzimidazol-5-ylmethylcarbamoyl)-4-[[3-(cyclopropyl)phenyl]methyl-carbamoyl]pyrrolidin-1-yl, (4R)-3-(3H-benzimidazol-5-ylmethylcarbamoyl)-4-[[3,5-bis(cyclopropyl)phenyl]methyl-carbamoyl]pyrrolidin-1-yl, (4R)-3-(3H-benzimidazol-5-ylmethylcarbamoyl)-4-[[4-(cyclopropyl)phenyl]methyl-carbamoyl]pyrrolidin-1-yl, (4R)-2-(1,3-benzodioxol-5-yl)-4-[[3-(trifluoromethyl)phenyl]methyl-carbamoyl]pyrrolidin-1-yl, (4R)-2-(1,3-benzodioxol-5-yl)-4-[[3,5-bis(trifluoromethyl)phenyl]methylcarbamoyl]-pyrrolidin-1-yl, (4R)-2-(1,3-benzodioxol-5-yl)-4-[[4-(trifluoromethyl)phenyl]methyl-carbamoyl]pyrrolidin-1-yl, (4R)-2-(1,3-benzodioxol-5-yl)-4-methyl-pyrrolidin-1-yl, (4R)-2-(1,3-benzodioxol-5-yl)-4-[[3-(cyclopropyl)phenyl]methylcarbamoyl]pyrrolidin-1-yl, (4R)-2-(1,3-benzodioxol-5-yl)-4-[[3,5-bis(cyclopropyl)phenyl]methyl-carbamoyl]pyrrolidin-1-yl, (4R)-2-(1,3-benzodioxol-5-yl)-4-[[4-(cyclopropyl)phenyl]methylcarbamoyl]pyrrolidin-1-yl, (4R)-2-(1H-indazol-5-yl)-4-[[3-(trifluoromethyl)phenyl]methyl-carbamoyl]pyrrolidin-1-yl, (4R)-2-(1H-indazol-5-yl)-4-[[3,5-bis(trifluoromethyl)phenyl]methyl-carbamoyl]pyrrolidin-1-yl, (4R)-2-(1H-indazol-5-yl)-4-[[4-(trifluoromethyl)phenyl]methyl-carbamoyl]pyrrolidin-1-yl, (4R)-2-(1H-indazol-5-yl)-3-methyl-pyrrolidin-1-yl, (4R)-2-(1H-indazol-5-yl)-4-[[3-(cyclopropyl)phenyl]methylcarbamoyl]pyrrolidin-1-yl, (4R)-2-(1H-indazol-5-yl)-4-[[3,5-bis(cyclopropyl)phenyl]methyl-carbamoyl]pyrrolidin-1-yl, (4R)-2-(1H-indazol-5-yl)-4-[[4-(cyclopropyl)phenyl]methylcarbamoyl]pyrrolidin-1-yl, (4R)-2-(3H-benzimidazol-5-yl)-4-[[3-(trifluoromethyl)phenyl]methyl-carbamoyl]pyrrolidin-1-yl, (4R)-2-(3H-benzimidazol-5-yl)-4-[[3,5-bis(trifluoromethyl)phenyl]methylcarbamoyl]-pyrrolidin-1-yl, (4R)-2-(3H-benzimidazol-5-yl)-4-[[4-(trifluoromethyl)phenyl]methyl-carbamoyl]pyrrolidin-1-yl, (4R)-2-(3H-benzimidazol-5-yl)-3-methyl-pyrrolidin-1-yl, (4R)-2-(3H-benzimidazol-5-yl)-4-[[3-(cyclopropyl)phenyl]methylcarbamoyl]pyrrolidin-1-yl, (4R)-2-(3H-benzimidazol-5-yl)-4-[[3,5-bis(cyclopropyl)phenyl]methyl-carbamoyl]pyrrolidin-1-yl, (4R)-2-(3H-benzimidazol-5-yl)-4-[[4-(cyclopropyl)phenyl]methylcarbamoyl]pyrrolidin-1-yl, (4R)-2-(1,3-benzodioxol-5-yl)-3-methyl-4-[[3-(trifluoromethyl)phenyl]methyl-carbamoyl]pyrrolidin-1-yl, (4R)-2-(1,3-benzodioxol-5-yl)-3-methyl-4-[[3,5-bis(trifluoromethyl)phenyl]methyl-carbamoyl]pyrrolidin-1-yl, (4R)-2-(1,3-benzodioxol-5-yl)-3-methyl-4-[[4-(trifluoromethyl)phenyl]methyl-carbamoyl]pyrrolidin-1-yl, (4R)-2-(1,3-benzodioxol-5-yl)-3-methyl-pyrrolidin-1-yl, (4R)-2-(1,3-benzodioxol-5-yl)-3-methyl-4-[[3-(cyclopropyl)phenyl]methyl-carbamoyl]pyrrolidin-1-yl, (4R)-2-(1,3-benzodioxol-5-yl)-3-methyl-4-[[3,5-bis(cyclopropyl)phenyl]methyl-carbamoyl]pyrrolidin-1-yl, (4R)-2-(1,3-benzodioxol-5-yl)-3-methyl-4-[[4-(cyclopropyl)phenyl]methyl-carbamoyl]pyrrolidin-1-yl, (4R)-2-(1H-indazol-6-yl)-3-methyl-4-[[3-(trifluoromethyl)phenyl]methyl-carbamoyl]pyrrolidin-1-yl, (4R)-2-(1H-indazol-6-yl)-3-methyl-4-[[3,5-bis(trifluoromethyl)phenyl]methyl-carbamoyl]pyrrolidin-1-yl, (4R)-2-(1H-indazol-6-yl)-3-methyl-4-[[4-(trifluoromethyl)phenyl]methyl-carbamoyl]pyrrolidin-1-yl, (4R)-2-(1H-indazol-6-yl)-3-methyl-pyrrolidin-1-yl (4R)-2-(1H-indazol-6-yl)-3-methyl-4-[[3-(cyclopropyl)phenyl]methyl-carbamoyl]pyrrolidin-1-yl, (4R)-2-(1H-indazol-6-yl)-3-methyl-4-[[3,5-bis(cyclopropyl)phenyl]methyl-carbamoyl]pyrrolidin-1-yl, (4R)-2-(1H-indazol-6-yl)-3-methyl-4-[[4-(cyclopropyl)phenyl]methyl-carbamoyl]pyrrolidin-1-yl, (4R)-2-(1H-benzimidazol-5-yl)-4-[[3-(trifluoromethyl)phenyl]methyl-carbamoyl]pyrrolidin-1-yl, (4R)-2-(1H-benzimidazol-5-yl)-4-[[3,5-bis(trifluoromethyl)phenyl]methyl-carbamoyl]pyrrolidin-1-yl, (4R)-2-(1H-benzimidazol-5-yl)-4-[[4-(trifluoromethyl)phenyl]methyl-carbamoyl]pyrrolidin-1-yl, (4R)-2-(1H-benzimidazol-5-yl)-3-methyl-pyrrolidin-1-yl, (4R)-2-(1H-benzimidazol-5-yl)-4-[[3-(cyclopropyl)phenyl]methylcarbamoyl]pyrrolidin-1-yl, (4R)-2-(1H-benzimidazol-5-yl)-4-[[3,5-bis(cyclopropyl)phenyl]methyl-carbamoyl]pyrrolidin-1-yl, and (4R)-2-(1H-benzimidazol-5-yl)-4-[[4-(cyclopropyl)phenyl]methylcarbamoyl]pyrrolidin-1-yl, wherein the pyrrolidine ring is numbered as follows:

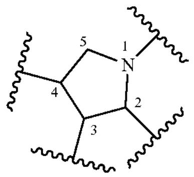
;

covalently bound to a second residue selected from the group consisting of hydrogen, methyl,

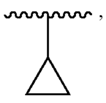
,
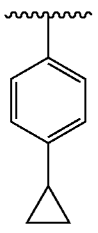
,
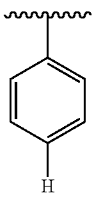
,
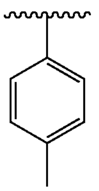
,
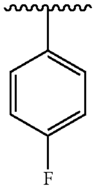
,
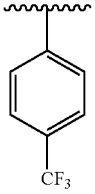
and
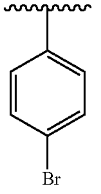
, wherein the first residue is covalently bound to the second residue at the -yl position of the first residue;

preferably a compound selected from the group consisting of

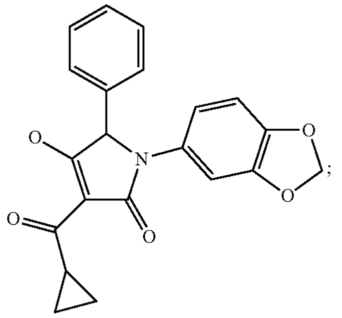

1-(1,3-benzodioxol-5-yl)-4-(cyclopropanecarbonyl)-3-hydroxy-2-phenyl-2H-pyrrol-5-one

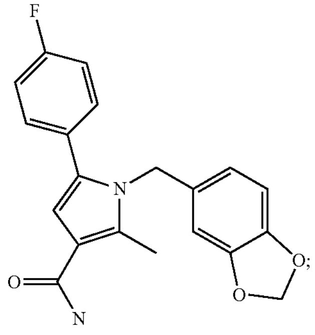

1-(1,3-benzodioxol-5-ylmethyl)-5-(4-fluorophenyl)-2-methyl-pyrrole-3-carboxamide

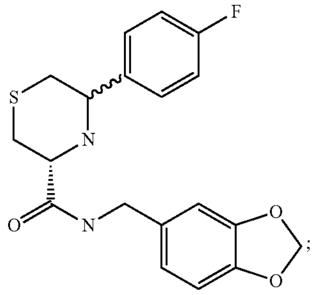

(3R)-N-(1,3-benzodioxol-5-ylmethyl)-5-(4-fluorophenyl)thiomorpholine-3-carboxamide

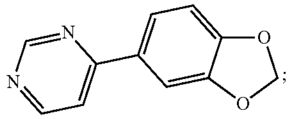

4-(1,3-benzodioxol-5-yl) pyrimidine

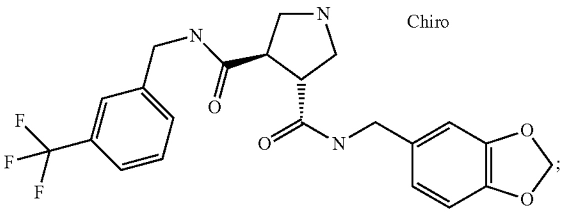

(4R)-N3-(1,3-benzodioxol-5-ylmethyl)-N4-[[3-(trifluoromethyl)phenyl]methyl] pyrrolidine-3,4-dicarboxamide -continued

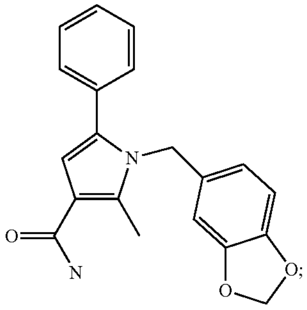

1-(1,3-benzodioxol-5-ylmethyl)-2-methyl-5-phenyl-pyrrole-3-carboxamide

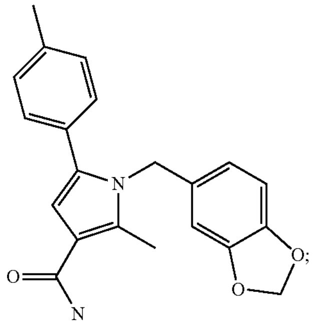

and 1-(1,3-benzodioxol-5-ylmethyl)-2-methyl-5-(p-tolyl)pyrrole-3-carboxamide

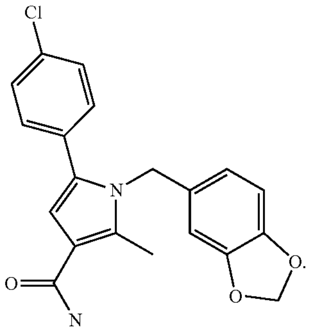

1-(1,3-benzodioxol-5-ylmethyl)-5-(4-chlorophenyl)-2-methyl-pyrrole-3-carboxamide In a further aspect, the present invention is directed to a compound selected from the group consisting of

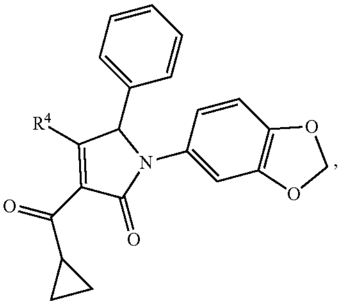

wherein $R^4$ is selected from the group consisting of hydroxyl, —O—$R^{14}$, and —O—C(═O)—$R^{14}$, wherein $R^{14}$ is selected from the group consisting of (aa) linear or branched, substituted or non-substituted $(C_{1-10})$alkyl, preferably $(C_{1-5})$alkyl, more preferably methyl, ethyl and propyl, most preferably methyl, $(C_{2-10})$alkenyl, and $(C_{2-10})$alkynyl;

(bb) substituted or non-substituted aromatic or non-aromatic $(C_{3-10})$carbocycle, preferably $(C_{3-6})$cycloalkyl, more preferably $(C_3)$carbocycle and $(C_6)$carbocycle, preferably $(C_6)$carbocycle, more preferably phenyl that is mono-substituted in para position by $(C_3)$carbocycle or —$(CF_3)$ or di-substituted in meta position by $(C_3)$ carbocycle or —$(CF_3)$; and (cc) substituted or non-substituted aromatic or non-aromatic, preferably aromatic, $(C_{3-6})$heterocycle having 1 to 3 heteroatoms each independently selected from N, O and S;

preferably a compound selected from the group consisting of

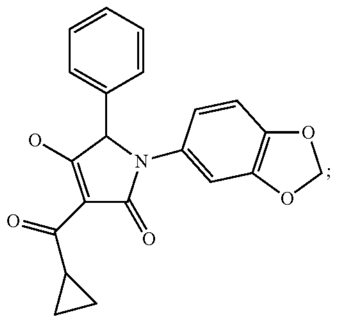

1-(1,3-benzodioxol-5-yl)-4-(cyclopropanecarbonyl)-3-hydroxy-2-phenyl-2H-pyrrol-5-one

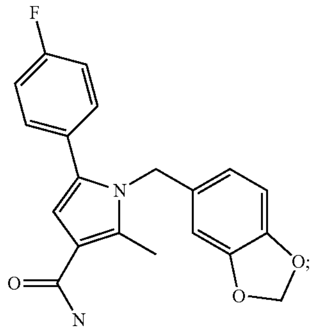

1-(1,3-benzodioxol-5-ylmethyl)-5-(4-fluorophenyl)-2-methyl-pyrrole-3-carboxamide

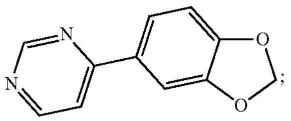

and 4-(1,3-benzodioxol-5-yl) pyrimidine

-continued

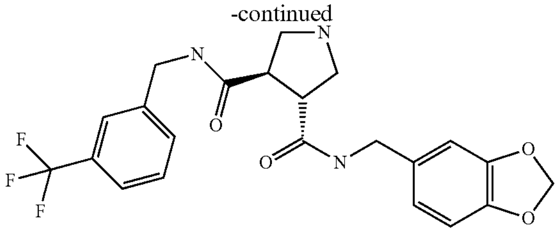

(4R)-N3-(1,3-benzodioxol-5-ylmethyl)-N4-[[3-(trifluoromethyl)phenyl]methyl] pyrrolidine-3,4-dicarboxamide for use according to the present invention.

The compounds described herein are generally named by using the nomenclature that was computed based on the structural drawings by the software ACD/Chemsketch 2015 provided by Advanced Chemistry Development, Inc., Canada and BIOVIA Draw 2016 provided by BIOVIA, USA. For each molecule described herein, the description provides a structural formula that unam-biguously numbers the residues of the rings of Formula I and II for the purposes of nomenclature. It is further noted that the structural formulae are binding and not the computed chemical names; in other words, if the name and the structural formula contradict each other, the structural formula prevails.

For compounds having asymmetric centers, it is understood that, unless otherwise specified, all of the optical isomers and mixtures thereof are encompassed. Each stereogenic carbon may be in the (R)- or (S)-configuration or a combination of configurations if not indicated differently. Also, compounds with two or more asymmetric elements can be present as mixtures of diastereomers. Furthermore, the compounds of the present invention preferably have a diastereomeric purity of at least 50%, preferably at least 60%, 70%, 80%, 85%, more preferably at least 90%, 95%, 96%, 97%, most preferably at least 98%, 99% or 100%. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms.

For example, the compound depicted as follows:

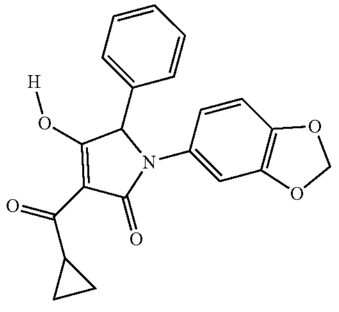 [SMILES: O=C(C1=C(O)C(c2ccccc2)N(c2ccc3c(c2)OCO3)C1=O)C1CC1]

encompasses the tautomeric form:

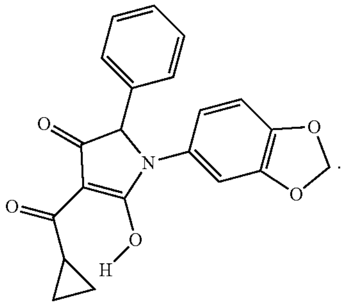 [SMILES: O=C(C1=C(O)N(c2ccc3c(c2)OCO3)C(c2ccccc2)C1=O)C1CC1]

Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}C$, $^{13}C$, and $^{14}C$.

Compounds according to the formulas provided herein, which have one or more stereogenic center(s), have an enantiomeric excess of at least 50%. For example, such compounds may have an enantiomeric excess of at least 60%, 70%, 80%, 85%, preferably at least 90%, 95%, or 98%. Some embodiments of the compounds have an enantiomeric excess of at least 99%. It will be apparent that single enantiomers (optically active forms) can be obtained by asymmetric synthesis, synthesis from optically pure precursors, biosynthesis, e.g. using modified CYP102 (CYP BM-3) or by resolution of the racemates, e.g. enzymatic resolution or resolution by conventional methods such as crystallization in the presence of a resolving agent, or chromatography, using, for example, a chiral HPLC column.

As used herein, a "substituent" or "residue" or "R", refers to a molecular moiety that is covalently bound to an atom within a molecule of interest. For example, a "substituent", "R" or "residue" may be a moiety such as a halogen, alkyl group, haloalkyl group or any other substituent described herein that is covalently bonded to an atom, preferably a carbon or nitrogen atom, that forms part of a molecule of interest. The term "substituted" as used herein, means that any one or more hydrogens on the designated atom is replaced with a different atom than hydrogen, preferably by a halogen, more preferably by fluorine or by a selection from the indicated substituents, provided that the designated atom's normal valence is not exceeded, and that the substitution results in a stable compound, i.e., a compound that can be isolated and characterized using conventional means. For example, substitution can be in the form of an oxygen bound to any other chemical atom than carbon, e.g. hydroxyl group, or an oxygen anion. When a substituent is oxo, i.e., =O, then 2 hydrogens on the atom are replaced. An oxo group that is a substituent of an aromatic carbon atom results in a conversion of —CH— to —C(=O)— and a loss of aromaticity. For example, a pyridyl group substituted by oxo is a pyridone.

The term "heteroatom" as used herein shall be understood to mean atoms other than carbon and hydrogen such as and preferably O, N, S and P.

If a first compound, a substituent or a residue ends, e.g., in the name "-3-yl", this ending indicates that the first compound, substituent or residue is covalently bound to a second compound, substituent or residue at the atom number 3 position of the first compound. Of course, this definition holds true for any given integer before the "-yl" terminus of the compound's, substituent's or residue's name. For example, if 1-(1,3-benzodioxol-5-ylmethyl)pyrrol-3-yl is selected as a first residue to be covalently bound to the second residue

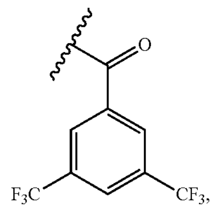

the following compound is formed:

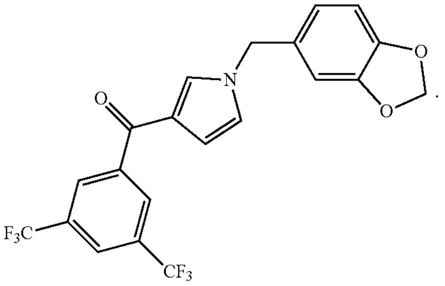 [SMILES: O=C(c1cc(C(F)(F)F)cc(C(F)(F)F)c1)c1ccn(Cc2ccc3c(c2)OCO3)c1]

In the context of the present invention it is understood that antecedent terms such as "linear or branched", "substituted or non-substituted" indicate that each one of the subsequent terms is to be interpreted as being modified by said antecedent term. For example, the scope of the term "linear or branched, substituted or non-substituted alkyl, alkenyl, alkynyl, carbocycle" encompasses linear or branched, substituted or non-substituted alkyl; linear or branched, substituted or non-substituted alkenyl; linear or branched, substituted or non-substituted alkynyl; linear or branched, substituted or non-substituted alkylidene; and linear or branched, substituted or non-substituted carbocycle. For example, the term "($C_{2-10}$) alkenyl, alkynyl or alkylidene" indicates the group of compounds having 2 to 10 carbons and alkenyl, alkynyl or alkylidene functionality.

The expression "alkyl" refers to a saturated, straight-chain or branched hydrocarbon group that contains the number of carbon items indicated, e.g. "($C_{1-10}$)alkyl" denotes a hydrocarbon residue containing from 1 to 10 carbon atoms, e.g. a methyl, ethyl, propyl, iso-propyl, n-butyl, iso-butyl, sec-butyl, tert-butyl, n-pentyl, iso-pentyl, n-hexyl, 2,2-dimethylbutyl, etc.

The expression "alkenyl" refers to an at least partially unsaturated, substituted or non-substituted straight-chain or branched hydrocarbon group that contains the number of carbon atoms indicated, e.g. "($C_{2-10}$)alkenyl" denotes a hydrocarbon residue containing from 2 to 10 carbon atoms, for example an ethenyl (vinyl), propenyl (allyl), iso-propenyl, butenyl, isoprenyl or hex-2-enyl group, or, for example, a hydrocarbon group comprising a methylene chain interrupted by one double bond as, for example, found in monounsaturated fatty acids or a hydrocarbon group comprising methylene-interrupted polyenes, e.g. hydrocarbon groups comprising two or more of the following structural unit $-[CH=CH-CH_2]-$, as, for example, found in polyunsaturated fatty acids. Alkenyl groups have one or more, preferably 1, 2, 3, 4, 5, or 6 double bond(s).

The expression "alkynyl" refers to at least partially unsaturated, substituted or non-substituted straight-chain or branched hydrocarbon groups that contain the number of carbon items indicated, e.g. "$(C_{2-10})$alkynyl" denotes a hydrocarbon residue containing from 2 to 10 carbon atoms, for example an ethinyl, propinyl, butinyl, acetylenyl, or propargyl group. Preferably, alkynyl groups have one or two (especially preferably one) triple bond(s).

Furthermore, the terms "alkyl", "alkenyl" and "alkynyl" also refer to groups in which one or more hydrogen atom(s) have been replaced, e.g. by a halogen atom, preferably F, Cl or Br, such as, for example, a 2,2,2-trichloroethyl, tribromoethyl or a trifluoromethyl group.

The term "carbocycle" shall be understood to mean a substituted or non-substituted aliphatic hydrocarbon cycle containing the number of carbon items indicated, e.g. "$(C_{3-10})$carbocycle" or from 3 to 20, preferably from 3 to 12 carbon atoms, more preferably 5 or 6 carbon atoms. These carbocycles may be either aromatic or non-aromatic systems. The non-aromatic ring systems may be mono- or polyunsaturated.

The term "carbobicycle" refers to a carbocycle as defined above comprising more than 1 ring, preferably two rings. Preferred carbocycles and carbobicycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl, benzocycloheptenyl, spiro[4,5]decanyl, norbornyl, decalinyl, bicyclo[4.3.0]nonyl, tetraline, or cyclopentylcyclohexyl. The carbo- and/or carbobicyclic residue may be bound to the remaining structure of the complete molecule by any atom of the cycle, which results in a stable structure The term "carbocycle" shall also include "cycloalkyl" which is to be understood to mean aliphatic hydrocarbon-containing rings preferably having from 3 to 12 carbon atoms. These non-aromatic ring systems may be mono- or polyunsaturated, i.e. the term encompasses cycloalkenyl and cycloalkynyl.

The term "heterocycle" refers to a stable substituted or non-substituted, aromatic or non-aromatic, preferably 3 to 20 membered, more preferably 3-12 membered, most preferably 5 or 6 membered, monocyclic, heteroatom-containing cycle. Each heterocycle consists of carbon atoms and one or more, preferably 1 to 4, more preferably 1 to 3 heteroatoms preferably chosen from nitrogen, oxygen and sulphur. A heterocycle may contain the number of carbon atoms in addition to the non-carbon atoms as indicated: a "$(C_{3-6})$ heterocycle" is meant to have 3 to 6 carbon atoms in addition to a given number of heteroatoms.

The term "heterobicycle" refers to a heterocycle as defined above comprising more than 1 ring, preferably two rings.

The hetero- and/or heterobicyclic residue may be bound to the remaining structure of the complete molecule by any atom of the cycle, which results in a stable structure. Exemplary heterocycles and heterobicycles include, but are not limited to pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, 1-oxo-X4-thiomorpholinyl, 13-oxa-11-aza-tricyclo [7.3.1.0-2,7]tridecy-2,4,6-triene, tetrahydropyranyl, 2-oxo-2H-pyranyl, tetrahydrofuranyl, 1,3-dioxolanone, 1,3-dioxanone, 1,4-dioxanyl, 8-oxa-3-aza-bicyclo[3.2.1] octanyl, 2-oxa-5-aza-bicyclo[2.2.1]heptanyl, 2-thia-5-aza-bicyclo[2.2.1]heptanyl, piperidinonyl, tetrahydropyrimidonyl, pentamethylene sulphide, pentamethylene sulfoxide, pentamethylene sulfone, tetramethylene sulphide, tetramethylene sulfoxide and tetramethylene sulfone, indazolyl, benzimidazolyl, benzodioxolyl, imidazolyl, 1,3-benzodioxolyl and pyrazolyl.

The expressions "alkyl/alkenyl/alkynyl ether" refer to a saturated or non-saturated, straight-chain or branched hydrocarbon group that contains the number of carbon items indicated. For example, "$(C_{1-10})$alkyl ether" denotes a hydrocarbon residue containing from 1 to 10 carbon atoms, and any suitable number of oxygen atoms that will result in an ether structure. Alkyl/alkenyl/alkynyl ether groups as used herein shall be understood to mean any linear or branched, substituted or non-substituted alkyl/alkenyl/alkynyl chain comprising an oxygen atom either as an ether motif, i.e. an oxygen bound by two carbons. The ether residue can be attached to the Formulas provided in the present invention either via the carbon atom or via the oxygen atom of the ether residue.

The "substituent" or "residue" or "R" as used herein, preferably $R^2$, $R^3$, $R^4$, $R^5$, $R^6$, $R^7$, $R^8$, $R^9$, $R^{10}$ and/or $R^{11}$ can be attached directly to the Formulas provided in the present invention or by means of a linker. Said linker can also be in the form of polyethyleneglycol. The term polyethyleneglycol as used herein refers to a chain of substituted or non-substituted ethylene oxide monomers.

As used herein, the terms "nitrogen" or "N" and "sulphur" or "S" include any oxidized form of nitrogen and sulphur and the quaternized form of any basic nitrogen as long as the resulting compound is chemically stable. For example, for an $-S-C_{1-6}$ alkyl radical shall be understood to include $-S(O)-C_{1-6}$alkyl and $-S(O)_2-C_{1-6}$ alkyl.

A residue connected via a given position to a second compound of interest is to be understood as a residue that is covalently bound to the second compound at the atom position indicated. For example, indazolyl connected via position (5) of the indazolyl denotes the following residue:

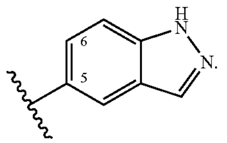 [SMILES: *c1ccc2[nH]ncc2c1]

In this case, the numbering starts—as customary in the art—on the 1H-nitrogen. However, it is noted that some nomenclature may provide a different starting point for the numbering. For example, a 1H-benzimidazol-6-yl residue is identical to a 3H-benzimidazol-5-yl residue, as is understood by the skilled person.

As used herein, a wording defining the limits of a range of length such as, e. g., "from 1 to 5" or "$(C_{1-5})$" means any integer from 1 to 5, i. e. 1, 2, 3, 4 and 5. In other words, any range defined by two integers explicitly mentioned is meant to comprise and disclose any integer defining said limits and any integer comprised in said range.

By way of example, the term "mono- or di-substituted in meta position or mono-substituted in para position", as used herein, means that a compound is either substituted by at least one given substituent in para position to the position where the compound is attached to another compound or residue, or substituted in two of its meta positions by at least one substituent. For example, the term "di-substituted in meta position by $(C_3)$carbocycle or $-(CF_3)$" denotes that a compound is substituted by one $(C_3)$carbocycle or $-(CF_3)$ in each meta position or by a ($C_3$)carbocycle in one meta position and by —($CF_3$) in the other meta position. Preferably, the term denotes that a compound is substituted by one ($C_3$)carbocycle in each meta position or by one —($CF_3$) in each meta position, i.e. is substituted in both meta positions by the same substituent. As denoted above for the para position, the meta position denotes the position meta to the position where the compound is attached to another compound or residue.

As an example, the term "phenyl, preferably mono-substituted in para or meta position by cyclopropyl or —($CF_3$), or di-substituted in meta position by cyclopropyl or —($CF_3$) in each meta position" preferably denotes the following structures:

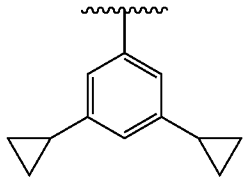,
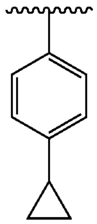,
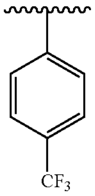
and
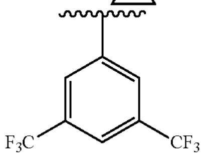

The residues $R^1$, $R^5$ and/or $R^9$ for use in the present invention are preferably phenyl that is mono-substituted in para position by a group consisting of Cl, F, Br, substituted or non-substituted methyl, preferably —($CF_3$), ethyl, propyl and cyclopropyl. The residues $R^{12}$ and $R^{13}$ for use in the present invention are preferably ($C_6$)carbocycle, more preferably phenyl that is mono-substituted in para position by a ($C_3$)carbocycle, preferably cyclopropyl, or —($CF_3$), or di-substituted in meta position by ($C_3$)carbocycle, preferably cyclopropyl, or (—$CF_3$). It is further preferred that $R^1$, $R^5$, $R^9$, $R^{12}$ and/or $R^{13}$ are phenyl that is mono-, di- or tri-substituted in ortho, meta and/or para position by a group consisting of Cl, F, Br, substituted or non-substituted methyl, preferably —($CF_3$), ethyl, propyl and cyclopropyl. The di- or tri-substituted phenyl representing $R^1$, $R^5$, $R^9$, $R^{12}$ and/or $R^{13}$ can be di- or tri-substituted phenyl that is substituted with the same substituent in the respective ortho, meta and para position or by different substituents in the respective ortho, meta and/or para position, wherein the substituents are selected from the group consisting of Cl, F, Br, substituted or non-substituted methyl, preferably —($CF_3$), ethyl, propyl and cyclopropyl. Each combination and number of substituents selected from the group consisting of Cl, F, Br, substituted or non-substituted methyl, preferably —($CF_3$), ethyl, propyl and cyclopropyl in ortho, meta and/or para position of the phenyl representing $R^1$, $R^5$, $R^9$, $R^{12}$ and/or $R^{13}$ is explicitly disclosed herein.

The scope of the present invention includes those analogs of the compounds as described above and in the claims that feature the exchange of one or more carbon-bonded hydrogens, preferably one or more aromatic carbon-bonded hydrogens, with halogen atoms such as F, Cl, or Br, preferably F. The exchange of one or more of the carbon-bonded hydrogens, e.g. by fluorine, can be done, e.g., for reasons of metabolic stability and/or pharmacokinetic and physicochemical properties, as shown in the Examples below, in particular Examples 5 to 13 and the corresponding conclusion. For example, Compound-1 can feature one or more halogen atoms, preferably F, instead of the aromatic carbon-bonded hydrogens in the phenyl ring or instead of the aromatic or non-aromatic carbon-bonded hydrogens in the 1,3-benzodioxol-5-yl-moiety. Also, for example, Compound-4 can feature one or more halogen atoms, preferably F, instead of the aromatic carbon-bonded hydrogens in the pyrimidine ring or instead of the aromatic or non-aromatic carbon-bonded hydrogens in the benzodioxole moiety.

Exemplary preferred analogs of Compounds 1, 1F and 4 as such and for use in all aspects of the present invention include the following:

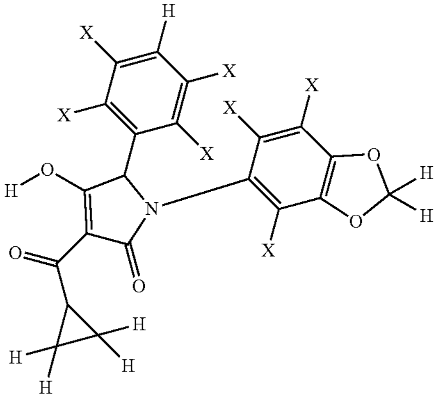

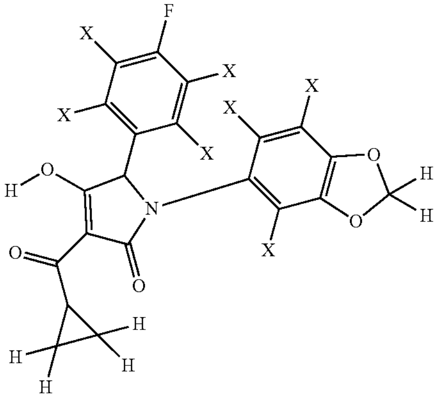

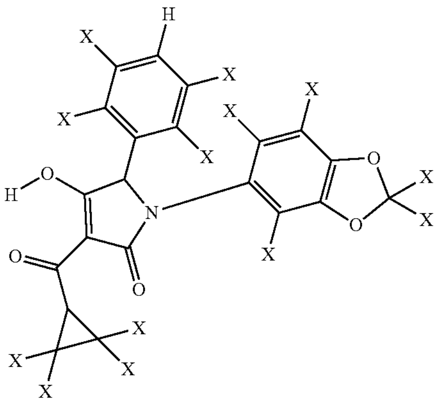

-continued

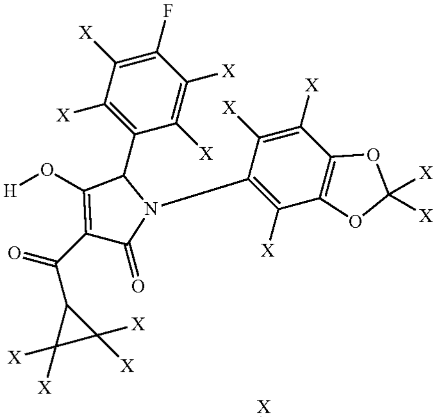

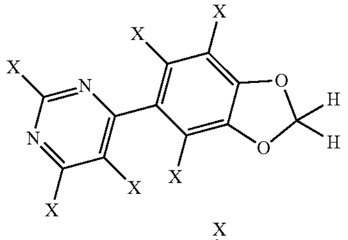

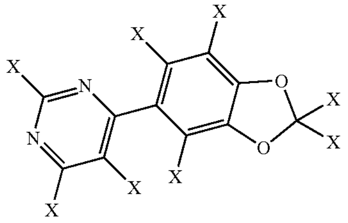

wherein X denotes hydrogen or halogen, preferably fluorine in all possible permutations.

In a preferred embodiment, the present invention is directed to a herein-described compound for use as described herein, wherein the compound inhibits the PHF (paired helical filament) Tau hyperphosphorylation, preferably also inhibits phosphorylation of the serine/arginine-rich splicing factor 1 (SRSF1, ASF-1, SF2) by a kinase, preferably by the G-protein-coupled receptor kinase 2 (GRK2, ADRBK1), more preferably also inhibits the formation and/or accumulation of Abeta peptides and Abeta plaques, more preferably also inhibits neurodegeneration and/or neuronal loss, preferably hippocampal neuronal loss.

The herein observed neuroprotective and anti-ageing activity of the GRK2-inhibitory compounds could involve inhibition of mitochondrial dysfunction, which is supported by a previous study, which demonstrates that the active GRK2 induces mitochondrial dysfunction (Sato et al., J. Mol. Cell. Cardiol. 89, 360-364 (2015)). Notably, neurodegeneration and ageing are triggered and aggravated by mitochondrial dysfunction (Lin and Beal, Nature 443, 787-795 (2006)). In addition, inhibition of GRK2-mediated activating SRSF1 phosphorylation by the herein described compounds (as described in the related patent application WO/2018/130537 (PCT/EP2018/050504) could also contribute to inhibition of neurodegeneration and ageing because activated SRSF1 promotes aberrant prelamin A (LMNA) mRNA splicing, which accounts for a phenotype of accelerated ageing, and mitochondrial dysfunction (Harhouri et al., EMBO Mol. Med. 9, 1294-1313 (2017); Gonzalo et al., Ageing Res. Rev. 33, 18-29 (2017)).

In another aspect, the present invention is directed to a pharmaceutical composition, comprising as active substance a compound for use as described herein or a pharmaceutically acceptable derivative thereof, optionally combined with excipients and/or carriers.

The invention includes pharmaceutically acceptable salts or solvates of the compounds of Formula (I) and (II) of the present invention. A "pharmaceutically acceptable salt or solvate" refers to any pharmaceutically acceptable salt, solvate or ester or any other compound which, upon administration to a patient, is capable of providing (directly or indirectly) a compound of the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the present invention.

Pharmaceutically acceptable salts include those derived from pharmaceutically acceptable inorganic and organic acids and bases. Examples of suitable acids include hydrochloric, hydrobromic, sulphuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g. magnesium), ammonium and N—$(C_1\text{-}C_4alkyl)_4^+$ salts.

In addition, the scope of the invention also encompasses prodrugs of compounds of the present invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

In a preferred embodiment, the compounds for use in the present invention are for use in the treatment of CNS- and neurodegenerative diseases selected from the group consisting of dementia-associated CNS- and neurodegenerative disorders, CNS- and neurodegenerative disease-associated schizophrenia with dementia, psychiatric disorders, preferably Alzheimer's disease, schizophrenia, mood and anxiety disorders, behavioral disorders, preferably anorexia nervosa and substance use disorder; depression-associated CNS- and neurodegenerative disorders, preferably depression and depression-related symptoms, preferably anhedonia and anorexia, and muscle wasting, brain injury, preferably traumatic brain injury, cerebrovascular disease-induced neurodegeneration, preferably ischemic stroke-induced neurodegeneration, hypertension-induced neurodegeneration, atherosclerosis-induced neurodegeneration, amyloid angiopathy-induced neurodegeneration, preferably small-vessel cerebrovascular disease, motor neuron disease, ALS (amyotrophic lateral sclerosis), multiple sclerosis, familial and sporadic forms of Alzheimer's Disease, vascular dementia, Morbus Parkinson, chromosome-17-linked Morbus Parkinson, frontotemporal dementia, Korsakoff's psychosis, Lewy Body diseases, progressive supranuclear palsy, corticobasal degeneration, Pick's disease, Huntington's disease, thalamic degeneration, prion-associated diseases, preferably Creutzfeld-Jacob disease, HIV-associated dementia, diabetes-induced neuropathy, neurodegenerative symptoms of ageing, preferably loss of appetite or greying of hair, and the decline of male and female fertility, cognitive-related disorders, mild cognitive impairment, age-associated memory impairment, age-associated cognitive decline, vascular cognitive impairment, central and peripheral neuronal symptoms of atherosclerosis and ischemia, stress-related CNS- and neurodegenerative disorders, attention deficit disorders, attention deficit hyperactivity disorders, memory disturbances in children, and progeria infantilis;

Preferably, the compound or pharmaceutical composition as described herein is for use in the treatment of animals or humans, more preferably mammalians, most preferably humans.

All the above-mentioned diseases and disorders are associated with CNS- and/or neurodegenerative symptoms. For example, prolonged stress and depression are both associated with CNS- and neurodegeneration. The same, stress and ageing can lead to CNS- and/or neurodegenerative symptoms such as age/stress-associated memory impairment, age/stress-associated cognitive decline, age/stress-related loss of appetite, age/stress-associated greying of hair, and also the age/stress-related decline of male and female fertility. In the experimental section below it is demonstrated in a representative rodent model of stress, ageing and depression that oral administration of the compounds disclosed herein can actually increase appetite and the preference for sucrose consumption as important indicators for beneficial treatment effects against, e.g., psychiatric disorders (e.g. Alzheimer's disease, schizophrenia, mood and anxiety disorders) and behavioral disorders (e.g. anorexia nervosa and substance use disorder). It is also demonstrated in a rodent model that oral administration of the compounds disclosed herein can retard the aging-induced decline of male and female fertility. The decline of male and female fertility is one of the best-established indicators of aging. Notably, oral treatment with compounds disclosed herein can also lead to an increased sperm vitality and mobility, and significantly retards the aging-induced decline of sperm vitality and mobility in males. In addition, disclosed compounds can retard the aging-induced fertility decline in females.

As commonly used, the term treatment encompasses the actual therapeutic treatment of an existing disease as well as the prophylactic, i.e. preventive treatment of a future disease.

In a preferred embodiment, the present invention relates to compounds for the therapeutic and/or prophylactic treatment of CNS- and neurodegenerative diseases selected from the group consisting of i. therapeutic treatment of CNS- and neurodegenerative disease-associated dementia;
ii. therapeutic treatment of CNS- and neurodegenerative disease-associated depression;
iii. therapeutic treatment of brain injury, preferably traumatic brain injuries;
iv. therapeutic and prophylactic treatment of cerebrovascular diseases-induced neurodegeneration (i.e. ischemic stroke-induced neurodegeneration, hypertension-induced neurodegeneration, atherosclerosis-induced neurodegeneration, amyloid angiopathy-induced neurodegeneration) and preferably small-vessel cerebrovascular disease;
V. therapeutic treatment of motor neuron disease;
vi. therapeutic treatment of ALS;
vii. therapeutic treatment of multiple sclerosis;
viii. therapeutic and prophylactic treatment of familial and sporadic forms of Alzheimer's Disease;
ix. therapeutic treatment of CNS- and neurodegenerative disease-associated vascular dementia;
x. therapeutic treatment of CNS- and neurodegenerative disease-associated frontotemporal dementia;
xi. therapeutic and prophylactic treatment of Morbus Parkinson, preferably chromosome-17-linked Morbus Parkinson;
xii. therapeutic and prophylactic treatment of symptoms of depression and depression-related symptoms, preferably anhedonia and anorexia, and muscle wasting;
xiii. therapeutic and prophylactic treatment of psychiatric disorders, preferably AD, schizophrenia, mood and anxiety disorders, and behavioral disorders, preferably anorexia nervosa and substance use disorder, and symptoms associated with these disorders;
xiv. therapeutic treatment of CNS- and neurodegenerative disease-associated schizophrenia with dementia;
xv. therapeutic treatment of Korsakoff's psychosis;
xvi. therapeutic treatment of Lewy Body diseases;
xvii. therapeutic treatment of progressive supranuclear palsy;
xviii. therapeutic treatment of corticobasal degeneration;
xix. therapeutic treatment of Pick's disease;
xx. therapeutic treatment of Huntington's disease;
xxi. therapeutic treatment of CNS- and neurodegenerative disease-associated thalamic degeneration;
xxii. therapeutic treatment of prion diseases, preferably Creutzfeld-Jacob disease;
xxiii. therapeutic treatment of HIV-associated dementia;
xxiv. therapeutic and prophylactic treatment of diabetes-induced neuropathy;
xxv. therapeutic and prophylactic treatment of CNS- and/or neurodegeneration-associated symptoms such as age/stress-associated memory impairment, age/stress-associated cognitive decline, age/stress-related loss of appetite, and age/stress-associated greying of hair;
xxvi. therapeutic and prophylactic treatment of age/stress-related decline of male and female fertility;
xxvii. therapeutic and prophylactic treatment of cognitive-related disorder;
xxviii. therapeutic and prophylactic treatment of mild cognitive impairment;
xxix. therapeutic and prophylactic treatment of vascular cognitive impairment;
xxx. therapeutic and prophylactic treatment of central and peripheral symptoms of atherosclerosis and ischemia;
xxxi. therapeutic and prophylactic treatment of perivascular disease;
xxxii. prophylaxis against renal dysfunction and renal failure;
xxxiii. therapeutic and prophylactic treatment of stress-related disorders;
xxxiv. therapeutic and prophylactic treatment of attention deficit disorders;
xxxv. therapeutic and prophylactic treatment of attention deficit hyperactivity disorders;
xxxvi. therapeutic and prophylactic treatment of memory disturbances in children, and wherein the compound or pharmaceutical composition is for use in the treatment of animals or humans, preferably mammalians, more preferably humans.

In a more preferred embodiment, the present invention relates to compounds for use in the treatment of CNS- and neurodegenerative diseases selected from the group consisting of i. therapeutic and prophylactic treatment of familial and sporadic forms of Alzheimer's Disease;

ii. therapeutic and prophylactic treatment of diabetes-induced neuropathy, preferably diabetes type 2;
iii. therapeutic and prophylactic treatment of dementias associated with neurodegeneration;
iv. therapeutic and prophylactic treatment of low sperm quality and vitality and erectile dysfunction in men, and low fertility in women;
v. therapeutic and prophylactic treatment of psychiatric disorders, preferably AD, schizophrenia, mood and anxiety disorders, and behavioral disorders, preferably anorexia nervosa and substance use disorder, and symptoms associated with these disorders;
vi. therapeutic and prophylactic treatment of low appetite, symptoms of anorexia, and muscle wasting;
vii. therapeutic and prophylactic treatment of tauopathies;
viii. therapeutic and prophylactic treatment of Morbus Parkinson.

In a further preferred embodiment, the present invention is directed to compounds according to Formula IIb, wherein X is N and Y is C, preferably Compound-4, for use in the treatment of psychiatric symptoms of anorexia, low appetite and/or muscle wasting.

In a further preferred embodiment, the present invention is directed to compounds according to Formula IIb, wherein X is N and Y is C, preferably Compound-4, and compounds according to Formula Ia, preferably Compound-1 and Compound-1F, for use in the therapeutic and/or prophylactic treatment of psychiatric disorders, preferably Alzheimer's disease, schizophrenia, mood and anxiety disorders, and behavioral disorders, preferably anorexia nervosa and substance use disorder, and symptoms associated with these disorders. Notably, all these psychiatric disorders are characterized by symptoms of neurodegeneration (Archer T, Expert Rev. Neurother. 10, 1131-11412010; Ashe P C et al., Prog. Neuropsychopharmacol Biol Psychiatry 25, 691-707, 2001; Brown G M et al., Prog. Neuropsychopharmacol Biol. Psychiatry 80, 189-204, 2018). Moreover, all these disorders are caused/worsened by stress and/or lead to appetite disturbances.

For therapeutic use, the compounds described herein may be administered in any conventional dosage form in any conventional manner. Routes of administration include, but are not limited to oral administration, dermal administration, inhaled administration, intravenous, intramuscular and subcutaneous injections. The preferred modes of administration are oral, intravenous or subcutaneous.

The compounds may be administered alone or in combination with adjuvants that enhance stability of the compounds, facilitate administration of pharmaceutical compositions containing them in certain embodiments, retard or enhance the release of the compounds, provide increased dissolution or dispersion, increase activity, provide adjunct therapy (e.g. with approved drugs for the treatment of AD, or inhibitors of the ACE or the AT1 receptor) and the like, including other active ingredients.

The herein-described compounds may be physically combined with conventional therapeutics or other adjuvants into a single pharmaceutical composition. Reference in this regard may be made to Cappola et al.: U.S. patent application Ser. No. 09/902,822, PCT/US 01/21860 und U.S. provisional application No. 60/313,527, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of the present invention (w/w). The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. Methods for preparing such dosage forms are known (see, for example, H. C. Ansel and N. G. Popovish, Pharmaceutical Dosage Forms and Drug Delivery Systems, $5^{th}$ ed., Lea and Febiger (1990)). Dosage levels and requirements are well-recognized in the art and may be selected by those of ordinary skill in the art from available methods and techniques suitable for a particular patient. In some embodiments, dosage levels range from 1-500 mg/dose for a 70 kg patient. Although one dose per day may be sufficient, up to 5 doses per day may be given. For oral doses, up to 2500 mg/day may be required. Reference in this regard may also be made to U.S. provisional application No. 60/339,249. As the skilled artisan will appreciate, lower or higher doses may be required depending on particular factors. For instance, specific doses and treatment regimens will depend on factors such as the patient's general health profile, the severity and course of the patient's disorder or disposition thereto, and the judgment of the treating physician.

In another aspect, the present invention is directed to a method for the therapeutic or prophylactic treatment of a patient suffering or likely of suffering from a CNS- or neurodegenerative disease, preferably a mammalian patient, more preferably a human patient, the method comprising the step of administering a therapeutically or prophylactically effective amount of a compound or pharmaceutical composition for use according to the present disclosure to the patient in need of such treatment.

In a further aspect, the present invention is directed to a method for determining treatment progression or outcome of senescence and anti-aging treatment comprising the following steps:

(a) providing a patient sample, preferably a sample prepared from a cell, organ, organoid, more preferably a sample prepared from blood cells, most preferably from peripheral blood mononuclear cells;
(b) detecting Membrane Palmitoylated Protein 1 (MPP1) in the sample of step (a) and optionally quantifying the amounts of MPP1 in the sample;
(c) optionally comparing the MPP1 amounts in the sample with the MPP amounts in a sample taken before senescence and anti-aging treatment was started in the patient;
(d) determining the treatment outcome of senescence and anti-aging treatment based on the detection and optionally quantification of MPP1.

To monitor the aging process in a cell, organ, organoids, whole organism, the senescence marker Membrane Palmitoylated Protein 1 (MPP1/Mpp1) can be detected in a protein lysate, which is prepared from any cell, organ, organoids, whole organism, preferably from blood cells, more preferably from peripheral blood mononuclear cells of a human or mammal. The method preferably detects MPP1/Mpp1 in a human cell or biopsy specimen isolated from a healthy or diseased individual. For example, the senescence marker can also be detected in any experimental model, which can be used to study processes of aging and which has the MPP1/Mpp1 protein. A model organism can be but is not restricted to mouse, dog, primates, cow, preferably a rodent, more preferably a mouse. Because MPP1/Mpp1 is a senescence marker, comparative detection of MPP1/Mpp1 can be performed with specimens from different age groups and/or with and without application of a compound of interest used to modify/retard the aging process and/or symptoms of aging. Preferred human specimens/samples are human peripheral blood and/or total circulating blood cells and/or a cell fraction isolated thereof, which can be platelets, leucocytes, erythrocytes and/or polymorphonuclear cells. The preferred cell type is peripheral blood mononuclear (PBMN) cells, which can be isolated from mammalian, e.g. mouse or human blood plasma, e.g. but not restricted to by density gradient centrifugation with Ficoll® Paque Plus (GE Healthcare) or by any other density gradient medium. Examples include but are not limited to Lymphoprep™ (Abbott Diagnostics Technologies AS, Oslo, Norway), Percoll Media (GE Healthcare), Histopaque 10771 (for human mononuclear cells) or HIstopaque 10831 (for mononuclear cells from mice, rats and other mammals) (Sigma Aldrich), RosetteSep™ DM-L Density Medium, RosetteSep™ DM-M Density Medium (STEMCELL Technologies, Vancouver, Canada) as detailed above.

In a preferred embodiment, MPP1/Mpp1 detection may be achieved by a standard immunological method, preferably immunoblotting after electrophoretic transfer of proteins to a membrane by Western blotting. Another preferred immunological method for MPP1/Mpp1 detection is by ELISA or RIA. Other preferred immunological methods for MPP1/Mpp1 detection are by immunohistology, immunofluorescence, fluorescence microscopy, TIRF microscopy Vertico-SMI, STED-microscopy, 3D-SIM microscopy, photoactivated-localization microscopy, fluorescence-activated cell sorting, flow cytometry, and electron microscopy. For immunological detection, an antibody (e.g. polyclonal, monoclonal, from mouse, rabbit, any species including single-domain antibodies from cameloids, sharks) against MPP1/Mpp1 is preferably used. Preferably, the antibody is raised in rabbit, or mouse against full-length recombinant MPP1/Mpp1 protein. Alternatively, an antibody against MPP1/Mpp1 can be raised against a peptide sequence of MPP1/Mpp1 (10-20 amino acids, up to 30-40 amino acids) or a recombinant fusion protein, or the recombinant full-length MPP1/Mpp1 protein. An antibody recognition epitope is typically 5-7 amino acids in length. Antibodies against MPP1/Mpp1 can also be isolated from a phage display antibody library by panning with purified recombinant MPP1/Mpp1 protein and/or protein fragments/peptides thereof.

In a further preferred method, MPP1/Mpp1 detection is made by Western blotting. A protein lysate can be prepared from any cell, organ, organoids, whole organisms, preferably from blood cells, more preferably from PBMN cells. Preferably, a human cell or biopsy specimen isolated from healthy or diseased individuals is used in the method. Preferred human specimens are human peripheral blood and/or total circulating blood cells and/or a cell fraction isolated thereof, which can be platelets, leucocytes, erythrocytes and/or polymorphonuclear cells. For immunoblot detection of proteins, preferably the MPP1/Mpp1 protein, tissue, biopsy specimen, cultured cells, blood cells, (fresh or frozen tissue or cells) is/are preferably homogenized (e.g. mechanically, manually) at a temperature ranging from, e.g., about −210° C. to about +30° C., preferably under liquid nitrogen (temperature range of about −210° C. to about −196° C.), and extracted for, e.g., about 15 min-120 min, preferably for about 30 min at about 4° C.-24° C. preferably at about 4° C. with any standard solubilization buffer. The method of protein extraction from cells, preferably from PBMN cells can be performed similarly as detailed herein for the extraction of hippocampal proteins or proteins from cells. Proteins from PBMN cells can be extracted by any standard solubilization buffer, which can be but is not restricted to RIPA (radioimmunoprecipitation assay) buffer, which can be but is not restricted to the following composition: sodium deoxycholate at a concentration of about 0.1%-2%, preferably about 1%, SDS at a concentration ranging between 0.05% to 2%, preferably about 0.1%, NP40 (IGEPAL) ranging from about 0.01% to 0.5%, preferably about 0.1%, EDTA, EGTA or another divalent cation chelator ranging from about 0 mM to 20 mM, preferably about 5 mM, Tris ranging from about 5 mM to 500 mM, preferably about 50 mM with a pH ranging from about pH6 to pH10, preferably about pH 8.0, supplemented without or with additional salts (e.g. NaCl ranging from about 0-500 mM) to modify ionic strength. Any other buffer (e.g. PBS, PIPES, HEPES, bicine), with a pH varying from about pH 5-pH 10, preferably about pH 6-9, supplemented with any state of the art detergent (e.g. anionic, cationic, non-ionic, zwitterionic) is also suitable for extraction. Other suitable detergents or mixtures thereof include but are not limited to CHAPS, CHAPSO, C7BzO, ASB-14, n-Dodecyl beta-D-maltoside, Octyl beta-D-glucopyranoside, Octyl beta-D1-thioglucopyranoside, Polyoyethylene 10 tridecyl ether, Brij® 56, Triton X-100, 3-(Decyldimethyl-ammonio)propanesulfonate inner salt. As an alternative to the buffers described above, any commercially available protein extraction buffer (non-denaturing or denaturing) or kit can be used for protein extraction, which includes, e.g., the following examples: T-PER Tissue Protein Extraction Reagent (ThermoFisher Scientific), M-PER Mammalian Protein Extraction Reagent (ThermoFisher Scientific), Pierce IP Lysis buffer, a protein extraction kit from SigmaAldrich (PROTMEM, PROTTWO, PROTOT). The used protein extraction buffer can be routinely supplemented with any state of the art cocktail of protease/phosphatase inhibitors (e.g. Cat. No. P8349, and/or PPC1010, Sigma-Aldrich, St. Louis, MO, USA). In case of cells, direct solubilisation of fresh or frozen cell pellets is also possible without prior homogenization. Solubilization can be enhanced by sonification. It is preferred to remove particulate material after solubilisation. Methods for the removal of insoluble material include but are not limited to filtration or centrifugation at about 5 000×g-100 000×g, preferably about 50 000×g for about 1-120 min, preferably about 20 min at about 4° C.-30° C., preferably about 4° C. Solubilized proteins can be used directly for MPP1/Mpp1 protein detection, or proteins can be further concentrated. Concentration of proteins can be performed, e.g., by precipitation with a suitable solvent, which can be but is not limited to TCA, ethanol, isopropanol, acetone/methanol. Preferably, the method applies a mixture of ice-cold acetone/methanol, preferably about 12:2, added to a final concentration of about 60-95%, preferably about 83% for at least >5 min up to an indefinite time preferably about 90 min at a preferred temperature ranging between about −210° C. to 4° C., preferably about 4° C. Any other method of protein concentration is also suitable. For example, protein concentration can also be achieved by centrifugation over a protein concentration cartridge, which can be but is not restricted to, e.g., Amicon Ultracentrifugal filter units, MWCO 3 kDa, (Millipore).

For protein separation by SDS-PAGE (Laemmli system), the protein pellet can be dissolved in SDS-PAGE sample buffer supplemented with SDS. As an alternative, sample buffer for native gel electrophoresis can be added. According to the original protocol, the SDS-PAGE Laemmli sample buffer contains 2% SDS, 0.1 M DTT (or 5% mercaptoethanol). To improve disaggregation of aggregated proteins, the buffer can be supplemented without or with urea ranging from about 0 M-8 M, preferably about 6 M urea and incubated for about 10 min to 24 h, preferably about 90 min at room temperature. Proteins can be stored frozen (about −210° C.-20° C.) at a concentration ranging from about 0.01-100 mg/ml, preferably about 0.5 mg-1 mg/ml, for further use. It may be further desirable to dilute the solubilisate, for example, diluting the supernatant solubilisate by 1:1-1:20, preferably 1:5, in a suitable buffer as described above (preferably supplemented with protease inhibitors). Before immunoblot detection of proteins, proteins are separated. For separation of proteins, one- or two-dimensional SDS-PAGE can be applied. For example, solubilized proteins are subjected to about 7-15%, preferably about 8% denaturing SDS-PAGE under non-reducing or reducing conditions supplemented without or with about 1-8 M urea, preferably about 6-8 M, more preferably about 8 M. As an alternative example, native gel electrophoresis and/or two-dimensional gel electrophoresis is also suitable. After separation of proteins, electrophoretic protein transfer can be performed to a suitable membrane, which can be but is not restricted to a PVDF membrane or a nitrocellulose membrane, preferably a PVDF membrane in a transfer cell, preferably a tank transfer cell (e.g. with but not restricted to a Mini Trans-Blot cell, Bio-Rad GmbH, München, Germany), or a semi-dry transfer apparatus (e.g. with but not restricted to Trans-Blot SD semi-dry transfer cell, Bio-Rad GmbH, München, Germany). After protein transfer, immunoblot detection of proteins (i.e. the senescence marker, MPP1) can be performed with antibody-containing liquids preferably serum, and/or purified antibodies, preferably immunogen affinity-purified antibodies, derivatives, fragments or analogues thereof, preferably with affinity-purified antibodies or $F(ab)_2$ fragments of the respective antibodies or antibody analogues. In a typical and exemplary experiment, MPP1-specific antibodies for detection of the senescence marker MPP1 were polyclonal anti-MPP1 antibodies, which were raised in rabbits against a recombinant fragment containing a sequence corresponding to a region within amino acids 214-398 of human MPP1 (ab96255, abcam). To avoid non-specific antibody binding, non-specific binding sites are blocked by prior incubation of the membrane with a blocking buffer containing a blocking reagent, which can be but is not restricted to an albumin, preferably bovine serum albumin, gelatine, and/or non-fat dried milk powder or any other blocking reagent. Depending on the antibody affinity, the antibody is applied at a dilution of 1:2-1:200 000, preferably 1:100-1:50 000, more preferably 1:1000-1:10 000. After washing steps to remove unbound antibody, bound antibodies can be visualized with secondary enzyme-coupled antibodies, more preferably $F(ab)_2$ fragments of enzyme-coupled (e.g. but not restricted to alkaline phosphatase- or peroxidase-conjugated preferably peroxidase-conjugated) secondary antibodies (e.g. Dianova GmbH, Hamburg, Germany), which are pre-absorbed to mouse and/or human serum proteins, and followed by enhanced chemiluminescent detection (e.g. with ECL Plus, and/or ECL Prime, Amersham, GE Healthcare Life Sciences, Glattbrugg, Switzerland). An alternative is the detection by enzyme-coupled protein A or G (e.g. EMD Millipore, Merck KGaA, Darmstadt, Germany), which is also followed by enhanced chemiluminescent detection. A colorimetric detection method can also be used, which acts by producing a coloured precipitate from an enzymatic reaction (e.g. but not restricted to HRP, which catalyses a reaction with 4-Chloro-1-napthol (4CN) and peroxide that produces a visible and insoluble purple product). Any other western blot detection system is also suitable e.g. by Chemi-IR fluorescence detection (for example but not restricted to Odyssey Western blot system Li-Cor) or Europium-labelled secondary antibodies or streptavidin (for example but not restricted to ScanLater Western blot system, Molecular Devices). Direct labelling of the secondary antibody with a fluorescence molecule (without enzyme substrate reaction) is also feasible. Another alternative is the direct labelling of the primary or secondary antibody or the protein A or G with a radiolabel (preferably $^{125}I$). To control for equal protein loading, a control protein can be detected. A standard loading control involves, e.g., detection of a house-keeping protein, e.g. actin, tubulin, Gapdh. Also, detection of Gnb (i.e. the Gbeta subunit of heterotrimeric G-proteins) can be an alternative loading control. For quantitation of mitochondrial proteins, detection of a mitochondrial protein is performed, preferably Atp6v1a. Due to signal amplification, visualization of bound primary antibody by a secondary antibody is the preferred method of detection.

Alternative detection methods for MPP1/Mpp1 are, for example, based on any MMP1/Mpp1-interacting compound or composition, e.g. a MPP1/Mpp1-interacting compound or composition for use in the present invention, a synthetic antibody, an antibody fragment (synthetic or native), a peptide, a protein, an enzyme, which is labelled for further detection. If the MPP1/Mpp1-interacting compound or composition is not labelled, detection can be performed by a secondary detection reaction (see above). Labelling of the MPP1/Mpp1-interacting compound or composition can be performed by a radiolabel (e.g. $^{3}H$, $^{15}I$ $^{35}S$, $^{33}$, $^{14}C$), or a non-radioactive method, e.g. an enzyme (e.g. peroxidase, alkaline phosphatase), biotin, Europium, fluorescent label (e.g. FITC, TRITC, ALEXA Fluor Dyes), colloidal gold particles, any other chemical dye, a protein or a fluorescent protein, which is attached by chemical crosslinking or fusion of the DNA. Examples for fluorescent proteins include but are not limited to the green fluorescent protein and variants thereof (e.g. EYFP, EGFP, Cerulean, ECFP, mCherry fluorescent protein; HyPer; RoGFP; rxYFPM PROPS, VSFP, zoanFP). By similar methods a short peptide Tag (e.g. HA, FLAG) can be attached to allow visualization and/or quantification of MPP1/Mpp1. Other possible labelling methods for a MPP1/Mpp1-interacting compound or composition also include the SNAP-Tag or the CLIP-Tag® technology (New England Biolabs, Biotechnology, USA). A preferred method also includes quantitation of MPP1/Mpp1 by secondary detection of the MPP1/Mpp1-interacting compound or composition with a secondary entity, which interacts with the primary MPP1/Mpp1-interacting compound or composition. The secondary interacting entity (e.g. protein/compound) can be similarly modified as detailed above for the primary MPP1/Mpp1-interacting compound or composition.

Another preferred method for MPP1/Mpp1 detection in a blood plasma sample, cellular protein extract or solubilisate is an ELISA or RIA method. To this end the MPP1/Mpp1-containing protein sample or a dilution thereof can be used to coat ELISA plates (e.g. but not restricted to NUNC maxisorb, Thermo Scientific) at a concentration of about 0.1-10 microg, preferably about 1-4 microg, more preferably about 2 microg. After a washing step to remove unbound proteins, and a blocking step, the first MPP/Mpp1 interacting antibody or entity is applied. After another washing step to remove unbound antibody/protein (MPP1/Mpp1-interacting entity), the bound entity can be detected by a secondary antibody, which is labelled for further detection (e.g. with an enzyme, e.g. peroxidase). The secondary antibody (entity) interacts with the first antibody. The amount of bound antibody (entity) is quantified by a detection reaction, e.g. based on but not restricted to an enzyme-substrate reaction, or a direct detection method, which applies a secondary antibody (or detection reagent such as biotin-streptavidin) by a fluorescent label or Europium for TR-FIA (time-resolved fluoroimmunoassay). Another preferred alternative is a sandwich ELISA (performed analogously to the direct detection method as detailed above). In the sandwich ELISA, the ELISA plate is coated with an MPP1/Mpp1-interacting antibody, antibody-fragment, and/or MPP1-/Mpp1-interacting entity or compound. After washing steps to remove unbound proteins (entity), the MPP1/Mpp1-containing protein lysate (cell lysate, which is prepared as detailed above) is applied and incubated, e.g. for about 1 min to about 24 h or longer at, e.g., about 4° C. to 37° C., preferably about 1 h at about 37° C. Unbound proteins can be removed by washing. In the next step, the bound MPP1/Mpp1 is detected with another MPP1/Mpp1-interacting antibody/entity, which recognizes and interacts with another epitope of MPP1/Mpp1 as the antibody/entity used for the initial coating step of the plate. If an antibody is used, the antibody is raised in another species as the first coating antibody. In the final step, the MPP1/Mpp1-bound antibody is either quantified directly (when the MPP1/Mpp1-specific antibody is labelled) or indirectly with a secondary antibody/entity followed by a detection method as detailed above. Another preferred alternative for MPP1/Mpp1 is radioimmunoassay, in which the detection reaction is based on a radiolabelled entity.

The above-described principle of the ELISA method can be miniaturized, e.g. on a test strip. In addition, incubation times of the different reactions can be shortened and can be performed in parallel instead of the sequential order. Another alternative, is the modification of the above-described test principle, for a microfluidics station.

Another preferred method is the quantitation of MPP1/Mpp1 by determination of MPP1/Mpp1 gene expression level by state of the art methods: e.g. Northern blotting, microarray gene expression analysis, transcriptome sequencing. Notably, the experiments described herein showed that quantitative determination of MPP1 gene expression level using total RNA isolated from peripheral blood mononuclear (PBMN) cells is a versatile and reliable method to discriminate old age groups (e.g. but not restricted to ≥75 years) from younger aged individuals (e.g. but not restricted to ≤50 years), and to monitor the treatment effect with an anti-aging compound in an individual receiving such a treatment (cf. FIG. 9, FIG. 10, FIG. 23).

With all different methods of quantitative MPP1/Mpp1 detection in peripheral blood mononuclear cells (e.g. by quantifying the MPP1/Mpp1 protein content and/or MPP1/Mpp1 RNA level), individuals belonging to a specific age group ((e.g. but not restricted to ≥75 years) or ((e.g. but not restricted to ≤50 years) can be discriminated, the biological age can be determined and the treatment effect can be monitored in an individual receiving such a treatment.

To monitor the anti-aging treatment effect of any therapeutic intervention, preferably with a small molecule compound or an antibody, the cellular MPP1/Mpp1 protein or RNA content can be determined before treatment, and/or at various time points during or after treatment. By inclusion of a reference control group from a cohort of healthy young individuals, the biological age before, during and after treatment can be assessed and quantified. Thus, any reference group can be used to determine treatment-induced changes.

The following Figures and Examples serve to illustrate the invention and are not intended to limit the scope of the invention as described in the appended claims.

FIGURES

FIG. 1. Compound-1 and Compound-4 retard Abeta plaque formation in Tg2576 mice FIG. 1A shows the chemical formulas of Compound-1: 1-(1,3-benzodioxol-5-yl)-4-(cyclopropane-carbonyl)-3-hydroxy-2-phenyl-2H-pyrrol-5-one; and Compound-4: 4-(1,3-benzodioxol-5-yl)pyrimidine;

FIGS. 1B and 1C illustrate the immunohistological assessment of Abeta plaque load in hippocampal and frontal cortex areas from 18 months-old Tg2576 mice treated with Compound-1 and Compound-4 for 6 months compared to untreated Tg2576 mice. The upper panels show images from 4 mice/group (B), and the lower panel (C) shows quantitative evaluation of plaque area (±s.d., n=8; ***, p<0.001; Tukey's test).

Figure 2:
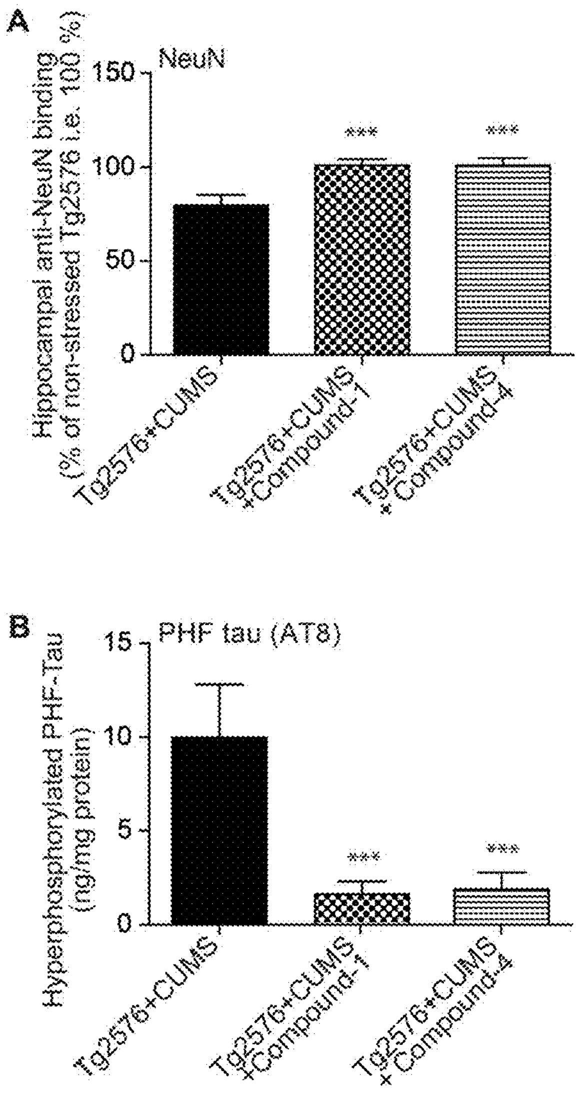

FIG. 2. Compound-1 and Compound-4 retard hippocampal neuronal loss and Tau hyperphosphorylation in Tg2576 mice subjected to CUMS (chronic unpredictable mild stress)

FIGS. 2A and 2B show the quantification of neuronal cell bodies by direct binding assay with [$^{125}$I]-labeled anti-NeuN antibody (A) and hyperphosphorylated Tau with [125I]-labeled AT8 antibody (B) in hippocampi isolated from 15 months-old Tg2576 mice subjected to the CUMS (chronic unpredictable mild stress) protocol for three months and treated with Compound-1 and Compound-4 compared to untreated stressed Tg2576 controls (±s.d., n=8; ***, p<0.001; Tukey's test).

Figure 3:
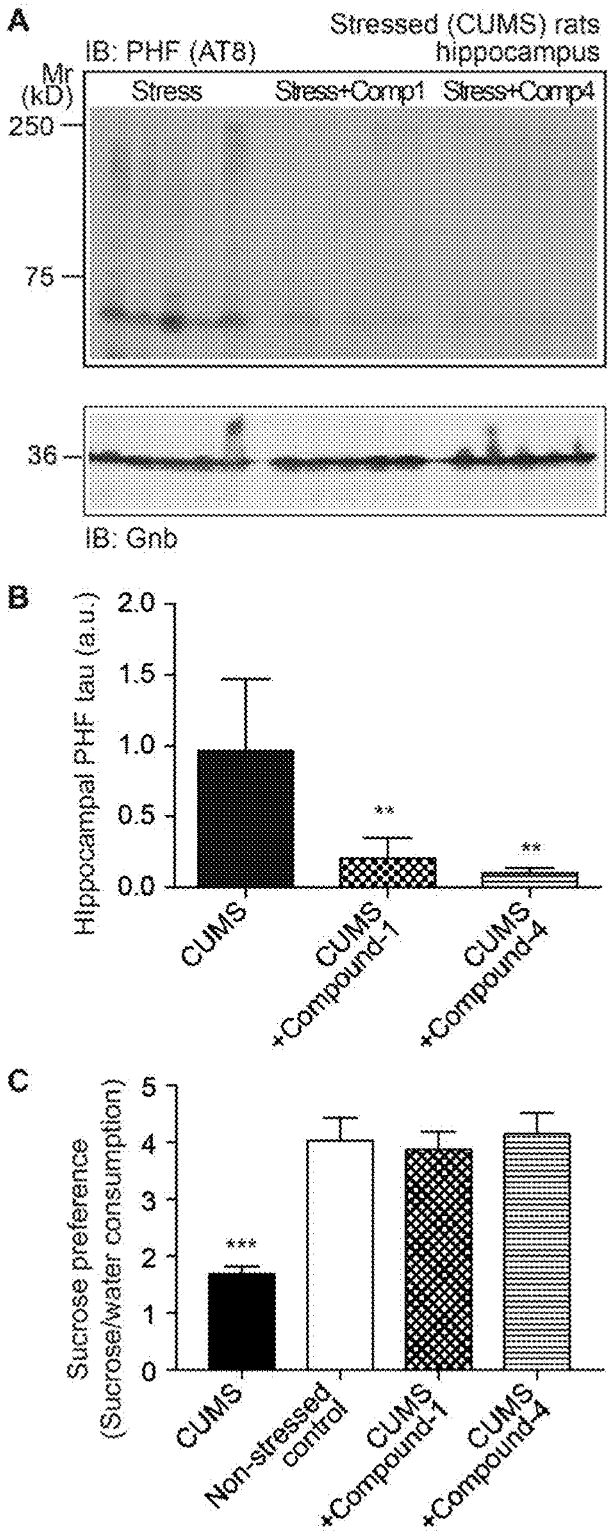

FIG. 3. Compound-1 and Compound-4 retard hippocampal Tau hyperphosphorylation and prevent symptoms of depression in a rat model of depression with symptoms of sporadic AD FIGS. 3A and 3B demonstrate hippocampal Tau hyperphosphorylation as determined in an immunoblot with anti-PHF antibody (AT8) in a rat model of depression with symptoms of sporadic AD triggered in 16 months-old rats by the CUMS protocol for 4 weeks. Hippocampi were evaluated from stressed rats treated with Compound-1 and Compound-4 relative to untreated rats with CUMS (n=5/group). The upper panel shows immunoblot detection (A), and the lower panel (B) shows quantitative data evaluation (±s.d., n=5, **, p=0.0014 vs. untreated control rats subjected to CUMS; Tukey's test).

FIG. 3C shows that oral treatment with Compound-1 and Compound-4 prevents CUMS-induced anhedonia as a major symptom of depression. Anhedonia was induced by 4 weeks of CUMS in aged 16-month-old rats compared to non-stressed age-matched controls. Treatment with Compound-1 and Compound-4 prevented anhedonia as determined with the sucrose preference test. The sucrose preference is presented as the ratio of sucrose-to-water consumption (±s.d.; n=5; ***, p<0.001 vs. untreated non-stressed controls and vs. Compound-1- and Compound-4-treated rats subjected to the CUMS protocol; Tukey's test).

Figure 4:
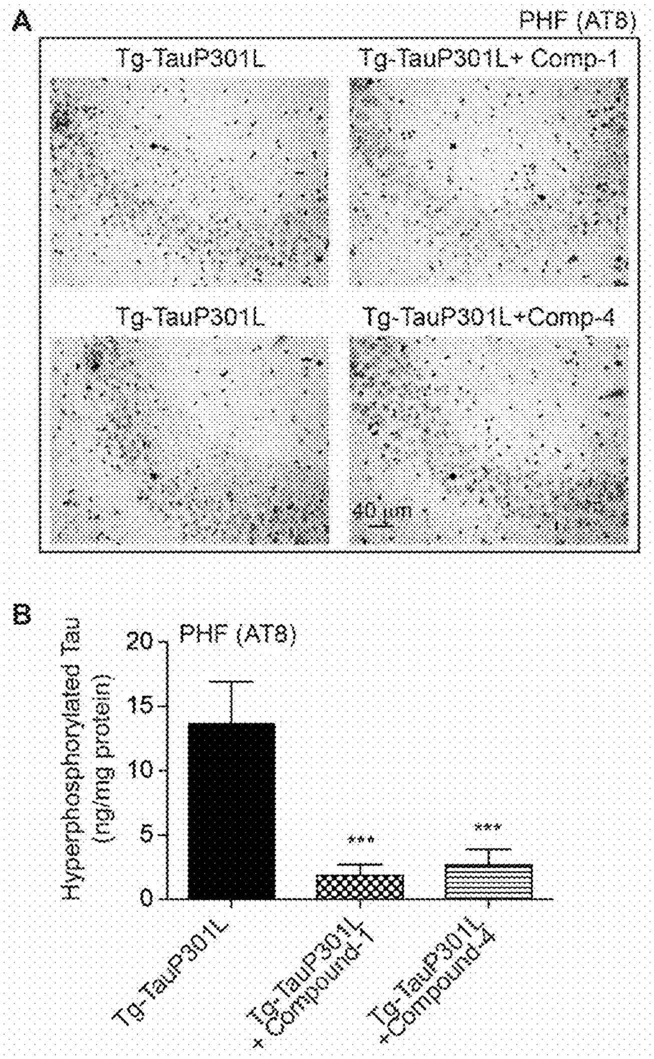

FIG. 4. Compound-1 and Compound-4 retard Tau hyperphosphorylation in the Tg-TauP301L model of tauopathy FIG. 4A illustrates the immunohistological detection of hippocampal Tau hyperphosphorylation as performed with anti-PHF antibody (AT8) on hippocampal sections of 12 months-old Tg-TauP301L mice after treatment for 6 months with Compound-1 and Compound-4 compared to untreated Tg-TauP301L controls; bar: 40 microm.

FIG. 4B is a bar graph showing the quantitative determination of hippocampal Tau hyperphosphorylation in 12 months-old Tg-TauP301L mice after treatment for 6 months with Compound-1 and Compound-4 compared to untreated Tg-TauP301L controls was performed by direct binding assay with [125I]-labeled AT8 antibody (±s.d., n=8, ***, p<0.001; Tukey's test).

Figure 5:
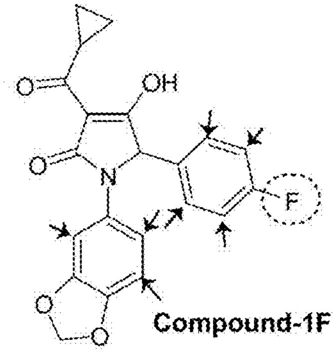
Figure 5:
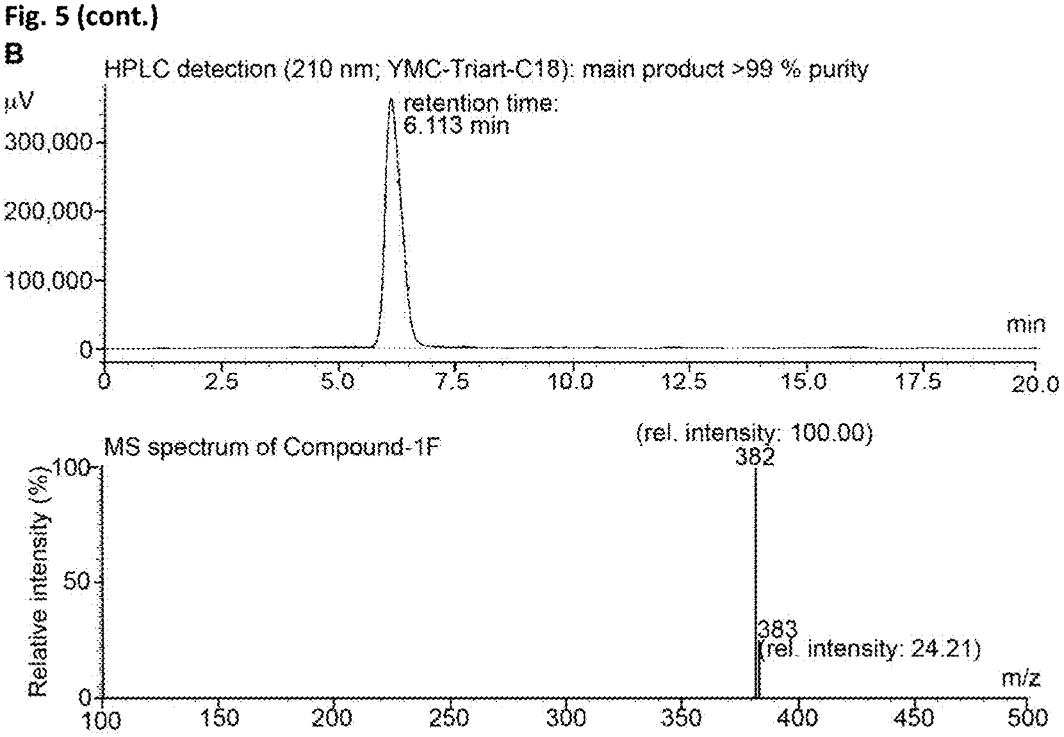

FIG. 5 shows the development of fluorinated Compound-1F as an analogue of Compound-1 with modified physicochemical and pharmacokinetic properties. (A) Formula of Compound-1F. Arrowheads mark preferred positions of fluorination, e.g. for modifying the physicochemical and pharmacokinetic properties of Compound-1F. (B) Characterization of Compound-1F by HPLC-MS analysis confirmed identity and purity (>99%) of Compound-1F.

Figure 6:
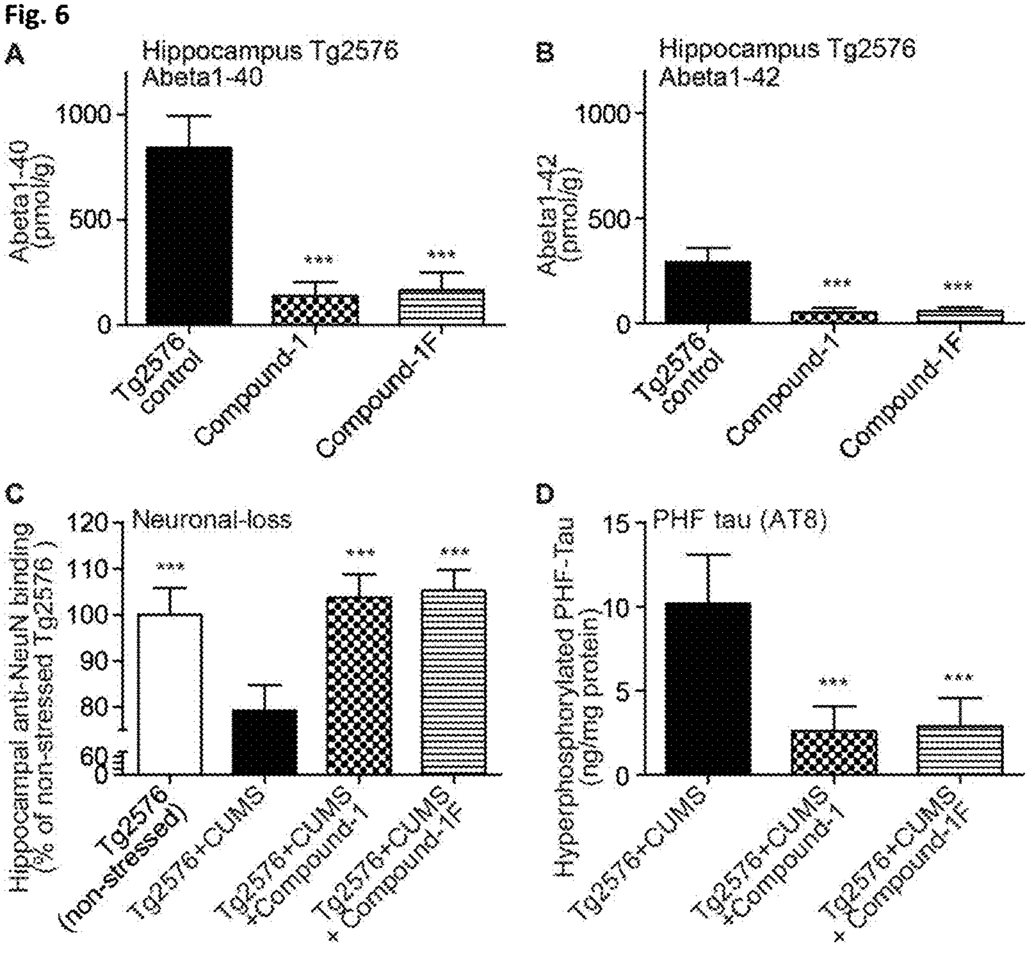

FIG. 6 shows that Compound-1 and Compound-1F retarded hippocampal Abeta plaque accumulation, neuronal loss and neuronal cell loss-causing PHF tau hyperphosphorylation in Tg2576 AD mice. (A,B) Hippocampal contents of Abeta1-40 (A) and Abeta1-42 (B) were significantly decreased in 18 months-old Tg2576 mice after 6 months of treatment with Compound-1 and Compound-1F (8 mg/kg/d in drinking water). (C,D) Treatment with Compound-1F and Compound-1 retarded hippocampal neuronal loss (C) and neuronal cell loss-causing PHF tau hyperphosphorylation (D) induced by 3 months of CUMS (chronic unpredictable mild stress) in 15-month-old Tg2576 AD mice. Hippocampal neuronal cell bodies and PHF tau hyperphosphorylation were quantified by direct binding assay with [125I]-labelled anti-NeuN antibody and [125I]-labelled anti-PHF tau (AT8) antibody; (±s.d., n=6, ***, p<0.001; Tukey's test).

Figure 7:
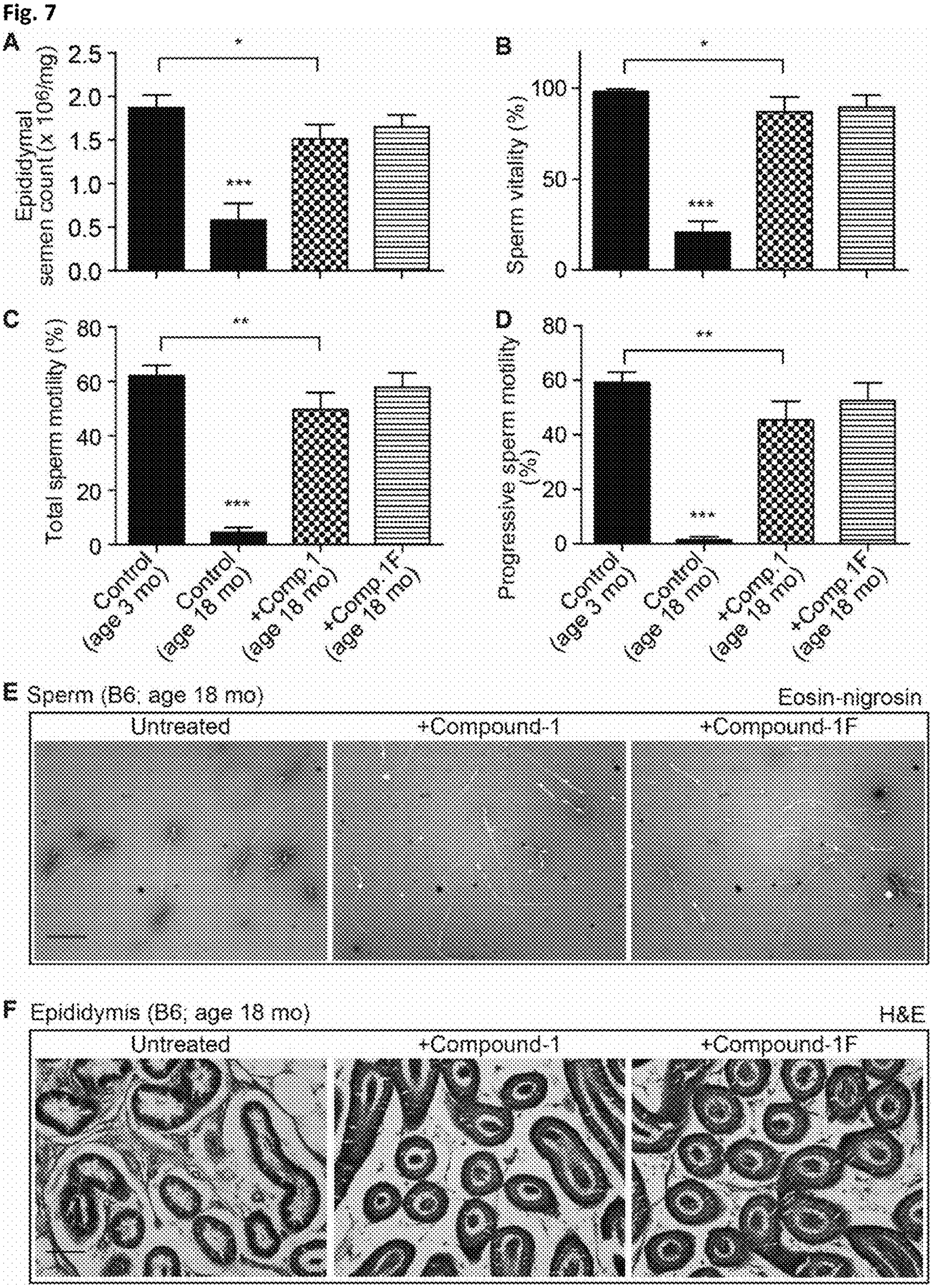

FIG. 7 shows that Compound-1 and Compound-1F retarded the aging-induced decline in male fertility as a major symptom of aging. (A-D). Treatment for 15 months with Compound-1 and Compound-1F (8 mg/kg/d in drinking water) retarded the aging-induced decrease in epididymal sperm count (A), maintained sperm vitality as determined by eosin-nigrosin-staining (B), improved total sperm motility (C), and progressive sperm motility (D) of 18-month-old male B6 mice (±s.d.; n=5; *p<0.05; p<0.01; *p<0.001; Tukey's test). (E) Representative images of sperm vitality staining with eosin-nigrosine show that the aging-induced decrease in sperm vitality of 18-month-old B6 mice was retarded by treatment for 15 months with Compound-1 and Compound-1F. Sperm vitality was determined by eosin-nigrosine-staining; bar 10 microm. Live sperm cells appear white whereas dead sperm cells are stained pink. Quantitative sperm vitality data are shown in (B). (F) Aging-induced epididymal degeneration of 18-month-old male B6 mice was retarded by treatment for 15 months with Compound-1 and Compound-1F. Hematoxylin-eosin (H&E)-stained sections of the cauda epididymis showed very few spermatozoa in tubule lumens of untreated mice compared to a high sperm abundance in treated mice. Hematoxylin-eosin-stained sections are representative of 5 mice/group (bar: 100 microm).

Figure 8:
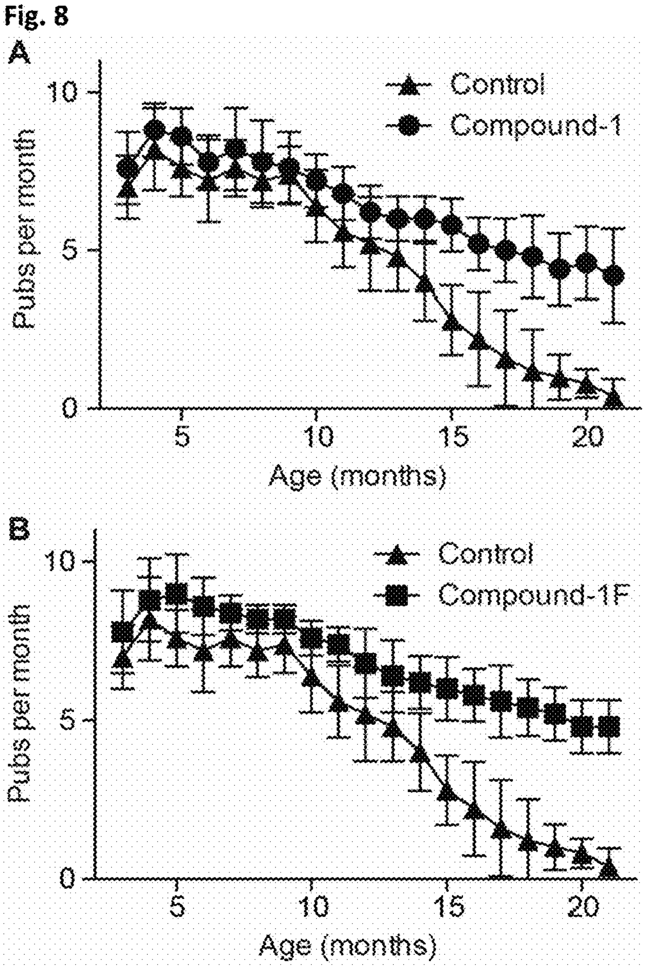

FIG. 8 shows that the treatment with Compound-1 and Compound-1F retarded aging-induced decrease in fertility in female B6 mice. (A,B) Treatment of B6 mice with Compound-1 (A) and Compound-1F (B) at a daily dose of 8 mg/kg/d in drinking water was started at an age of 3 months and continued until the end of the observation period at 21 months. The age of the male breeder(s) was <10 months. The number of offspring per month is given (±s.d.; n=5; p=0.0167 for Compound-1, and p=0.0032 for Compound-1F compared to untreated controls; unpaired, two-tailed Student's t-test).

Figure 9:
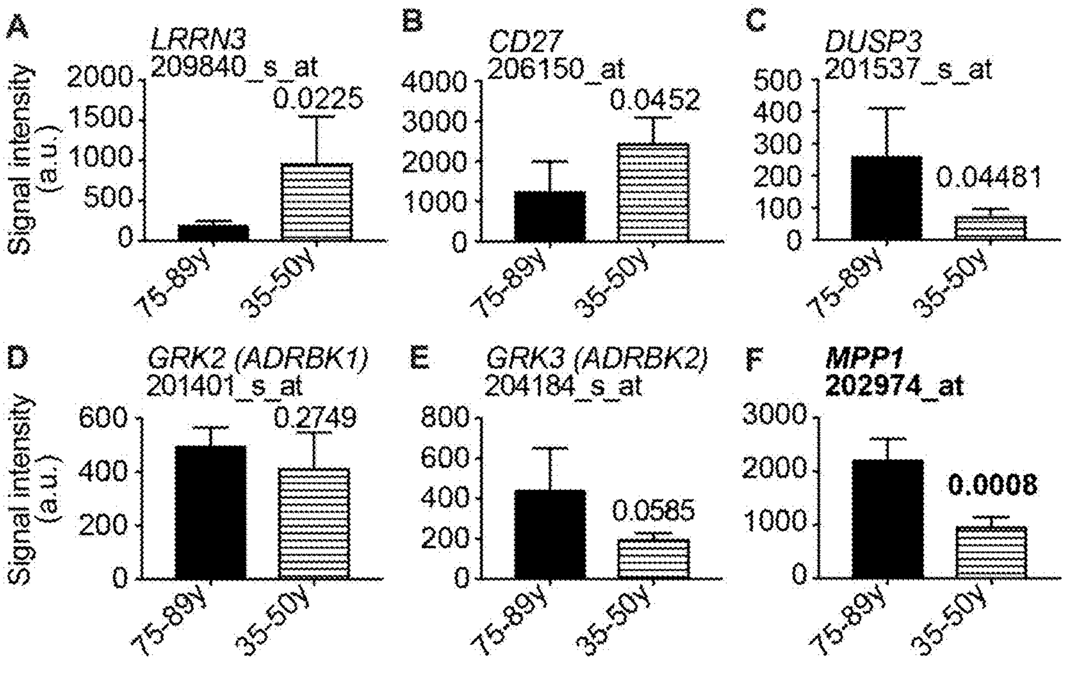

FIG. 9 shows the Identification of MPP1 as a senescence marker in human peripheral blood mononuclear cells. (A-F) Whole genome microarray gene expression profiling data from human peripheral blood mononuclear (PBMN) cells isolated from individuals aged 75-89 years (n=5) and 35-50 years (n=4) are presented for probe sets detecting LRRN3 (A: 209840_s_at), CD27 (B: 206150_at), DUSP3 (C: 201537_s_at), GRK2 (ADRBK1) (D: 201401_s_at), GRK3 (ADRKB2) (E: 204184_s_at), and MPP1 (F: 202974_at). Statistical significance of comparisons is indicated (unpaired, two-tailed Student's t-test) and is highest for MPP1.

Figure 10:
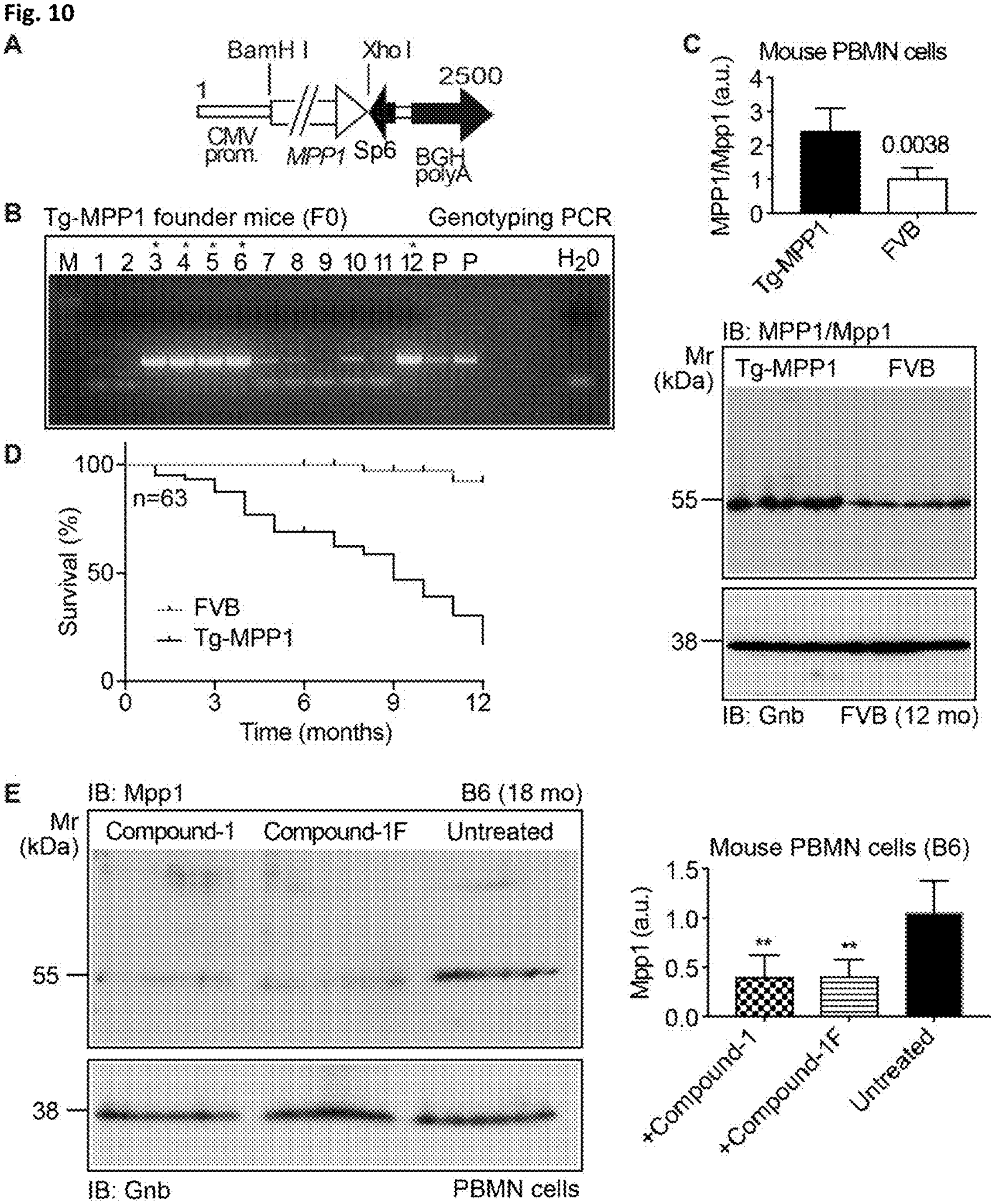

FIG. 10 shows that Tg-MPP1 mice develop a phenotype of premature aging. (A) Scheme of the plasmid used for generation of Tg-MPP1 mice. The cDNA encoding MPP1 was inserted into the BamHI-XhoI sites of plasmid pcDNA3. (B) Identification of transgenic Tg-MPP1 founder mice (F0) by genotyping PCR. Founders no. 4 and 6 were used for further breeding. (C) Increased MPP1/Mpp1 protein content of peripheral blood mononuclear cells from aged (12-month-old) Tg-MPP1 mice compared to age-matched non-transgenic FVB control mice (±s.d.; n=5). Statistical significance is indicated and was determined by the unpaired, two-tailed Student's t-test. The upper panel presents quantitative data, and the lower panel shows a representative immunoblot. (D) Premature senescence of Tg-MPP1 mice is documented by a significantly reduced lifespan of Tg-MPP1 mice compared to non-transgenic FVB mice. (E) Treatment for 15 months with Compound-1 and Compound-1F significantly retarded the accumulation of the senescence-inducing protein Mpp1 in aged (18-month-old) non-transgenic B6 mice. The left panel shows a representative immunoblot, and the right panel shows quantitative data (±s.d.; n=6; **p<0.01; Tukey's test).

Figure 11:
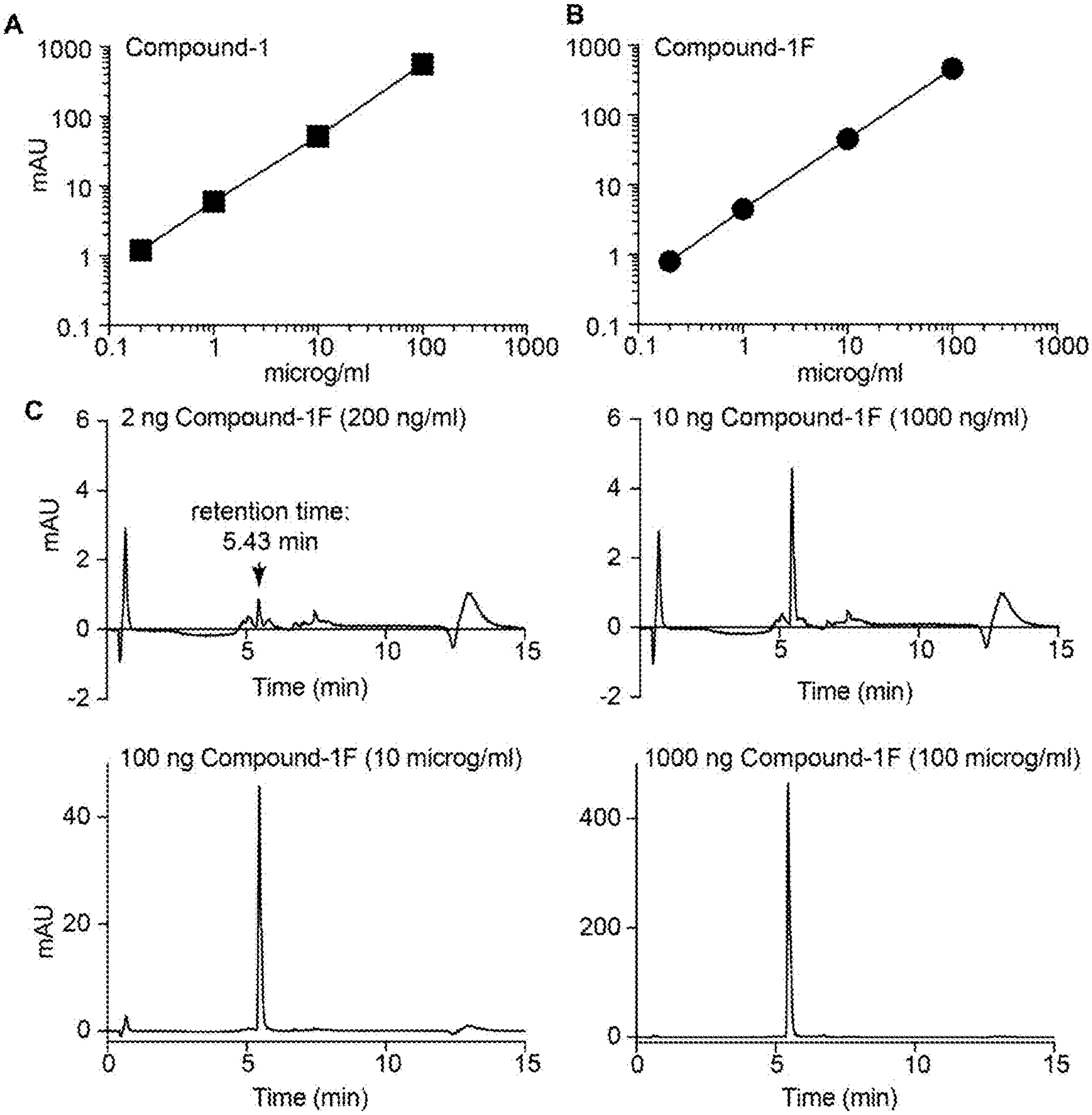

FIG. 11 shows the quantitative determination of Compound-1, Compound-1F in serum by HPLC. (A,B) Linear calibration curves for HPLC detection of Compound-1 (A), and Compound-1F (B) over the concentration range from 200 ng/ml to 100 microg/ml. (C) Representative HPLC chromatograms for detection of Compound-1F at a concentration range of 200 ng/ml to 100 microg/ml. The limit of detection for Compound-1F was below <2 ng when injected in a volume of 10 microl, which is equivalent to the concentration of 200 ng/ml.

Figure 12:
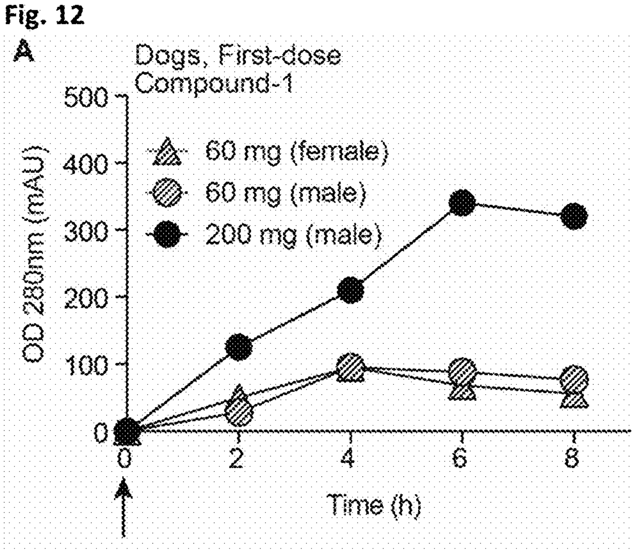
Figure 12:
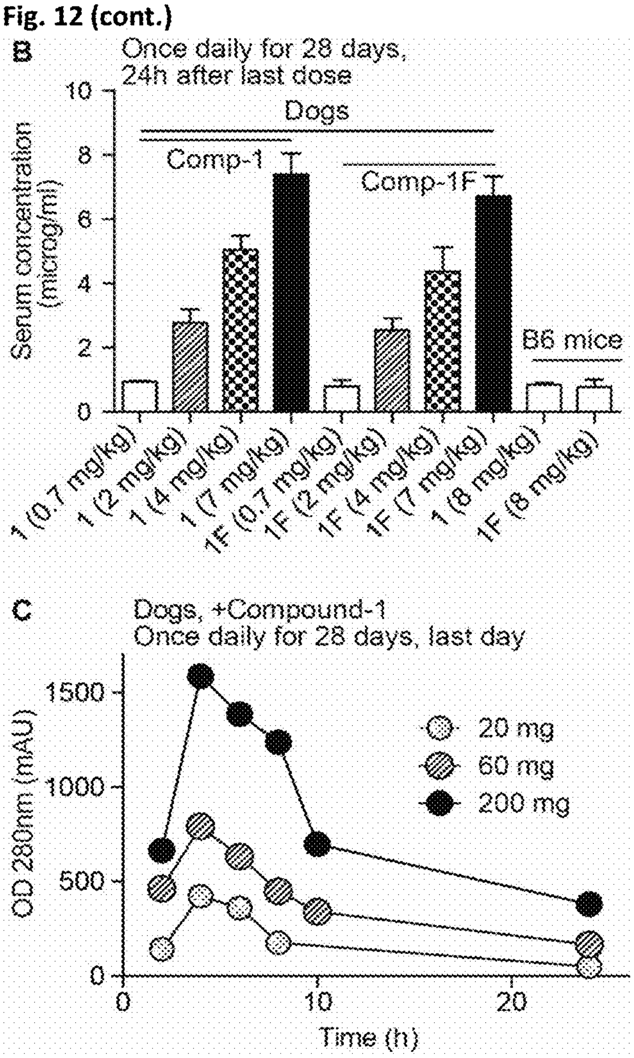

FIG. 12 shows by the measurement of the serum concentration that Compound-1 and Compound-1F have good oral bioavailability in dogs after oral treatment. (A) Time-dependent increase of Compound-1 in serum of dogs after oral gavage (at t=0) of a single dose of Compound-1 (60 mg and 200 mg as indicated). (B) Serum concentration after 28 days of repeated once daily oral dosing with 0.7 mg/kg, 2 mg/kg, 4 mg/kg, 7 mg/kg of Compound-1 and Compound-1F in dogs, and 8 mg/kg/d of Compound-1 and Compound-1F in B6 mice. Serum concentration was determined by HPLC at t=24 h after the last dose. (C) Time-dependent increase in serum concentration of Compound-1 after repeated 28 days of oral intake of indicated once daily doses (20 mg, 60 mg, 200 mg) of Compound-1. Serum was taken at the indicated time points after drug intake on day 28. The serum concentration (A,C) is given as OD 280 nm (mAU). During sample preparation for HPLC analysis, the serum sample was concentrated 10-fold. With this 10-fold concentration factor, and the calibration curve, the OD 280 nm was converted into the serum concentration (cf. B).

Figure 13:
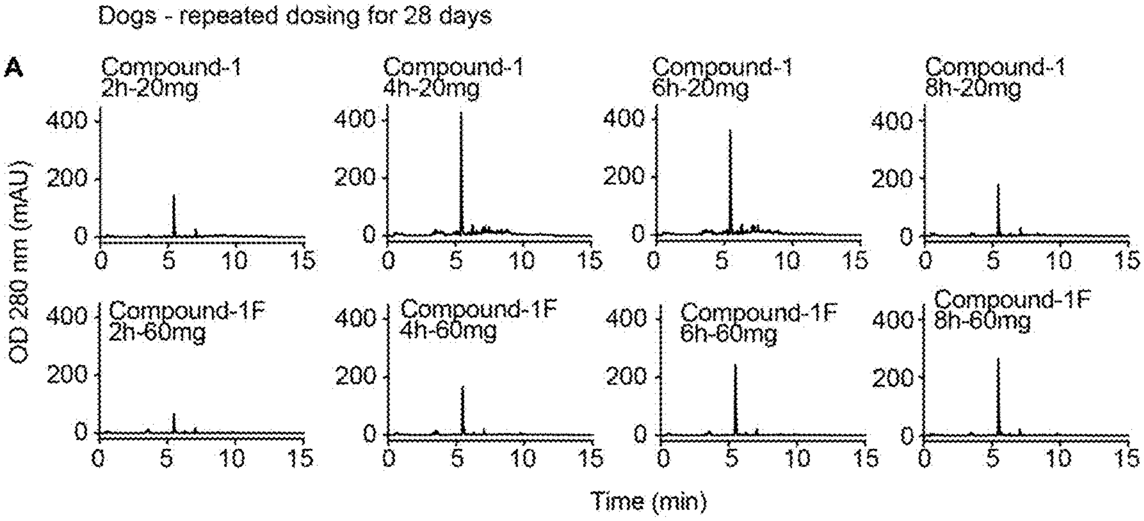
Figure 13:
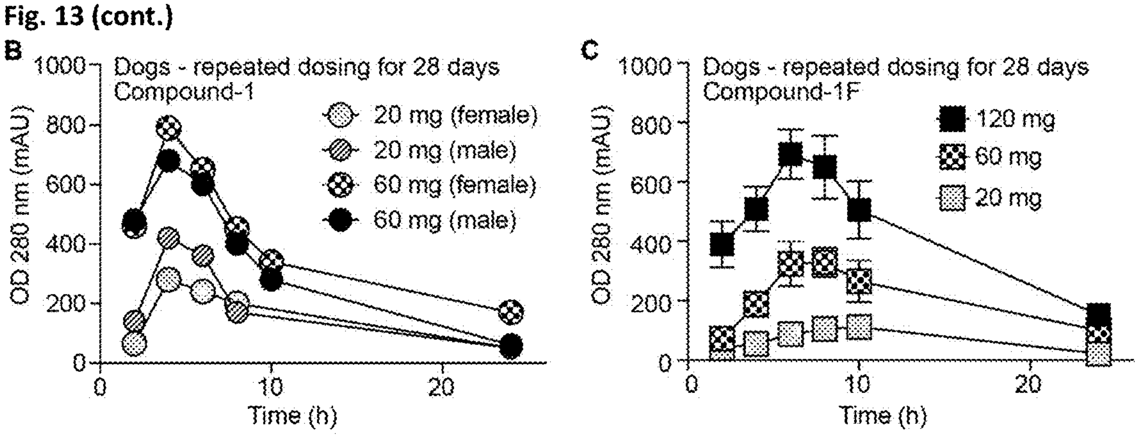

FIG. 13 shows different pharmacokinetics between Compound-1 and Compound-1F in dogs. (A) HPLC chromatograms of dog serum concentration of Compound-1 and Compound-1F. Dog serum was taken at different time points after oral intake of the indicated dose on day 28 after repeated once daily dosing for 28 days. (B,C) Concentration-time relationships of Compound-1 (B) and Compound-1F (C). Dog serum was taken at the indicated time points after oral drug intake of the indicated dose on day 28 after repeated once daily dosing for 28 days (C; ±s.d.; n=4 dogs per dose group; 2 male and 2 female dogs).

Figure 14:
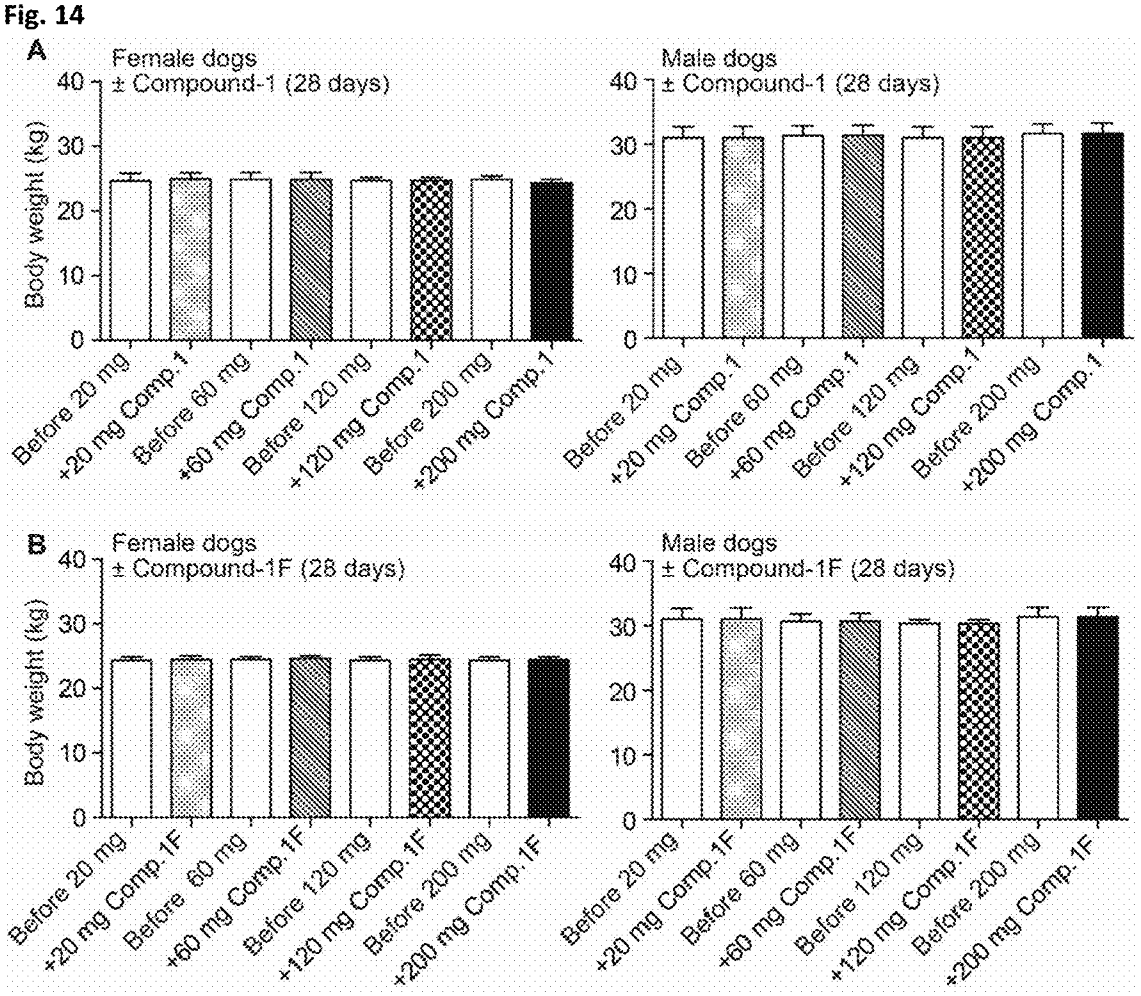

FIG. 14 shows that body weight of male and female dogs is not changed by treatment with Compound-1 and Compound-1F for 28 days. (A,B) Treatment of German shepherd dogs, for 28 days with Compound-1 (A), and Compound-1F (B) at a once daily dose of 20 mg, 60 mg, 120 mg and 200 mg did not significantly change body weight in male and female dogs (±s.d; n=3/group). Body weight was determined before the study and on day 28 after repeated once daily intake of the indicated dose for 28 days.

Figure 15:
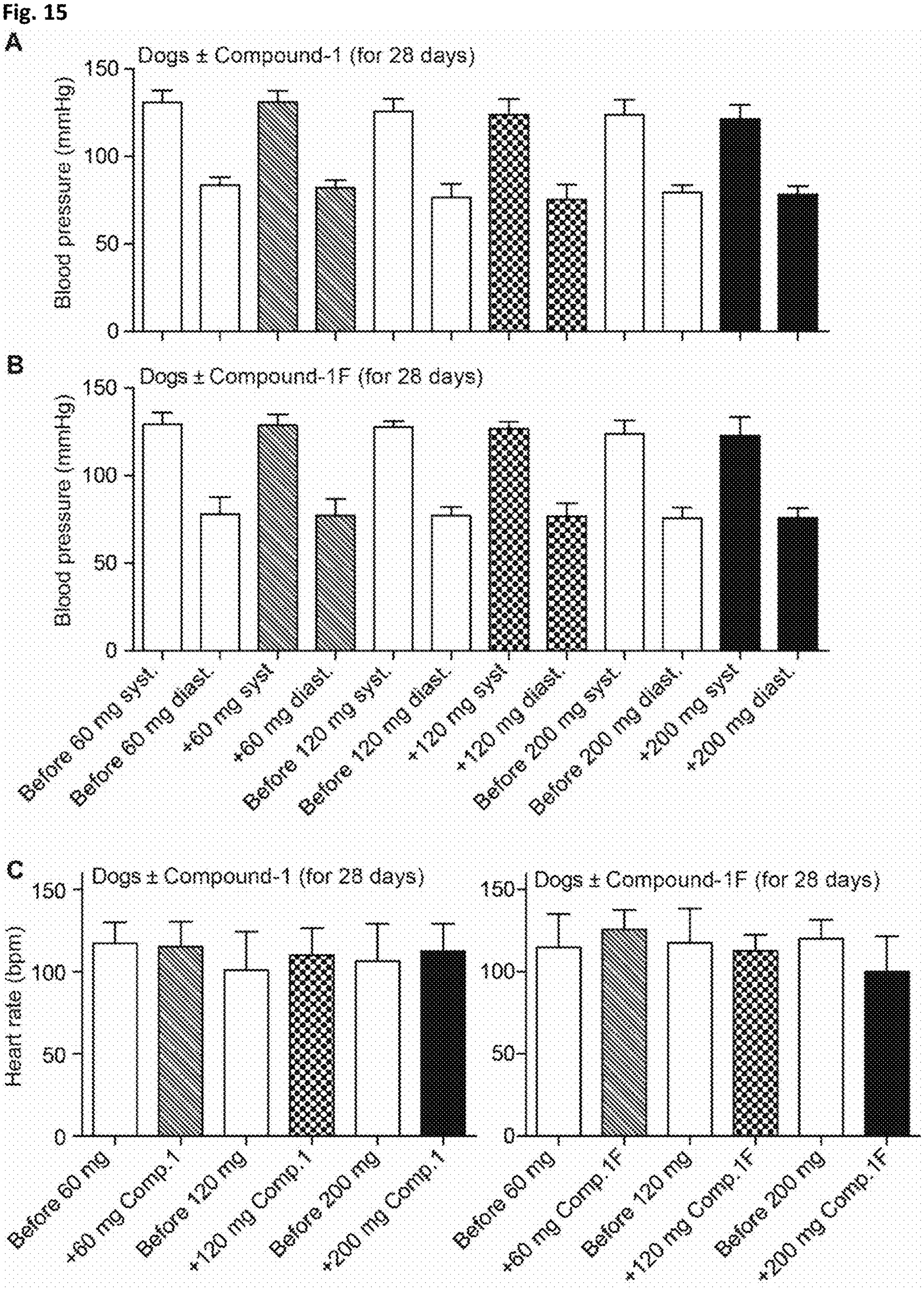

FIG. 15 shows that treatment with Compound-1 and Compound-1F for 28 days had no effect on blood pressure and heart rate of dogs. (A,B) Systolic and diastolic blood pressure of German shepherd dogs before and after 28 days of repeated once daily intake of Compound-1 (A), and Compound-1F (B) at a once daily dose of 60 mg, 120 mg and 200 mg. (C) Heart rate of study groups was determined during blood pressure measurement (±s.d.; n=4/group with 2 male and 2 female dogs per dose group).

Figure 16:
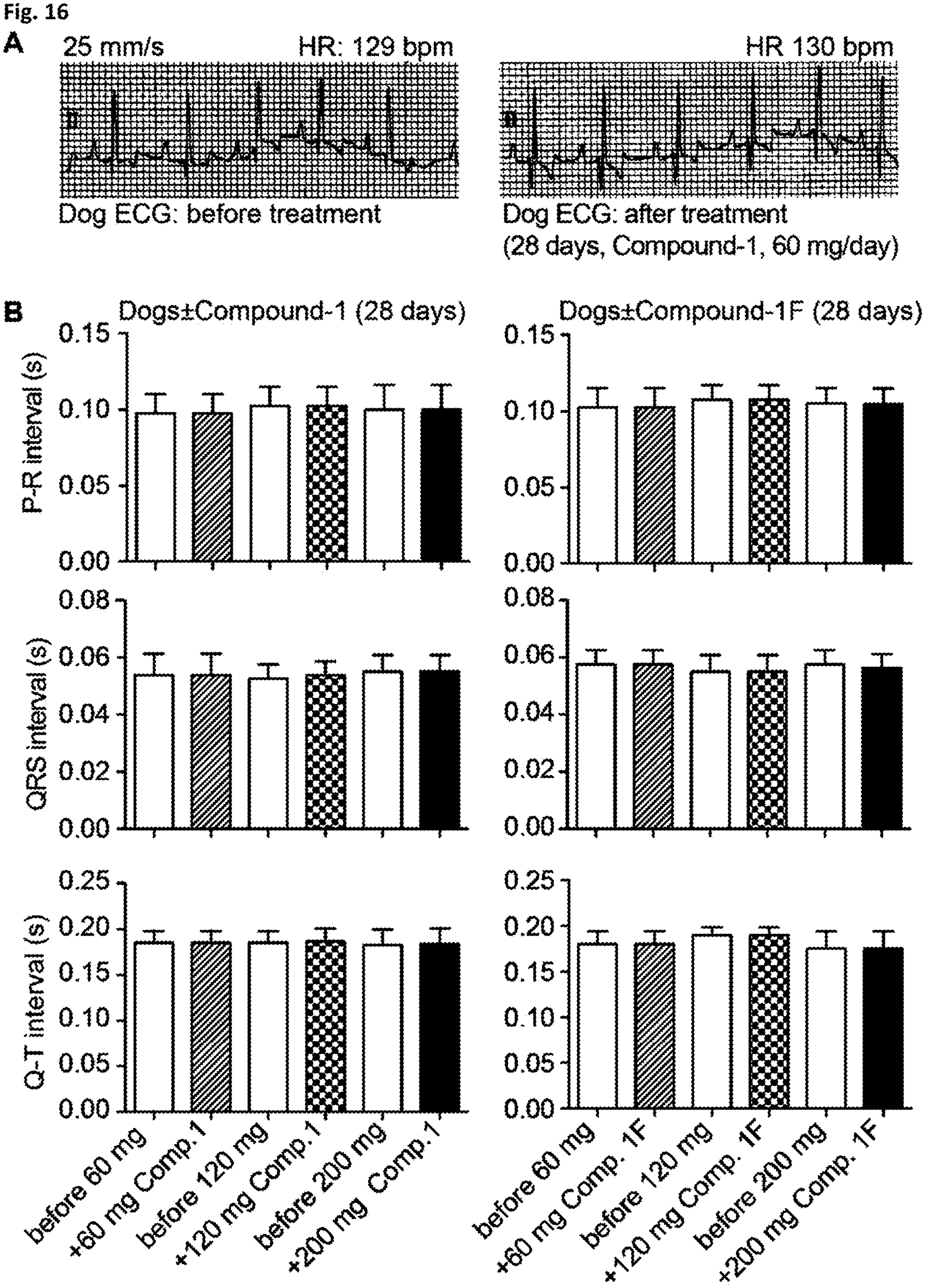

FIG. 16 shows that ECG parameters of dogs are not changed by treatment with Compound-1 and Compound-1F for 28 days. (A) Representative electrocardiograms before and after treatment with Compound-1 for 28 days at a once daily dose of 60 mg/day. (B) P-R interval (upper), QRS interval (middle) and Q-T interval (lower) were determined by an ECG recorded before and after oral treatment with Compound-1 (left panels) and Compound-1F (right panels) for 28 days at the indicated once daily dose (±s.d., n=4/group with 2 male and 2 female dogs per dose group).

Figure 17:
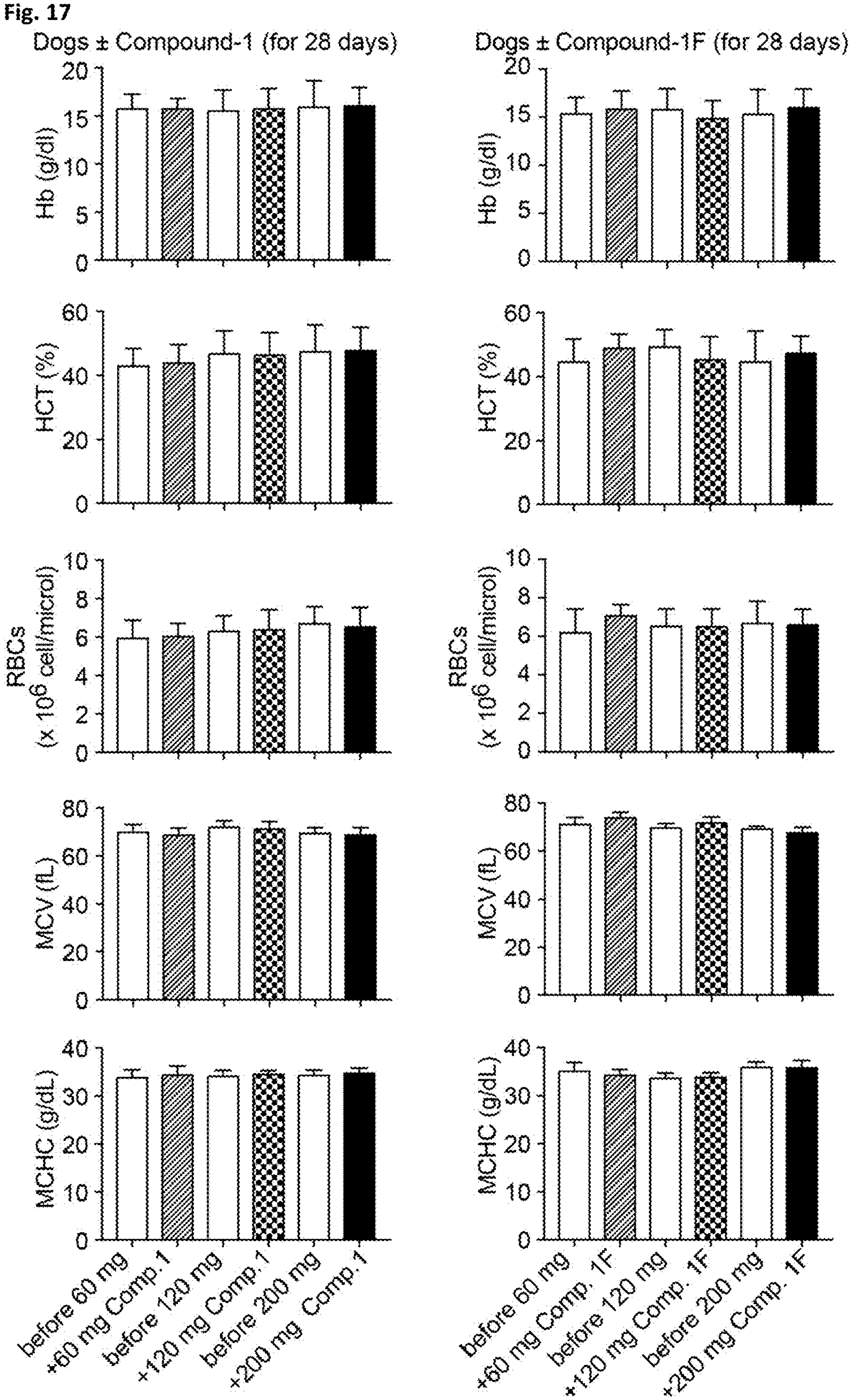

FIG. 17 shows that major hematologic parameters of dogs are not changed by treatment with Compound-1 and Compound-1F for 28 days. Hemoglobin (Hb), hematocrit (HCT), number of red blood cells (RBCs), mean corpuscular volume (MCV) and mean corpuscular hemoglobin concentration (MCHC) were determined before and after oral treatment with Compound-1 (left panels) and Compound-1F (right panels) for 28 days at a once daily dose of 60 mg/d, 120 mg/d and 200 mg/d (±s.d., n=4/group with 2 male and 2 female dogs per dose group).

Figure 18:
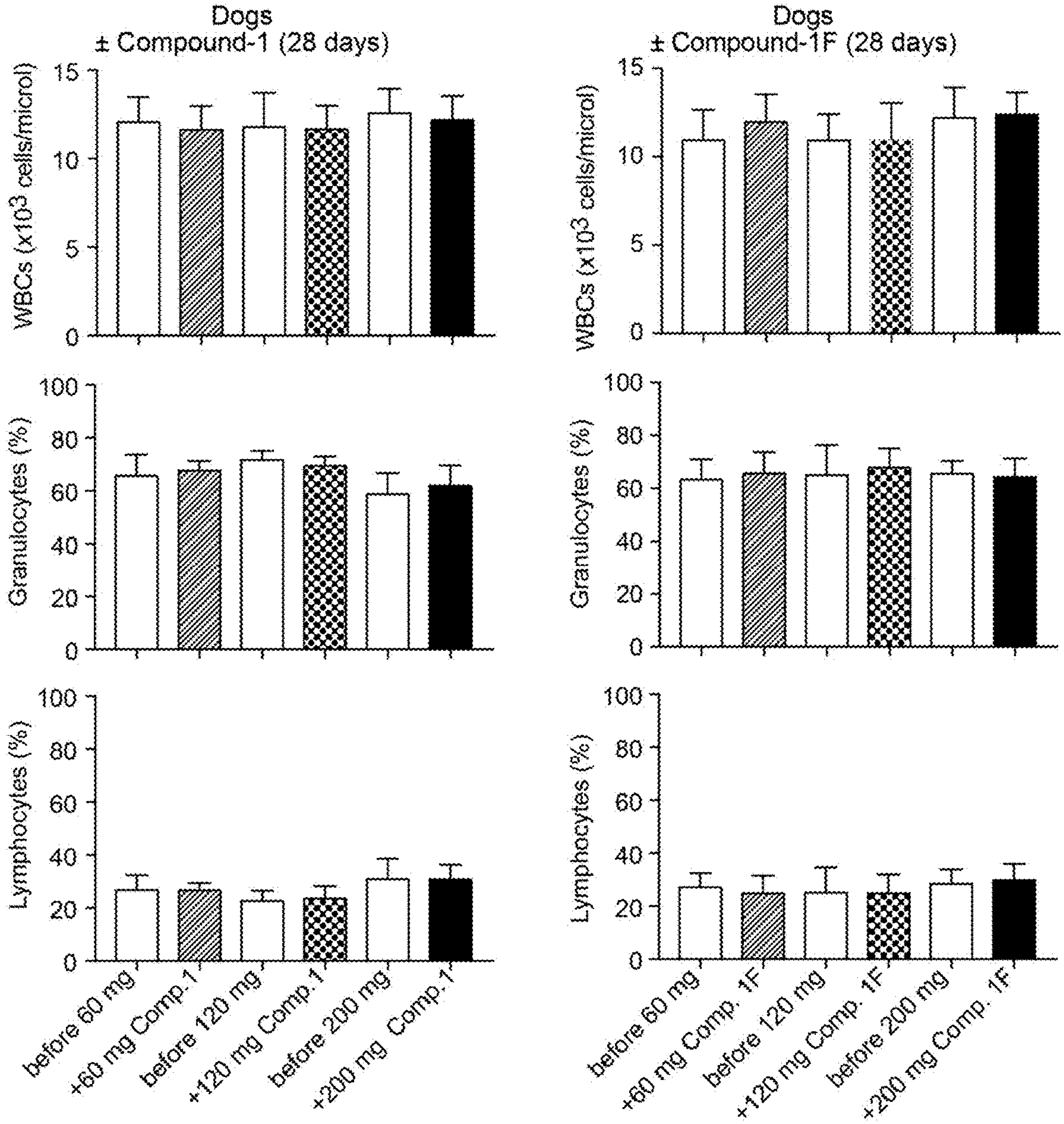

FIG. 18 shows that treatment of dogs with Compound-1 and Compound-1F does not significantly alter white blood cell number. The number of white blood cells and the percentage of granulocytes and lymphocytes was not significantly altered by treatment with Compound-1 and Compound-1F for 28 days. The leukogram was determined before and after oral treatment with Compound-1 (left panels) and Compound-1F (right panels) for 28 days at a once daily dose of 60 mg/d, 120 mg/d and 200 mg/d (±s.d., n=4/group with 2 male and 2 female dogs per dose group).

Figure 19:
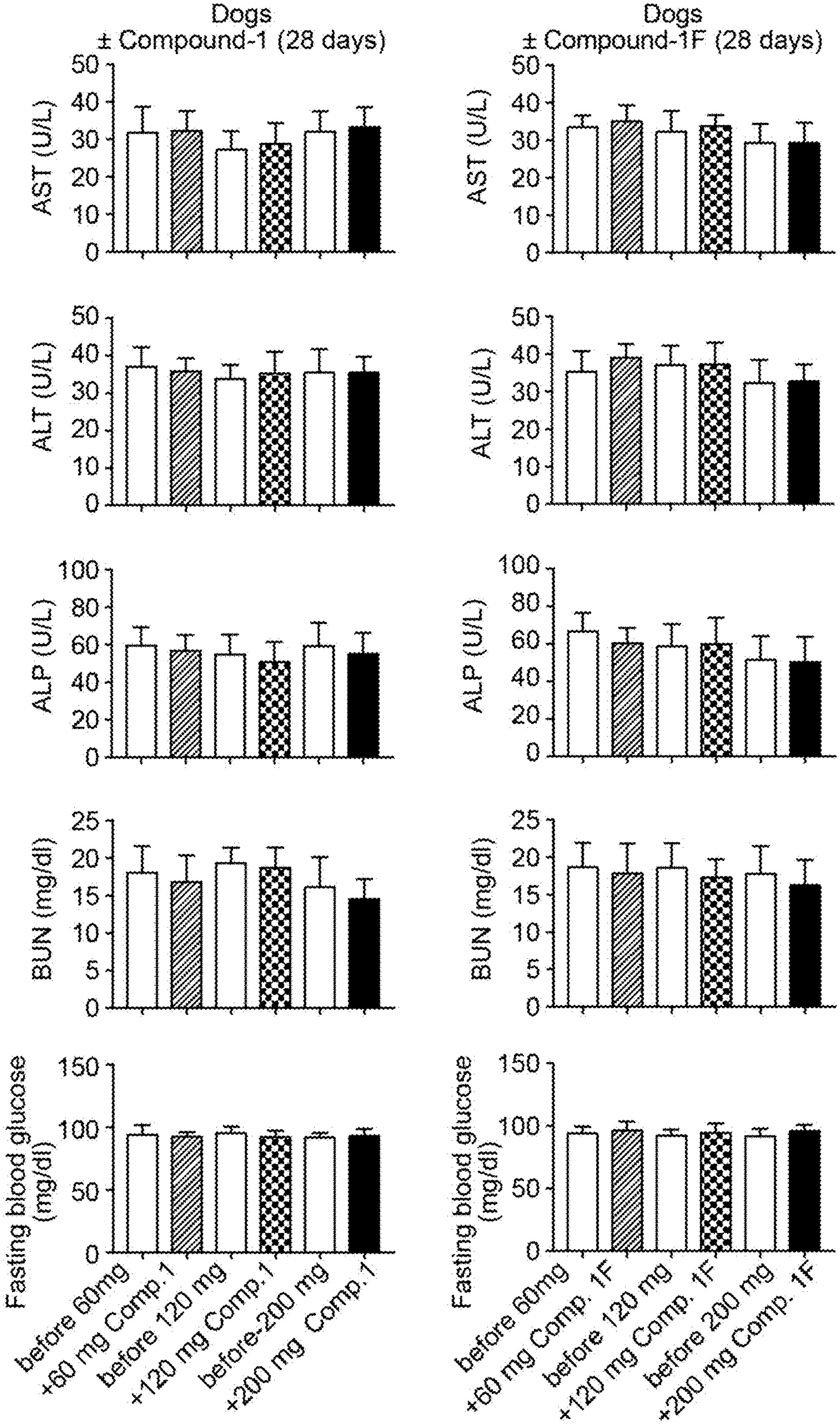

FIG. 19 shows that biochemical parameters of liver and kidney function are not changed in dogs after treatment with Compound-1 and Compound-1F for 28 days. Treatment with Compound-1 (left panels) and Compound-1F (right panels) for 28 days did not significantly alter blood levels of aspartate transaminase (AST), alanine transaminase (ALT), alkaline phosphatase (ALP), blood urea nitrogen (BUN) and fasting blood glucose. Biochemical parameters of liver and kidney function were determined before and after oral treatment with Compound-1 (left panels) and Compound-1F (right panels) for 28 days at a once daily dose of 60 mg/d, 120 mg/d and 200 mg/d (s.d., n=4/group with 2 male and 2 female dogs per dose group).

Figure 20:
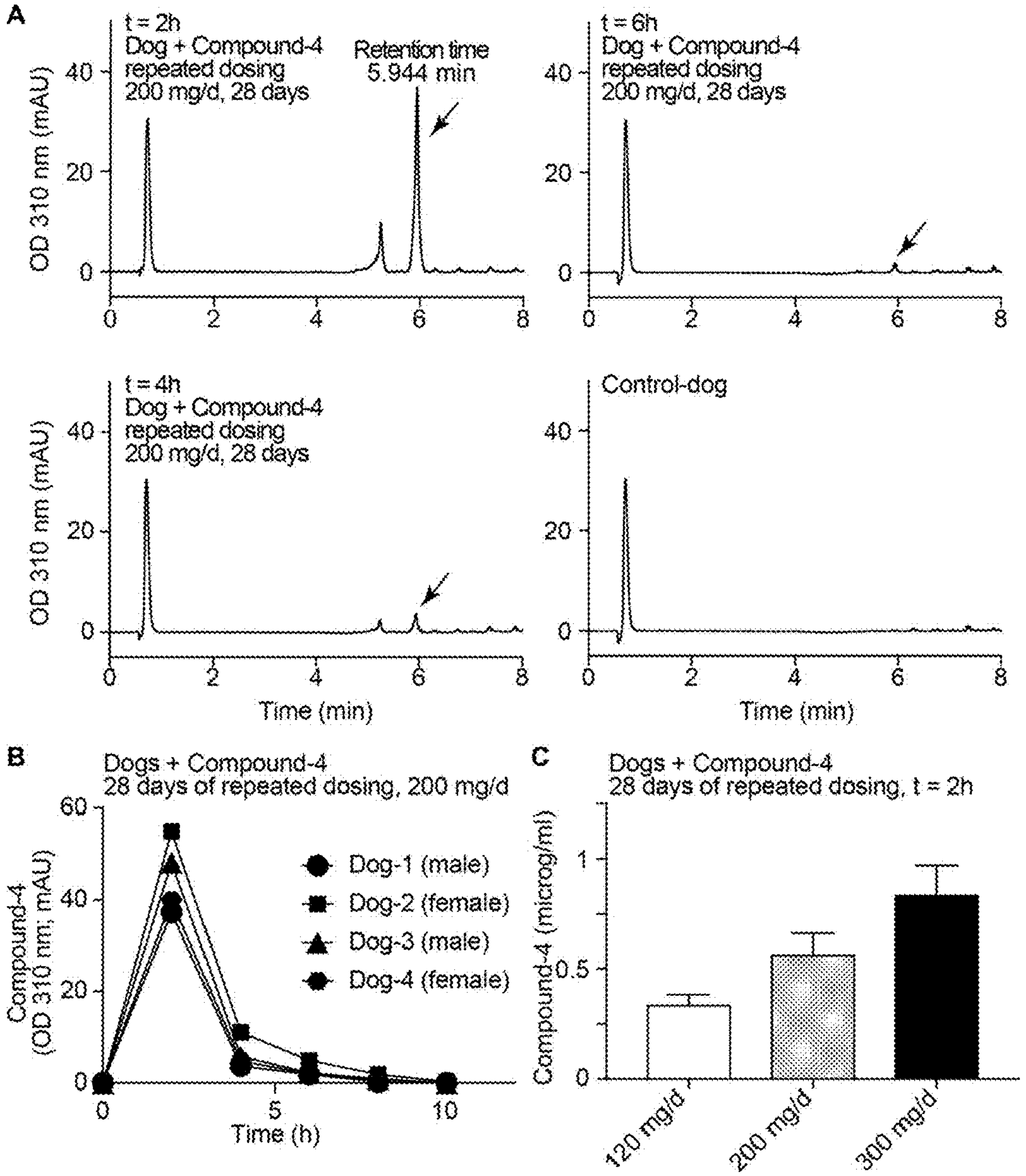

FIG. 20 shows the oral bioavailability of Compound-4 in dogs. (A) Representative HPLC chromatograms of determination of Compound-4 in serum of a dog after 28 days of repeated oral intake of 200 mg per day. Serum samples were taken at t=2 h, 4 h, and 6 h after intake of 200 mg of Compound-4 on day 28. The concentration of Compound-4 in the 10-fold concentrated serum sample was determined by HPLC and is given as OD 310 nm (mAU). The lower right panel is a HPLC chromatogram from a control dog receiving placebo. (B) Concentration-time relationships of Compound-4 in serum of dogs were determined after 28 days of repeated oral dosing of Compound-4 at a once daily dose of 200 mg. Serum samples were taken at the indicated time points after the intake of 200 mg of Compound-4 on day 28 (±s.d., n=4 dogs). (C) Peak serum concentration of Compound-4 in dogs after 28 days of repeated once daily dosing with 120 mg/d, 200 mg/d and 300 mg/d was determined on day 28 at 2 h after the last drug intake (±s.d., n=4 dogs per dose group, 2 male and 2 female dogs).

Figure 21:
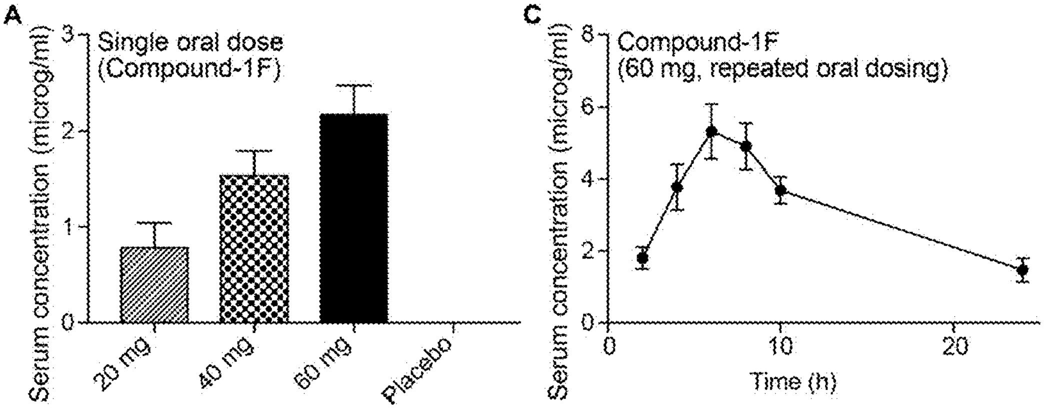
Figure 21:
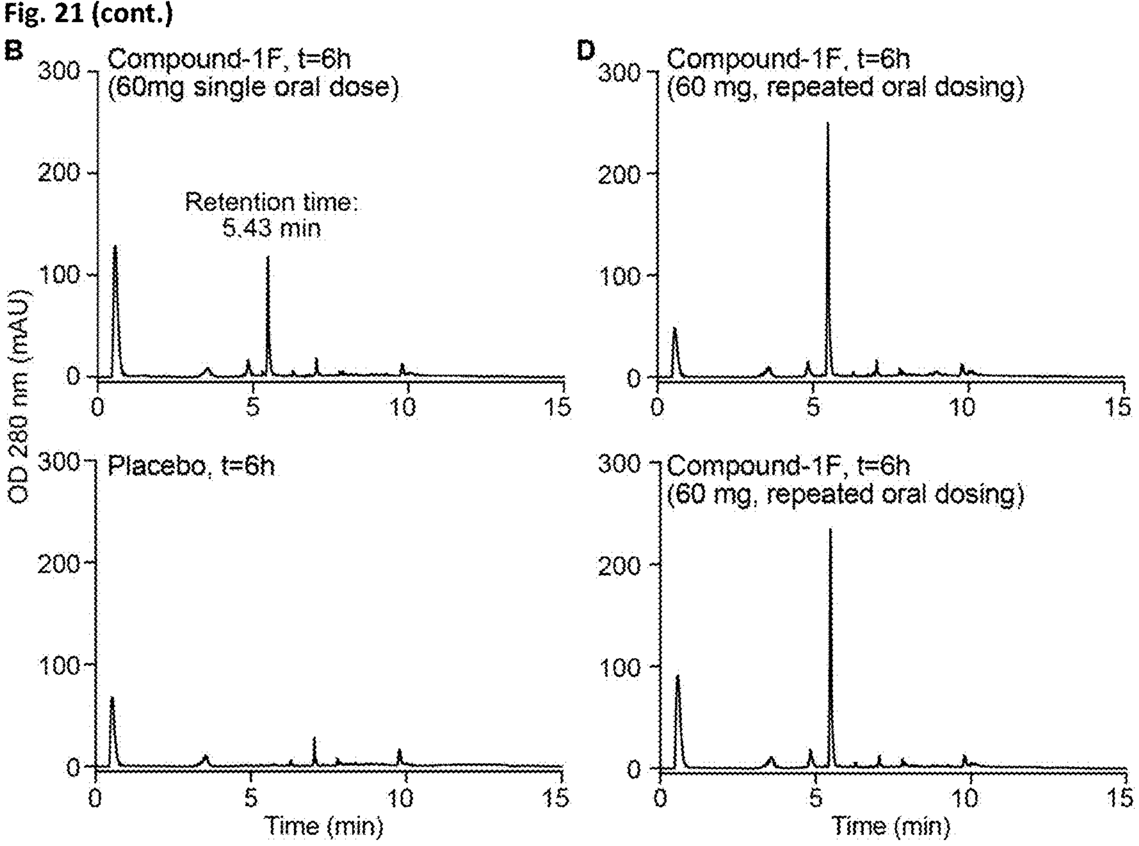

FIG. 21 shows the determination of serum concentration of healthy human research participants after single and repeated oral dosing of Compound-1F. (A) Serum concentration of Compound-1F was determined in healthy human research participants 6 h after a single oral dose of Compound-1F of 20 mg, 40 mg and 60 mg (±s.d., n=3; 2 males, 1 female). (B) Representative HPLC chromatogram of Compound-1F quantification in serum from a research participant 6 h after a single oral dose of 60 mg of Compound-1F (upper). Compound-1F was absent in serum from the placebo-treated participant (lower). (C) Concentration-time relationship of Compound-1F in sera from research participants after repeated oral dosing of Compound-1F at a once daily dose of 60 mg. Serum was taken at the indicated time points after the last drug intake (±s.d., n=8; 6 males and 2 females). (D) Representative HPLC chromatograms of Compound-1F in sera of two different healthy research participants at 6 h after the last drug intake after repeated oral dosing of Compound-1F at a once daily dose of 60 mg. During sample preparation for HPLC analysis, the serum sample was concentrated 10-fold. With this 10-fold concentration factor, and the calibration curve, the OD 280 nm was converted into the serum concentration as shown in (A,C).

Figure 22:
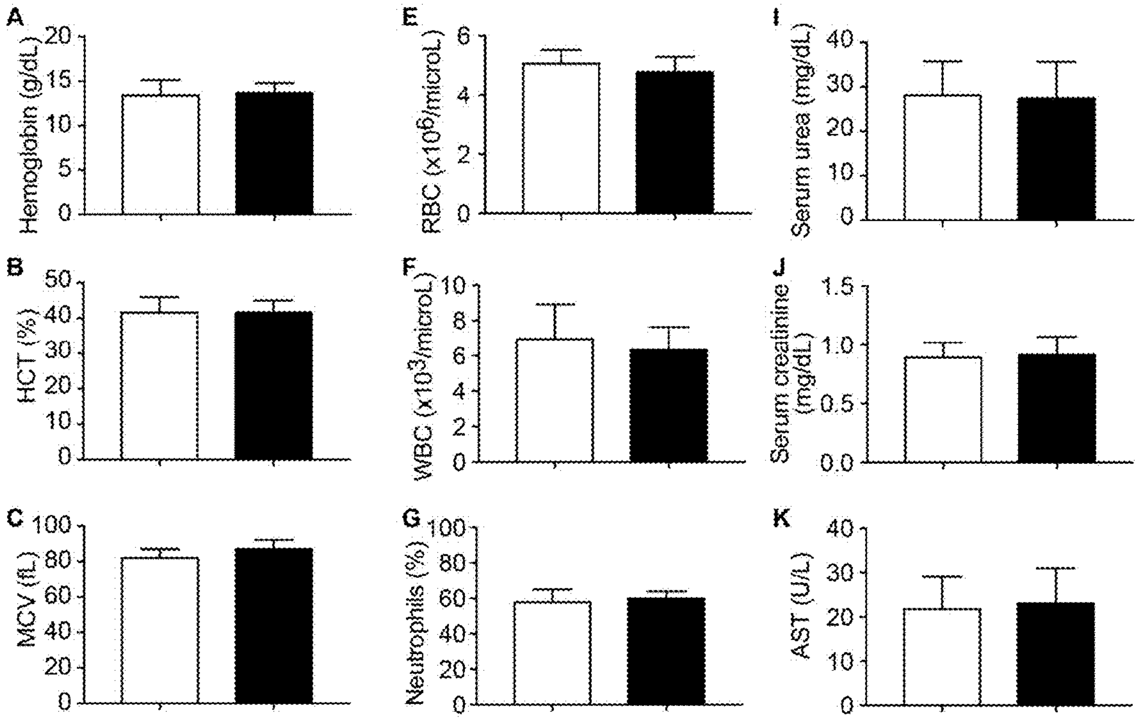
Figure 22:
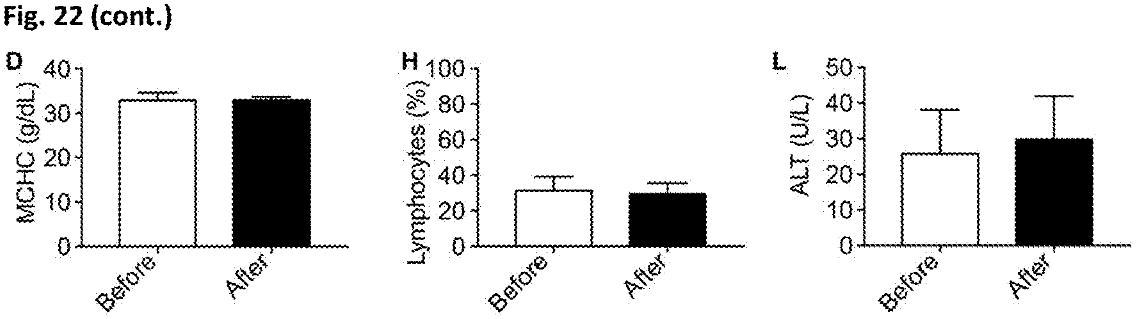

FIG. 22 shows normal hematologic parameters, white blood cell count, and liver and kidney function parameters in healthy human research participants after repeated oral dosing of Compound-1F. (A-L) Clinical laboratory parameters of healthy human research participants were determined before and after repeated dosing of Compound-1F at a once daily dose of 60 mg. Values of hemoglobin (Hb, A), hematocrit (HCT, B), mean corpuscular volume (MCV, C), mean corpuscular hemoglobin concentration (MCHC, D), number of red blood cells (RBCs, E), number of white blood cells (WBC, F), neutrophils (G), lymphocytes (H), serum urea (I), serum creatinine (J), aspartate transaminase (AST, K), and alanine transaminase (ALT, L) were within the normal range and not significantly different before and after repeated oral dosing of Compound-1F at a once daily dose of 60 mg (±s.d., n=8; 6 males and 2 females).

Figure 23:
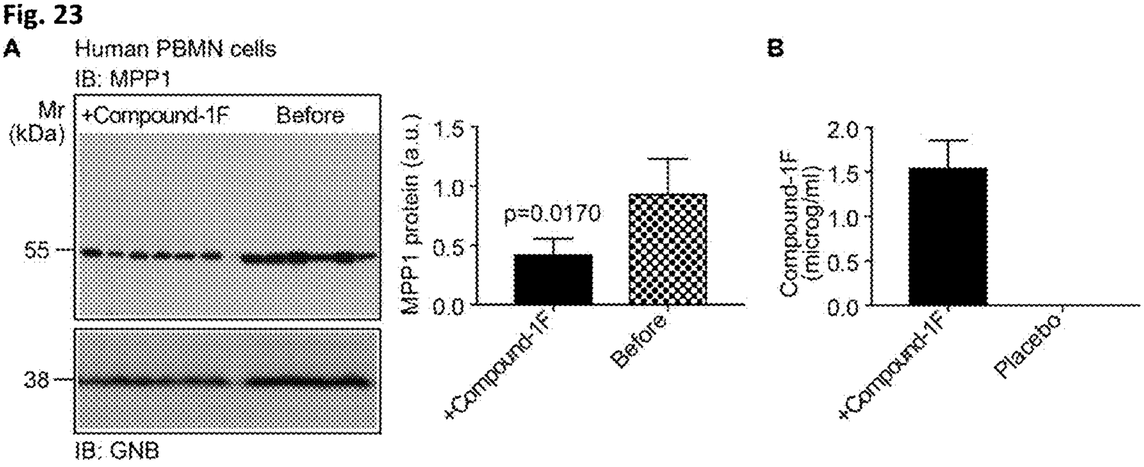

FIG. 23 shows the down-regulation of the senescence-promoting peripheral blood mononuclear cell marker, MPP1, after treatment of elderly human research participants with Compound-1F for 28 days. (A) Immunoblot detection of peripheral blood mononuclear (PBMN) cell content of MPP1 of elderly human research participants before and after treatment with Compound-1F for 28 days at a once daily dose of 60 mg. The left panel shows immunoblot detection of MPP1, and the right panel shows quantitative data (±s.d. n=6; 6 males; p=0.0170; paired, two-tailed Student's t-test). (B) Steady state serum concentration of Compound-1F after 28 days of repeated oral dosing of Compound-1F at a once daily dose of 60 mg (±s.d., n=6+ Compound-1F, 6 males; n=2 placebo, one male, one female). Serum was taken 24 h after the last drug intake on day 28 of the study.

EXAMPLES

Materials and Methods

Compound Synthesis

Compounds for use in the present invention can and were synthesized by routine adaption of standardized protocols, for example, were synthesized by EMC microcollections GmbH, Tuebingen, Germany and ChiroBlock GmbH, Wolfen, Germany. The synthesis of such compounds was performed in a small scale by solid phase chemical synthesis methods, which were adapted from established protocols (For "Compound-1" (1-(1,3-benzodioxol-5-yl)-4-(cyclopropane-carbonyl)-3-hydroxy-2-phenyl-2H-pyrrol-5-one): Poncet J, et al., J. Chem. Soc. Perkin Trans I., 611-616 (1990); for "Compound-2" (1-(1,3-benzodioxol-5-ylmethyl)-5-(4-fluorophenyl)-2-methyl-pyrrole-3-carboxamide), "Compound-22" (1-(1,3-benzodioxol-5-ylmethyl)-2-methyl-5-phenyl-pyrrole-3-carboxamide), "Compound-23" (1-(1,3-benzodioxol-5-ylmethyl)-2-methyl-5-(p-tolyl)pyrrole-3-carboxamide), and "Compound-24" (1-(1,3-benzodioxol-5-ylmethyl)-5-(4-chlorophenyl)-2-methyl-pyrrole-3-carboxamide): Trautwein A W, et al., Bioorg. Med. Chem. Lett. 8, 2381-2384 (1998); for Compound-3: Sakai K, et al., Chem. Pharm. Bull. 29(6) 1554-1560 (1981); for "Compound-4": Coombs T C, et al., Bioorg. Med. Chem. Lett. 23, 3654-3661 (2013); and for "Compound-5" ((4R)—N3-(1,3-benzodioxol-5-ylmethyl)-N4-[[3-(trifluoromethyl)phenyl]-methyl]pyrrolidine-3,4-dicarboxamide): Baber J C, et al., Bioorg. Med. Chem. 20, 3565-3574 (2012)). In addition, Compound-1 and Compound-4 were synthesized in a larger scale as detailed below.

Synthesis of Compound-1

Synthesis of Compound-1 (1-(1,3-Benzodioxol-5-yl)-4-(cyclopropanecarbonyl)-3-hydroxy-2-phenyl-2H-pyrrol-5-one) was performed by a 6-step chemical reaction process (ChiroBlock GmbH, Wolfen, Germany). Step-1 encompassed the synthesis of methyl 2-(1,3-benzodioxol-5-ylamino)-2-phenyl-acetate. A mixture of methyl 2-oxo-2-phenyl-acetate (96 g, 584 mmol, 4.0 equivalents), 1,3-benzodioxol-5-amine (20 g, 146 mmol, 1.0 equivalents), and $Na_2SO_4$ in cyclohexane (800 ml) was refluxed under $N_2$ for 21 h. 5% Pd/C (7.8 g) was added, and the obtained suspension was hydrogenated at 20 bar and 20° C. for 48 h. The resulting heterogeneous mixture was diluted with EtOAc (ca. 800 ml) and filtered through Celite. The filtrate was concentrated in vacuo (40° C., 100 mbar) to yield a brown oil (135 g) that was purified by flash chromatography (silica gel, ethyl acetate-petroleum ether 12:88 to 30:70) to yield target 3, which was an off-white solid (18.46 g; purity 95%, yield 44%).

Step-2 was the synthesis of S-tert-butyl ethanethioate. A solution of pyridine (87.0 g, 1.1 mol, 1.1 equivalents) in chloroform (800 ml) was cooled in an ice bath and treated with acetyl chloride (86.4 g, 1.1. mol, 1.1 equivalents), with the reaction temperature not exceeding 11° C. To the resulting orange suspension, 2-methylpropane-2-thiol (90.2 g, 1.0 mol, 1.0 equivalents) was dropwise added over 40 min., and the mixture was stirred for 48 h and subsequently quenched with water (500 ml). The phases were separated and the aqueous phase was extracted with chloroform (400 ml). The combined organic extracts were washed with 400 ml each of water, 10% $H_2SO_4$, sat. $NaHCO_3$, and water being subsequently dried over $Na_2SO_4$. The obtained chloroformic solution was subjected to fractional distillation, which afforded target S-tert-butyl ethanethioate as a clear liquid (55.8 g, purity 95%, yield 45%).

In Step-3 the synthesis of S-(2-pyridyl) cyclopropanecarbothioate was performed. Cyclopropanecarbonyl chloride (23.5 g, 225 mmol, 1.0 equiv.) was dropwise added to solution of pyridine-2-thiol (25.0 g, 225 mmol, 1.0 equiv.) in THE (250 ml) at 20° C. The mixture was stirred for 10 min, filtered, and the filter cake was washed with 1:4 $Et_2O$/petrol ether (250 ml). The thus obtained solid was dissolved in water (250 ml) and treated with $NaHCO_3$ (19 g, 225 mmol, 1.0 equiv.), and the aqueous solution was extracted with 2*250 ml EtOAc. The combined organic fractions were dried over $Na_2SO_4$ and concentrated in vacuo to afford S-(2-pyridyl) cyclopropanecarbothioate as a yellow oil (37 g, purity 95%; yield 92%).

Step-4 was the synthesis of S-tert-butyl 3-cyclopropyl-3-oxo-propanethioate. A 2-L 3-neck round-bottom flask was charged with HMDS (83.3 g, 516 mmol, 2.5 equiv) and freshly distilled THE (800 ml). The obtained mixture was cooled in an acetone/dry ice bath, and 1.6 M nBuLi in hexanes (323 ml, 516 mmol, 2.5 equiv.) was dropwise added while keeping the temperature below −50° C. Subsequently, the obtained mixture was sequentially treated with solutions of S-(2-pyridyl) cyclopropanecarbothioate (37.0 g, 206 mmol, 1.0 equiv.) and S-tert-butyl ethanethioate (23.4 g, 214 mmol, 1.04 equiv.). The obtained solution was stirred for 1 h at −30° C., and the reaction was quenched (under TLC process control) by 1 N $H_2SO_4$ (800 ml). The resulting suspension was extracted with EtOAc (3*900 ml), and the organic fractions combined, washed with brine (2 L), dried over $Na_2SO_4$, and concentrated in vacuo. The crude product was purified by flash chromatography (silica gel, ethyl acetate-petroleum ether 25:75) to yield target S-tert-butyl 3-cyclopropyl-3-oxo-propanethioate as a brown oil (29.5 g, purity 83%, yield: 59%).

In Step-5, the synthesis of Methyl 2-[1,3-benzodioxol-5-yl-(3-cyclopropyl-3-oxo-propanoyl)amino]-2-phenyl-acetate was performed. A 1-L round-bottom flask was charged with Methyl 2-(1,3-benzodioxol-5-ylamino)-2-phenyl-acetate (18.5 g, 61 mmol, 1.0 equiv.), S-tert-butyl 3-cyclopropyl-3-oxo-propanethioate (15.9 g, 66 mmol, 1.073 equiv.), $CF_3COOAg$ 814.6 g, 66 mmol, 1.073 equiv.), and distilled THE (400 ml), and the obtained mixture was stirred at 20° C. for 36 h (the process was controlled by TLC). The dark-brown reaction mixture was concentrated in vacuo and purified by flash chromatography (silica gel, ethyl acetate-petroleum ether 25:75 to 50:50) to yield target Methyl 2-[1,3-benzodioxol-5-yl-(3-cyclopropyl-3-oxo-propanoyl) amino]-2-phenyl-acetate as a brown oil (21.0 g, purity: 90%, yield: 78%).

The final Step-6 yielded the final target 1-(1,3-Benzodioxol-5-yl)-4-(cyclopropanecarbonyl)-3-hydroxy-2-phenyl-2H-pyrrol-5-one (Compound-1). A 500 ml round-bottom flask was charged with Methyl 2-[1,3-benzodioxol-5-yl-(3-cyclopropyl-3-oxo-propanoyl)amino]-2-phenyl-acetate (20.0 g; 45.5 mmol, 1.0 equiv.), CsF (6.9 g, 45.5. mmol, 1.0 equiv.), and DMF (140 ml), and the obtained mixture was stirred at 60° C. for 20 h (the process was controlled by TLC). The dark-brown reaction mixture was concentrated in vacuo and the residue was treated with 1N $H_2SO_4$ (400 ml). The obtained mixture was extracted with EtOAc (500 ml), and the organic phase was washed with brine (2*300 ml), dried over $Na_2SO_4$, and concentrated in vacuo to afford crude 1-(1,3-Benzodioxol-5-yl)-4-(cyclopropanecarbonyl)-3-hydroxy-2-phenyl-2H-pyrrol-5-one as a brown solid (19 g). The above solid was washed on filter with EtOAc until becoming colorless, affording target Compound-1 (1-(1,3-Benzodioxol-5-yl)-4-(cyclopropanecarbonyl)-3-hydroxy-2-phenyl-2H-pyrrol-5-one) as an off-white solid (5.0 g, purity: 98%, yield: 30%).

Synthesis of Compound-1F

Compound-1F (1-(1,3-Benzodioxol-5-yl)-4-(cyclopropanecarbonyl)-2-(4-fluorophenyl)-3-hydroxy-2H-pyrrol-5-one; $C_{21}H_{16}FNO_5$; MW 381.36; formula in FIG. 5A) is a derivative of Compound-1 (1-(1,3-Benzodioxol-5-yl)-4-(cyclopropanecarbonyl)-3-hydroxy-2-phenyl-2H-pyrrol-5-one; $C_{21}H_{17}NO_5$; MW 363.37).

Synthesis of Compound-1F was performed by Chiroblock (Wolfen, Germany), as described in the related patent application WO/2018/130537 (PCT/EP2018/050504) with minor modifications, i.e. synthesis step-1 (FIG. 13I of WO/2018/130537) used methyl 2-(4-fluorophenyl)-2-oxo-acetate instead of methyl 2-oxo-2-phenyl-acetate.

Methyl 2-(4-fluorophenyl)-2-oxo-acetate was synthesized as follows: To a 2 L three neck round-bottom flask were added magnesium (1.5 equiv., 25.0 g, 1.03 mol), iodine (0.01 equiv., 0.9 g, 0.007 mol) and 0.78 L of anhydrous THE. The mixture was degassed with $N_2$ and vacuum three times. With stirring, the reaction mixture was heated to reflux until yellow colour disappeared. A solution of 4-bromofluorobenzene (1 equiv., 120 g, 0.68 mol) in 0.1 L of THE was added dropwise at a speed to keep the reaction refluxing. After addition completed, the reaction was kept stirring for 1 h, then cooled to rt. In another flask (4 L three neck round-bottom flask), a solution of dimethyl oxalate (1.15 equiv., 93.1 g, 0.79 mol) in anhydrous THE (0.9 L) was cooled to −78° C. The Grignard solution obtained above was added dropwise to the dimethyl oxalate solution. The reaction mixture was stirred at −78° C. for 1 h. The reaction mixture was added to saturated aqueous $NH_4Cl$ solution (1 L) and extracted with EtOAc (3×0.5 L). The combined organic layers were dried over anhydrous $Na_2SO_4$ and filtered. The filtrate was concentrated in vacuo to give the crude product that was purified by flash chromatography ($SiO_2$, eluting with EtOAc:petrol ether 1:7) to yield target methyl 2-(4-fluorophenyl)-2-oxo-acetate, which was a yellow solid (67 g, purity: 95%, yield: 54%).

Synthesis of Compound-4

Compound-4 (4-(1,3-Benzodioxol-5-yl)pyrimidine) was synthesized by the following procedure (ChiroBlock GmbH, Wolfen, Germany). A 250 ml round-bottom flask was loaded with 1-(1,3-Benzodioxol-5-yl)ethanone (10.0 g, 60.9 mmol, 1.0 equivalent), $(EtO)_3CH$ (27 g, 183 mmol, 3.0 equivalents), $ZnCl_2$ (0.83 g, 6.1 mmol, 0.1 equivalent), NH4CH3COO (0.4 g, 122 mmol, 2.0 equivalents) and toluene (120 ml), and the obtained mixture was stirred at reflux for 48 g and subsequently at 20° C. for 48 h (the process was controlled by TLC). The reaction mixture was quenched with saturated $NaHCO_3$ (400 ml) and extracted with chloroform (400 ml). The organic phase was dried over Na2SO4 and concentrated in vacuo, and the resulting crude product was purified by flash chromatography (silica gel, MeOH—$CHCl_3$ (0:100 to 5:95) to yield target Compound-4 (4-(1,3-Benzodioxol-5-yl)pyrimidine) as an off-white solid (3.0 g, purity 97%; yield 25

Animal Models

For a genetic model of familial AD (FAD), Tg2576 mice (Taconic Biosciences, Rensselaer, NY, USA) were used with neuron-specific overexpression of human APPSwe, i.e the Swedish mutation of APP695 isolated from a Swedish family with FAD featuring the double mutation K670N/M671L (Hsiao et al., Science 274, 99-103 (1996)). As a genetic model of tauopathy, the Tg-TauP301L mice (Model 2508, Taconic Biosciences, Rensselaer, NY, USA) with neuron-specific expression of the most common FTDP-17 (frontotemporal dementia and parkinsonism linked to chromosome 17) mutation (Lewis et al., Nature Genetics 25, 402-405 (2000)) were used. To enhance neurodegeneration and neuronal loss, the CUMS (chronic unpredictable mild stress) protocol was performed with male 12 months-old Tg2576 mice for 3 months essentially as described (AbdAlla et al., J. Biol. Chem. 284, 6554-6565 (2009); AbdAlla et al., J. Biol. Chem. 284, 6566-6574 (2009)).

As a model for reproducing major features of sporadic AD and depression, 15 months-old male rats were aged according to the CUMS protocol for 4 weeks. The following stimuli were administered each week in a random order: two periods (7 h and 17 h) of 45° cage tilt; soaked cage for 17 h; food deprivation (24 h) and water deprivation (12 h), twice a week; paired housing (17 h); overnight illumination during the dark phase, twice a week; noise (85 dB) in the room for 5 h, twice a week; flashing light (60 flashes/min) for 6 h, three times a week (AbdAlla et al., Biomed. Res. Int. 2015:917156 (2015); El-faramawy et al., Pharmacol. Biochem. Behav. 91, 339-344 (2009)). The sucrose preference test (2% sucrose in water) was done immediately after a period of food and water deprivation. After four weeks of stress, more than 90% of untreated stressed rats showed signs of anhedonia, which was documented by a decreased sucrose consumption in the sucrose preference test (≤50% compared to non-stressed age-matched control group and/or the stressed group treated with Compound-1 and Compound-4).

As indicated, representative compounds (Compound-1 and Compound-4; (8 mg/kg body weight/d) were added to drinking water or applied by oral gavage. Treatment of the Tg2576 model was performed for three and six months starting at an age of 12 months. Treatment of the Tg-TauP301L model was started at an age of 6 months and continued until 12 months. Aged 15 months-old rats were treated during the CUMS protocol. All mice/rats were kept on a light/dark cycle of 12 h light/12 h dark, had free access to food and water (unless the CUMS protocol required a restriction) and were fed a standard rodent chow. At the end of the observation period, mice or rats were anesthetized with tribromoethanol (250 mg/kg; i.p.) or urethane (1 g/kg, i.p.), perfused intracardially with sterile PBS, and brains were isolated, and processed for histology or biochemical analyses. For protein extraction, hippocampi were dissected and immediately frozen in liquid nitrogen. All animal experiments were performed in accordance with NIH guidelines and approved by the local committees on animal experiments (Univ. Zurich and MRC Cairo).

Antibodies

The following antibodies were used for immunoblotting and/or immunohistology: Abeta plaques were stained with monoclonal mouse antibody BAM-10 (crossreactive with residues 1-12 of the Abeta peptide, Sigma-Aldrich, St. Louis, MO, USA); PHF-Tau was detected with monoclonal AT8 antibody (MN1020; Thermo Fisher Scientific, Waltham, MA, USA); mouse monoclonal anti-NeuN antibody was raised against the neuron-specific protein NeuN (MAB377, clone A60, EMD Millipore, Merck KGaA, Darmstadt, Germany).

Immunohistochemistry

For Abeta plaque load quantification by immunohistochemistry, paraffin-embedded brain sections (or cryosections) (8 microm, 10-15 sections/brain taken at 30-50 microm intervals) were prepared from brains isolated from 18-month-old Tg2576 mice (Taconic Biosciences, Rensselaer, NY, USA) treated for six months without and with Compound-1 and Compound-4 (8 mg/kg body weight/day in drinking water). After antigen retrieval by microwave heating for 30 min in antigen retrieval buffer (10 mM sodium citrate, pH 6.0 supplemented with 0.05% Tween-20), sections were washed with PBS, and endogenous peroxidases were inactivated by incubation for 5 min in 3% H2O2 solution. After washing with PBS, brain sections were incubated for 30 min in blocking buffer (5% bovine serum albumin, BSA, 005% Tween-20 in PBS). Thereafter, sections were incubated for 1 h with monoclonal BAM-10 antibody, which cross-reacts with residues 1-12 of the Abeta peptide (Sigma Aldrich, St. Louis, MO, USA), diluted 1:200 in blocking buffer. Unbound antibody was removed by three washing steps for 5 min each with washing buffer (0.05% Tween-20 in PBS). After incubation with a secondary antibody-peroxidase conjugate (goat anti-mouse) diluted 1:500 in blocking buffer and washing steps, bound antibody was visualized by an enzyme substrate reaction with DAB (3,3'-diaminobenzidine tetrahydrochloride) as substrate applied by the DAB Enhanced liquid substrate system (Sigma Aldrich, St. Louis, MO, USA). By oxidation of DAB with the secondary antibody-coupled peroxidase, Abeta plaques were visualized by a brown precipitate. The substrate reaction was stopped by incubation with tap water. Histological sections were mounted in Polymount Xylene (Polysciences Inc., Warrington, PA, USA), and imaged with a DMI6000 microscope and a DFC420 camera (Leica Microsystems GmbH, Wetzlar, Germany). Plaque burden was analyzed by computerized quantitative image analysis, which quantifies brain areas (hippocampus and brain cortex) covered with Abeta AD plaques.

Similarly, hyperphosphorylated Tau was detected with AT8 antibody on paraffin-embedded brain sections from 12 months-old Tg-TauP301L mice (Model 2508, Taconic Biosciences, Rensselaer, NY, USA) without and with treatment with Compound-1 and Compound-4 for 6 months.

Immunoblot Detection of Proteins and Biochemical Analyses

For immunoblot detection of PHF-Tau in the hippocampus of aged 16 month-old rats subjected to the CUMS protocol for 4 weeks, hippocampi were dissected out from isolated brains on ice, pulverized under liquid nitrogen, and proteins were extracted with guanidine-hydrochloride (6.25 M guanidine hydrochloride in 50 mM Tris, pH 8.0 supplemented with 1× protease inhibitors and 1× phosphatase inhibitors) for 30 min at 4° C. Particulate material was removed by centrifugation at 50 000×g for 20 min at 4° C. Solubilized proteins were concentrated and delipidated by precipitation with ice-cold acetone/methanol (12:2, final concentration 83%) for 90 min at 4° C. The pellet was dissolved in SDS-sample buffer supplemented with 2% SDS, 0.1 M DTT (or 5% beta-mercaptoethanol), and 6 M urea for 90 min at room temperature. Proteins were stored at a concentration of 0.5-1 mg/ml at −70° C. for further use. After separation of proteins by 8 M urea-containing SDS-PAGE (7.5% polyacrylamide gel) and electrophoretic protein transfer to PVDF membranes in a tank transfer cell (Mini Trans-Blot cell, Bio-Rad GmbH, München, Germany) or by a semi-dry transfer apparatus (Trans-Blot® SD semi-dry transfer cell, Bio-Rad GmbH, München, Germany), immunoblot detection of hyperphosphorylated PHF-tau was performed with monoclonal anti-PHF antibody (AT8, MN1020; Thermo Fisher Scientific, Waltham, MA, USA). Bound antibody was visualized with $F(ab)_2$ fragments of enzyme-(peroxidase-)-coupled secondary antibodies (Dianova GmbH, Hamburg, Germany) pre-absorbed to mouse serum proteins, and followed by enhanced chemiluminescent detection (ECL Plus or ECL Prime, Amersham, GE Healthcare Life Sciences, Glattbrugg, Switzerland). For quantitative analysis, quantitative immunoblot evaluation was performed. To control for equal protein loading, the total content of hippocampal Gnb was determined.

For quantitative analysis of SDS-insoluble hippocampal contents of Abeta1-40 and Abeta1-42, hippocampi were dissected out from brains isolated on ice from 18-month-old Tg2576 mice without and with treatment for 6 months with Compound-1 and Compound-4. Isolated hippocampi were pulverized under liquid nitrogen, and SDS-insoluble Abeta peptides were extracted by serial extraction in 14 microL/mg wet weight of Tris buffer (50 mM Tris, 200 nM NaCl, 2 mM EDTA, pH 7.2, supplemented with 1× protease inhibitors/1× phosphatase inhibitors), followed by extraction with Triton X-100-containing buffer (Tris extraction buffer with 0.1% Triton X-100), and followed by extraction with 2% SDS. The remaining pellet was extracted with formic acid (70% formic acid in Tris buffer supplemented with 1× protease inhibitors/1× phosphatase inhibitors). The resulting formic-acid extract was neutralized with 1 M Tris buffer, pH 11, and used for quantitative determination of Abeta1-40 and Abeta1-42 by sandwich ELISA relative to a standard curve according to the protocol of the manufacturer (KHB3481 and KHB3441, Thermo Fisher Scientific, Waltham, MA, USA).

Neuronal cell loss and hyperphosphorylated PHF Tau were determined in hippocampi of 15 months-old Tg2576 mice, which were treated without or with Compound-1 and Compound-4 for three months during the neurodegeneration-enhancing CUMS (chronic unpredictable mild stress) protocol. Neuronal cell loss was determined with crude homogenates of dissected hippocampi by direct binding assay with the neuron-specific [125]-labeled anti-NeuN antibody (MAB377, clone A60, EMD Millipore, Merck KGaA, Darmstadt, Germany). Similarly, the neuronal cell loss-causing PHF tau hyperphosphorylation was quantified with [125]-labeled AT8 antibody. To determine neuronal cell bodies in the hippocampi of Tg2576 AD mice subjected to CUMS, hippocampi were dissected out from brains on ice, crude hippocampal homogenates were prepared (0.5 mg protein/ml PBS supplemented with 5% BSA and 1× protease inhibitors and 1× phosphatase inhibitors), and incubated with [125I]-labelled anti-NeuN antibody (final concentration 5×10-8 M; 1 microCi/point) in the absence and presence of a 10-fold molar excess of unlabeled antibody (to determine non-specific binding) for 1 h at 4° C. followed by three washing steps to remove unbound antibody. Similarly, the content of hyperphosphorylated PHF-tau was determined with [125I]-labelled AT8 antibody (AbdAlla et al., J. Biol. Chem. 284, 6554-6565 (2009)). The binding assays were performed in triplicates, and specific hippocampal-bound radioactivity indicative of the content of neuronal cell bodies and hyperphosphorylated PHF tau, respectively, was determined in a gamma-counter.

Example 1a: General Method for the Identification of GRK2-Inhibitory Compounds, which Inhibit Abeta Plaque Formation in the Tg2576 Model of Alzheimer's Disease In the context of the present invention, the following method is disclosed for the identification of compounds, which inhibit Abeta plaque formation in vivo, in an AD disease model, preferably the Tg2576 AD mouse, comprising the steps of (i) treating Tg2576 AD mice without and with the compound of interest in drinking water,
(ii) determination of Abeta plaque load in hippocampal and brain cortical areas by immunohistology with an Abeta-specific antibody,
(iii) identifying the compound of interest as an inhibitor, which inhibits the accumulation of senile AD plaques of insoluble Abeta compared to the untreated control.

It is preferred that the method for the identification of inhibitors as described above is a method wherein (a) in step (i), the treatment is performed for 3-6 months, preferably 6 months starting at an age between 3-12 months, preferably 12 months with an orally bioavailable compound in drinking water at a dose of 1-1000 mg/kg/d, preferably 5-10 mg/kg/d; and/or
(b) the treatment in step (i) is performed with a compound, which inhibits the GRK2-mediated phosphorylation of SRSF1; and/or
(c) in step (ii) Abeta plaque load is quantified by immunohistology on paraffin sections (or cryosections) with an antibody against Abeta; and/or
(d) the identification of an inhibitor of Abeta plaque formation in step (iii) is performed by quantitative image analysis relative to the untreated control.

Example 1b: Compounds for Use in the Present Invention Retard Abeta Plaque Formation in Tg2576 AD Mice Based on their previously demonstrated utility to prevent cardiovascular disease-induced ageing, the inventors investigated the compounds of their previous and presently unpublished patent application (PCT/EP2018/050504) and determined, whether these compounds could prevent neuropathological symptoms of Alzheimer's disease (AD), which is a typical ageing-associated disease. Compound-1 and Compound-4 (see FIG. 1A for structure, also disclosed in PCT/EP2018/050504) were tested.

For Abeta plaque load quantification by immunohistology, paraffin-embedded brain sections (or cryosections) (8 microm, 10-15 sections/brain taken at 30-50 microm intervals) were prepared from brains isolated from 18-month-old Tg2576 mice (Taconic Biosciences, Rensselaer, NY, USA) treated for six months without and with Compound-1 and Compound-4 (8 mg/kg/d in drinking water). After antigen retrieval by microwave heating for 30 min in antigen retrieval buffer (10 mM sodium citrate, pH 6.0, supplemented with 0.05% Tween-20), sections were washed with PBS, and endogenous peroxidases were inactivated by incubation for 5 min in 3% $H2O2$ solution. After washing with PBS, brain sections were incubated for 30 min in blocking buffer (5% bovine serum albumin, BSA, 005% Tween-20 in PBS). Thereafter, sections were incubated for 1 h with monoclonal BAM-10 antibody, which cross-reacts with residues 1-12 of the Abeta peptide (Sigma Aldrich, St. Louis, MO, USA), diluted 1:200 in blocking buffer. Unbound antibody was removed by three washing steps for 5 min each with washing buffer (0.05% Tween-20 in PBS). After incubation with a secondary antibody-peroxidase conjugate (goat anti-mouse) diluted 1:500 in blocking buffer and washing steps, bound antibody was visualized by an enzyme substrate reaction with DAB (3,3'-diaminobenzidine tetrahydrochloride) as substrate applied by the DAB Enhanced liquid substrate system (Sigma Aldrich, St. Louis, MO, USA). By oxidation of DAB with the secondary antibody-coupled peroxidase, Abeta plaques were visualized by a brown precipitate. The substrate reaction was stopped by incubation with tap water. Histological sections were mounted in Polymount Xylene (Polysciences Inc., Warrington, PA, USA), and imaged with a DMI6000 microscope and a DFC420 camera (Leica Microsystems GmbH, Wetzlar, Germany). Plaque burden was analysed by computerized quantitative image analysis, which quantifies brain areas (hippocampus and brain cortex) covered with Abeta AD plaques.

The immunohistological evaluation of Abeta plaque load showed that treatment with Compound-1 and Compound-4 for 6 months significantly retarded the accumulation of Abeta plaques in the hippocampus and frontal cortex of Tg2576 mice compared to untreated Tg2576 controls (FIGS. 1B, C).

Example 2a: Identification of GRK2-Inhibitory Compounds, which Inhibit the Hippocampal Neuronal Cell Loss in Tg2576 AD Mice Subjected to the Neurodegeneration-Enhancing CUMS Protocol In the context of the present invention the following method is disclosed for the identification of compounds, which inhibit the hippocampal neuronal cell loss in vivo, in an AD model, preferably the Tg2576 AD mouse model, preferably subjected to the neurodegeneration-enhancing CUMS protocol, comprising the steps of (i) subjecting aged 12-month-old Tg2576 AD mice to the neurodegeneration-enhancing CUMS (chronic unpredictable mild stress) protocol,
(ii) treating Tg2576 AD mice during the CUMS protocol without and with the compound of interest in drinking water,
(iii) determining the content of neuronal cell bodies in the hippocampus by direct binding assay with an anti-NeuN antibody, and
(iv) identifying the compound of interest as an inhibitor, which prevents hippocampal neuronal loss compared to the untreated control.

It is preferred that the method for the identification of inhibitors as described above is a method wherein (a) in step (i), aged Tg2576 AD mice, preferably 12 month of age, are subjected to the CUMS protocol for 1-3 months, preferably 3 months; and/or
(b) in step ((ii), the treatment of Tg2576 mice is performed during the CUMS protocol for 1-3 months, preferably for 3 months starting at an age of 12 months with an orally bioavailable compound in drinking water at a dose of 1-1000 mg/kg/d, preferably 5-10 mg/kg/d; and/or
(c) the treatment in step (ii) is performed with a compound, which inhibits the GRK2-mediated phosphorylation of SRSF1; and/or
(d) in step (iii) the hippocampal neuronal cell bodies and the neuronal cell loss-causing PHF tau hyperphosphorylation are quantified by direct binding assay with [125I]-labeled anti-NeuN antibody and [125I]-labeled anti-PHF antibody.

Example 2b: Compounds for Use in the Present Invention Retard Hippocampal Neuronal Loss and Tau Hyperphosphorylation in Tg2576 AD Mice Subjected to CUMS The sole inhibition of Abeta plaque formation and/or accumulation of insoluble Abeta peptides is probably not sufficient to retard neurodegeneration in AD patients (Kulshreshtha and Piplani, Neurol. Sci. 37, 1403-1435, 2016). In order to enhance the process of neurodegeneration in Tg2576 mice, the mice were subjected to environmental stress, which is known to aggravate symptoms of dementia and neurodegeneration in animal models and patients (AbdAlla et al., 2,3 AbdAlla et al., J. Biol. Chem. 284, 6554-6565 (2009); AbdAlla et al., J. Biol. Chem. 284, 6566-6574, 2009; Peavy et al., Biol. Psychiatry 62, 472-478 (2007); Wilson et al., Neuroepidemiology 27, 143-163 2006). Environmental stress was imposed by the chronic unpredictable mild stress (CUMS) protocol (AbdAlla et al., Biomed. Res. Int. 2015:917156, 2015; El-faramawy et al., Pharmacol. Biochem. Behav. 91, 339-344 (2009)). In addition to Tau hyperphosphorylation, environmental stress enhances neurodegeneration and induces hippocampal neuronal loss in Tg2576 mice (AbdAlla et al., J. Biol. Chem. 284, 6554-6565 (2009); AbdAlla et al., J. Biol. Chem. 284, 6566-6574, 2009).

Detailed Method

Neuronal cell loss and hyperphosphorylated PHF Tau were determined in hippocampi of 15 months-old Tg2576 mice, which were treated without or with Compound-1 and Compound-4 for three months during the neurodegeneration-enhancing CUMS (chronic unpredictable mild stress) protocol. Neuronal cell loss was determined with crude homogenates of dissected hippocampi by direct binding assay with the neuron-specific [125I]-labeled anti-NeuN antibody (MAB377, clone A60, EMD Millipore, Merck KGaA, Darmstadt, Germany). Similarly, the neuronal cell loss-causing PHF tau hyperphosphorylation was quantified with [125I]-labeled AT8 antibody. To determine neuronal cell bodies in the hippocampi of Tg2576 AD mice subjected to CUMS, hippocampi were dissected out from brains on ice, crude hippocampal homogenates were prepared (0.5 mg protein/ml PBS supplemented with 5% BSA and 1× protease inhibitors and 1× phosphatase inhibitors), and incubated with [125I]-labelled anti-NeuN antibody (final concentration 5×10-8 M; 1 microCi/point) in the absence and presence of a 10-fold molar excess of unlabelled antibody (to determine non-specific binding) for 1 h at 4° C. followed by three washing steps to remove unbound antibody. Similarly, the content of hyperphosphorylated PHF-tau was determined with [125I]-labelled AT8 antibody (AbdAlla et al., J. Biol. Chem. 284, 6554-6565 (2009)). The binding assays were performed in triplicates, and specific hippocampal-bound radioactivity indicative of the content of neuronal cell bodies and hyperphosphorylated PHF tau, respectively, was determined in a gamma-counter.

Treatment with representative Compound-1 and Compound-4 for three months significantly retarded the loss of hippocampal neurons as determined by anti-NeuN antibody binding as an indicator of neuronal loss (FIG. 2A). Concomitantly, treatment with illustrative Compound-1 and Compound-4 led to a significantly decreased hippocampal content of hyperphosphorylated PHF Tau in stressed Tg2576 mice (FIG. 2B). Thus, Compound-1 and Compound-4 retard hippocampal neuronal loss and tau hyperphosphorylation in AD mice.

Example 3: Compounds for Use in the Present Invention Retard Hippocampal Tau Hyperphosphorylation in a Rat Model with Symptoms of Sporadic AD, Ageing and Depression The Tg2576 mouse is a well-established genetic model of familial AD, which reproduces the gene mutation-induced generation of aggregation-prone Abeta. But the predominant late-onset sporadic AD is caused by multiple brain-insulting factors including, e.g. age, vascular and metabolic diseases, and psychiatric illnesses, which account for stress-related psychiatric syndromes. In view of the recent failure of several Abeta-targeting clinical trials (Doody et al., N. Engl. J. Med. 370, 311-321 (2014); Salloway, N. Engl. J. Med. 370, 322-333 (2014)), there is an urgent need to identify and target other (non-genetic) factors of neurodegeneration. The chronic unpredictable mild stress (CUMS) model reproduces psychological, psychosocial and physical stress as psychiatric risk factors of neurodegeneration, ageing and depression. The CUMS protocol induces typical neuropathological features of AD such as Abeta generation and Tau hyperphosphorylation in concert with other AD markers (Briones et al., Br. J. Pharmacol. 165, 897-907 (2012)). Moreover, the sensitivity of this model increases with age, which is the best-established risk factor for AD (AbdAlla et al., Biomed. Res. Int. 2015:917156 (2015); Briones et al., Br. J. Pharmacol. 165, 897-907 (2012); El-faramawy et al., Pharmacol. Biochem. Behav. 91, 339-344 (2009)). Because the CUMS model reproduces major features of sporadic AD, the treatment effect of compounds for use in the present invention as illustrated by Compound-1 and Compound-4 was also investigated in this non-genetic model of neurodegeneration. The treatment effects were evaluated in aged 16 months-old rats subjected to the CUMS protocol for four weeks, which is sufficient to trigger symptoms of neurodegeneration (AbdAlla et al., Biomed. Res. Int. 2015:917156 (2015)). The hippocampal content of hyperphosphorylated PHF Tau as a marker of neurodegeneration was determined in immunoblot (FIG. 3A). Oral treatment of aged rats subjected to chronic mild stress for 4 weeks significantly retarded hippocampal Tau hyperphosphorylation as detected with PHF-specific AT8 antibody (FIG. 3A,B). Thus, illustrative Compound-1 and Compound-4 both retard PHF Tau hyperphosphorylation in a rat model of neurodegeneration, which reproduces major symptoms of sporadic AD. Concomitantly, the stress-induced decrease in sucrose consumption as a marker of depression and anhedonia, was prevented by treatment with illustrative Compound-1 and Compound-4. Notably, after four weeks of stress imposed by the CUMS protocol, untreated stressed 16-month-old rats showed signs of anhedonia and depression, which was documented by a decreased sucrose consumption in the sucrose preference test, i.e. the sucrose consumption was decreased by more than 50% in stressed rats compared to the non-stressed age-matched control group (FIG. 3C). In addition, the sucrose consumption of rats subjected to CUMS and treated with Compound-1 and Compound-4 during the CUMS protocol was not significantly different from the non-stressed control group (FIG. 3C). These findings demonstrate that illustrative Compound-1 and Compound-4 can prevent symptoms of anhedonia and depression in addition to neurodegenerative PHF tau hyperphosphorylation.

Example 4: Treatment with Compounds for Use in the Present Invention Retards PHF Tau Hyperphosphorylation in the Tg-TauP301L Model of Tauopathy Furthermore, the compounds for use in the present invention were investigated in a genetic model of tauopathy and Tau dysfunction, i.e. Tg-TauP301L mice with neuron-specific expression of the most common FTDP-17 (frontotemporal dementia and parkinsonism linked to chromosome 17) mutation (Lewis et al., Nature Genetics 25, 402-405 (2000)). Untreated 12 months-old Tg-TauP301L mice showed prominent PHF Tau hyperphosphorylation in axons of the hippocampal CA3 area (FIG. 4A). Tau hyperphosphorylation was largely absent in age-matched Tg-TauP301L mice treated for 6 months with illustrative Compound-1 and Compound-4 (FIG. 4A). Quantitative evaluation showed that treatment with illustrative Compound-1 and Compound-4 led in both cases to a significantly decreased hippocampal content of hyperphosphorylated PHF-Tau (FIG. 4B).

Example 5: Identification of GRK2-Inhibitory Compounds, which Inhibit PHF Tau Hyperphosphorylation in the Tg-TauP301L Model of Tauopathy In the context of the present invention, the following method is disclosed for the identification of compounds, which inhibit the neuronal formation of hyperphosphorylated PHF tau in vivo, in a disease model of tauopathy, preferably the Tg-TauP301L mouse model comprising the steps of (i) treating Tg-TauP301L mice without and with the compound of interest in drinking water,
(ii) determining the content of hyperphosphorylated PHF tau in brain and hippocampal areas by immunohistology with a PHF-specific antibody,
(iii) identifying the compound of interest as an inhibitor, which inhibits the formation of hyperphosphorylated PHF-Tau compared to the untreated control.

It is preferred that the method for the identification as described above is a method wherein (a) in step (i), the treatment is performed for 3-6 months, preferably 6 months starting at an age of 3-6 months, preferably 6 months with an orally bioavailable compound in drinking water at a dose of 1-1000 mg/kg/d, preferably 5-10 mg/kg/d; and/or
(b) the treatment in step (i) is performed with a compound, which inhibits the GRK2-mediated phosphorylation of SRSF1; and/or
(c) in step (ii), the content of hyperphosphorylated PHF tau is quantified by immunohistology on paraffin sections (or cryosections) with an antibody against hyperphosphorylated PHF tau; and/or
(d) the identification of an inhibitor of hyperphosphorylated PHF tau formation in step (iii) is performed by quantitative image analysis.

Detailed Method

For detection of hyper-phosphorylated PHF Tau by immunohistology, paraffin-embedded brain sections (or cryosections) (8 microm, 10-15 sections/brain taken at 30-50 microm intervals) were prepared from brains isolated from 12-month-old Tg-TauP301L taupathy model mice (Model 2508; Taconic Biosciences, Rensselaer, NY, USA) without and with 6 months of treatment with Compound-1 and Compound-4 (8 mg/kg body-weight/day in drinking water). After antigen retrieval by microwave heating for 30 min in antigen retrieval buffer (10 mM sodium citrate, pH 6.0, supplemented with 0.05% Tween-20), histological sections were washed with PBS, and endogenous peroxidases were inactivated by incubation for 5 min in 3% H2O2 solution. After washing with PBS, brain sections were incubated for 30 min in blocking buffer (5% bovine serum albumin, BSA, 0.05% Tween-20 in PBS). Thereafter, sections were incubated for 1 h with monoclonal AT8 antibody diluted 1:200 in blocking buffer, which detects the PHF-form of hyperphosphorylated tau (Sigma Aldrich, St. Louis, MO, USA). Unbound antibody was removed by three washing steps for 5 min each with washing buffer (0.05% Tween-20 in PBS). After incubation with a secondary antibody-peroxidase conjugate (goat anti-mouse) diluted 1:500 in blocking buffer and washing steps, bound antibody was visualized by an enzyme substrate reaction with the DAB (3,3'-diaminobenzidine tetrahydrochloride) as substrate applied by the DAB Enhanced liquid substrate system (Sigma Aldrich, St. Louis, MO, USA). By oxidation of DAB with the secondary antibody-coupled peroxidase, hyperphosphorylated PHF tau was visualized by a brown precipitate. The substrate reaction was stopped by incubation with tap water. Histological sections were mounted in Polymount-Xylene (Polysciences Inc., Warrington, PA, USA), and imaged with a DMI6000 microscope and a DFC420 camera (Leica Microsystems GmbH, Wetzlar, Germany). The content of hyperphosphorylated PHF tau was analysed by computerized quantitative image analysis, which quantifies areas stained positive for PHF-tau.

Example 6: Identification of GRK2-Inhibitory Compounds, which Inhibit PHF Tau Hyperphosphorylation in a Rat Model of Depression with Symptoms of Early Sporadic AD In the context of the present invention, the following method is disclosed for the identification of compounds, which inhibit the neuronal accumulation of hyperphosphorylated PHF tau in vivo, in a disease model of depression with symptoms of early sporadic AD, preferably the chronic unpredictable mild stress model (CUMS) comprising the steps of (i) treating aged rats subjected to the CUMS protocol without and with the compound of interest in drinking water,
(ii) determining the content of hyperphosphorylated PHF tau in the hippocampus by immunoblot detection with a PHF-specific antibody,
(iii) identifying the compound of interest as an inhibitor, which inhibits the formation and/or accumulation of hyperphosphorylated PHF-Tau compared to the untreated control.

It is preferred that the method for the identification of compounds as described above is a method wherein (a) in step (i), the treatment is performed for 1-3 months, preferably 1 month during the CUMS protocol starting at an age of 13-18 months, preferably 15 months with an orally bioavailable compound in drinking water or by oral gavage at a dose of 1-1000 mg/kg/d, preferably 5-10 mg/kg/d; and/or
(b) the treatment in step (i) is performed with a compound, which inhibits the GRK2-mediated phosphorylation of SRSF1; and/or (c) in step (ii), the content of hyperphosphorylated PHF tau is quantified by immunoblot detection in hippocampal lysates with an antibody against hyperphosphorylated PHF tau.

Detailed Method

For immunoblot detection of PHF-Tau in the hippocampus of aged 16 month-old rats subjected to the CUMS protocol for 4 weeks, hippocampi were dissected out from isolated brains on ice, pulverized under liquid nitrogen, and proteins were extracted with guanidine-hydrochloride (6.25 M guanidine hydrochloride in 50 mM Tris, pH 8.0 supplemented with 1× protease inhibitors and 1× phosphatase inhibitors) for 30 min at 4° C. Particulate material was removed by centrifugation at 50 000×g for 20 min at 4° C. Solubilized proteins were concentrated and delipidated by precipitation with ice-cold acetone/methanol (12:2, final concentration 83%) for 90 min at 4° C. The pellet was dissolved in SDS-sample buffer supplemented with 2% SDS, 0.1 M DTT (or 5% beta-mercaptoethanol), and 6 M urea for 90 min at room temperature. Proteins were stored at a concentration of 0.5-1 mg/ml at −70° C. for further use. After separation of proteins by 8 M urea-containing SDS-PAGE (7.5% polyacrylamide gel) and electrophoretic protein transfer to PVDF membranes in a tank transfer cell (Mini Trans-Blot cell, Bio-Rad GmbH, München, Germany) or a semi-dry transfer apparatus (Trans-Blot® SD semi-dry transfer cell, Bio-Rad GmbH, München, Germany), immunoblot detection of hyperphosphorylated PHF-tau was performed with monoclonal anti-PHF antibody (AT8, MN1020; Thermo Fisher Scientific, Waltham, MA, USA). Bound antibody was visualized with $F(ab)_2$ fragments of enzyme-(peroxidase-)-coupled secondary antibodies (Dianova GmbH, Hamburg, Germany) pre-absorbed to mouse/rat serum proteins, and followed by enhanced chemiluminescent detection (ECL Plus or ECL Prime, Amersham, GE Healthcare Life Sciences, Glattbrugg, Switzerland). For quantitative analysis, quantitative immunoblot evaluation was performed. To control for equal protein loading, the total content of hippocampal Gnb was determined, which is the Gbeta subunit of heterotrimeric G-proteins.

Example 7: Identification of GRK2-Inhibitory Compounds, which Inhibit Symptoms of Anhedonia and Depression in a Rat Model of Depression In the context of the present invention, the following method is disclosed for the identification of compounds which inhibit symptoms of anhedonia and depression in vivo, in a disease model of depression, preferably the chronic unpredictable mild stress (CUMS) model comprising the steps of (i) treating rats or mice subjected to the CUMS protocol without and with the compound of interest in drinking water or by oral gavage, (ii) determining anhedonia as a symptom of depression by the sucrose preference test, (iii) identifying the compound of interest as an inhibitor, which prevents the development of symptoms of depression.

It is preferred that the method for the identification of compounds as described above is a method wherein (a) in step (i), the treatment is performed for 1-3 months, preferably 1 month during the CUMS protocol starting at an age of 3-12 months, preferably 4 months (young) or at an age of 13-18 months, preferably 15 months (old) with an orally bioavailable compound in drinking water or by oral gavage at a dose of 1-1000 mg/kg/d, preferably 5-10 mg/kg/d; and/or (b) the treatment in step (i) is performed with a compound, which inhibits the GRK2-mediated phosphorylation of SRSF1 and/or decreases the hippocampal content of hyperphosphorylated PHF tau; and/or (c) in step (ii), anhedonia as a major symptom of depression is assessed by the sucrose preference test.

Detailed Method

Symptoms of depression and anhedonia induced by the CUMS protocol as a typical model of depression were determined by the sucrose preference test. For the sucrose preference test, rats (or mice) were trained to consume a sucrose solution (2%), which was put in the cage with a bottle of water. The sucrose consumption was determined at baseline for two weeks before the CUMS protocol (1 test per week, for 1 h, at 9-10 a.m.), and after 4 weeks of CUMS immediately after a period of food (24 h) and water (12 h) deprivation. The ratio of the sucrose-to-water consumption was determined. A CUMS-induced decrease in the sucrose-to-water consumption ratio by more than 50% compared to baseline and/or compared to the age-matched untreated control group without CUMS was considered as an indicator of anhedonia and depression. Similarly, the treatment effect of illustrative compounds on prevention of symptoms of depression was assessed by the sucrose preference test. Rats were treated for 4 weeks with illustrative Compound-1 and Compound-4 during the CUMS protocol (8 mg/kg/d in drinking water or by oral gavage). Untreated, age-matched rats subjected to the CUMS protocol served as the anhedonia-positive group, and untreated rats not subjected to the CUMS protocol served as a control group without anhedonia. Aged rats (>15 months) are highly sensitive to the CUMS protocol and usually more than 90% of aged rats exposed to the CUMS protocol developed anhedonia. The sucrose preference test also was performed with young rats (aged 4 months). However, the number of young rats, which develop CUMS-induced anhedonia is lower (about 80%). In agreement with the treatment effect observed in old rats, the sucrose preference test showed that treatment of young rats with Compound-1 and Compound-4 also prevented the development of CUMS-induced anhedonia and symptoms of depression. In addition, the sucrose preference test can also be applied to assess CUMS-induced symptoms of depression and anhedonia and treatment effects of GRK2-inhibitory compounds in other species, e.g. (but not restricted to) mice, which can be wild-type or genetically modified.

Example 8: Identification of GRK2-Inhibitory Compounds, which Inhibit the Hippocampal Accumulation of SDS-Insoluble Abeta Peptides, Abeta1-40 and Abeta1-42

In the context of the present invention, the following method is disclosed for the identification of compounds, which inhibit the hippocampal accumulation of SDS-insoluble Abeta peptides, Abeta1-40 and Abeta1-42, in vivo, in an AD disease model, preferably the Tg2576 AD mouse comprising the steps of (i) treating Tg2576 AD mice without and with the compound of interest in drinking water (ii) determination of the content of SDS-insoluble Abeta peptides in hippocampal and/or brain cortical areas by sandwich ELISA (iii) identifying the compound of interest as an inhibitor, which inhibits the hippocampal accumulation of insoluble Abeta peptides compared to the untreated control.

It is preferred that the method for the identification of inhibitors as described above is a method wherein (a) in step (i), the treatment is performed for 3-12 months, preferably 6 months starting at an age of 3-12 months, preferably 12 months with an orally bioavailable compound in drinking water at a dose of 1-1000 mg/kg/d, preferably 5-10 mg/kg/d; and/or (b) the treatment in step (i) is performed with a compound, which inhibits the GRK2-mediated phosphorylation of SRSF1; and/or (c) in step (ii) the hippocampal and/or brain content of SDS-insoluble Abeta1-40 and Abeta1-42 is quantified with a sandwich ELISA specific for Abeta1-40 and Abeta1-42.

Detailed Method

For quantitative analysis of SDS-insoluble hippocampal contents of Abeta1-40 and Abeta1-42, hippocampi were dissected out from brains isolated on ice from 18-month-old Tg2576 mice without and with treatment for 6 months with Compound-1 and Compound-4. Isolated hippocampi were pulverized under liquid nitrogen, and SDS-insoluble Abeta peptides were extracted by serial extraction in 14 microL/mg wet weight of Tris buffer (50 mM Tris, 200 mM NaCl, 2 mM EDTA, pH 7.2, supplemented with 1× protease inhibitors/1× phosphatase inhibitors), followed by extraction with Triton X-100-containing buffer (Tris extraction buffer with 0.1% Triton X-100), and followed by extraction with 2% SDS. The remaining pellet was extracted with formic acid (70% formic acid in Tris buffer supplemented with 1× protease inhibitors/1× phosphatase inhibitors). The resulting formic-acid extract was neutralized with 1 M Tris buffer, pH 11, and used for quantitative determination of Abeta1-40 and Abeta1-42 by sandwich ELISA and with a standard curve according to the protocol of the manufacturer (KHB3481 and KHB3441, Thermo Fisher Scientific, Waltham, MA, USA).

Example 9: Method for Identification of Compounds, which Inhibit the GRK2-Mediated Phosphorylation Assay of SRSF1

In the context of the present invention the following method is disclosed for the identification of inhibitors of the G-protein-coupled receptor kinase 2 (GRK2), preferably by determination of the GRK2-mediated phosphorylation of the serine/arginine-rich splicing factor 1 (SRSF1) comprising the steps of (i) providing and incubating GRK2 and SRSF1 under physiological conditions suitable for the phosphorylation of SRSF1 in the presence and in the absence of a compound of interest;

(ii) determining the phosphorylation of SRSF1 in the presence and in the absence of the compound of interest;

(iii) identifying the compound of interest as an inhibitor or non-inhibitor based on the phosphorylation of SRSF1 in the presence of the compound of interest relative to the phosphorylation of SRSF1 in the absence of the compound of interest.

It is preferred that the method for the identification as described above is a method wherein (a) in step (i), the incubation is performed in the presence of radioactively labelled ATP, preferably [gamma-$^{32}$P] ATP, preferably at about 25 to 37° C. for about 30 to 90 min; and/or (b) the incubation of step (i) is stopped by dilution at temperatures below 30° C., preferably at temperatures of about 0 to 10° C.; and/or (c) the determination of the phosphorylation of SRSF1 in step (ii) is performed by (A) filtering the product of (i) through a filter, preferably a glass fiber filter; (B) washing the filter; and (C) determining the filter-bound radioactivity, preferably with a beta-counter.

Detailed Method

For the identification of small molecule inhibitors of the (GRK2)-mediated phosphorylation of (SRSF1), the phosphorylation assay was performed in a reaction buffer (e.g. 20 mM Tris, 2 mM EDTA, 5 mM MgCl2, 0.05% BSA, pH 7.5,) supplemented with ATP, preferably about 50 microM, [gamma-32P]-ATP (e.g. 1×10 6 DPM, specific activity of about 3000 Ci/mmol)) and about 300-500 nM of SRSF1. The reaction mixture was added to GRK2 (e.g. about 100 nM-1 microM, preferably 100 nM) in reaction buffer, without or with increasing concentrations of the small molecule compound) to give a final reaction volume of, e.g. about 50 microL. After an incubation for e.g. about 30-60 min at about 30° C., the phosphorylation was stopped by the addition of ice-cold reaction buffer, preferably about 5 volumes. The reaction mixture was immediately applied to filters, preferably glass fiber filters. After three washing steps, e.g. with about 5 ml of reaction buffer, filter-bound radioactivity was determined in a beta-counter.

Conclusions on the Experimental Data of Examples 1 to 9

The above data show that compounds for use in the present invention, which also retard cardiovascular disease-induced ageing (presently unpublished PCT/EP2018/050504), retard the formation of Abeta plaques, Tau hyperphosphorylation and hippocampal neuronal loss as major hallmarks of AD and neurodegeneration in different animal models of neurodegenerative diseases and tauopathies, i.e. the Tg2576 genetic model of AD, the non-genetic CUMS model of neurodegeneration with features of sporadic AD, ageing and depression, and the Tg-TauP301L genetic model of tauopathy. In addition, compounds for use in the present invention also prevent anhedonia as a major symptom of depression and psychiatric disorders with neurodegeneration. Without wishing to be bound by theory, it is assumed that neuroprotective mechanisms induced by these compounds could involve inhibition of mitochondrial dysfunction caused by GRK2 (Sato et al., J. Mol. Cell. Cardiol 89, 360-364 (2015)), and retardation of SRSF1-induced symptoms of ageing (Harhouri K et al., EMBO Mol. Med. 9, 1294-1313 (2017)).

Example 10: Generation of Tg-MPP1 Mice with Ubiquitous Expression of the Human Senescence Protein, MPP1

Expression of MPP1 in vivo, in transgenic mice was achieved by expression of MPP1 under control of the CMV promoter (cytomegalovirus immediate-early promoter/enhancer). Transgenic Tg-MPP1 mice were generated by injection of purified, linearized DNA (2 ng/microl) encoding MPP1, into the pro-nucleus of fertilized oocytes of super-ovulated FVB mice, followed by oviduct transfer into pseudo-pregnant foster mice. Offspring were weaned at an age of 3-4 weeks, and ear-punch biopsies were taken at an age of 4 weeks for PCR genotyping to identify founder mice with stable insertion of the transgene into genomic mouse DNA. The following oligonucleotide primer pair was used for genotyping PCR: MPP1-forward 5'-CGC CTT TCA TTG TGT TCA TTG CAC CTA CTG-3' (SEQ ID NO: 1); Sp6-reverse 5'-TAG AAG GCA CAG TCG AGG-3' (SEQ ID NO: 2).

Example 11: Determination of Aging-Induced Deterioration of Male Sperm Quality and Female Fertility Sperm count, and motility were determined by microscopic semen analysis of male B6 mice at an age of 3 months and 18 months similarly as described (Komori et al., Reprod. Med. Biol. 5, 195-200, 2006). Sperm cells were isolated from male B6 mice from the epididymis as described (Esposito et al., Proc. Nat. Acad. Sci. U.S.A. 101, 2993-2998, 2004). Sperm concentration was determined with a Neubauer hemocytometer. Percentage of sperm motility was determined with a 10 microl sample loaded onto a clean slide glass and covered with a coverslip. Sperm motility was evaluated under positive phase-contrast microscopy at a total magnification of ×400, and graded according to the WHO criteria (Komori et al., Reprod. Med. Biol. 5, 195-200, 2006), i.e. percentage of motile sperm cells was counted, and the percentage of progressive and not progressive sperm motility was determined. At least 300 spermatozoa were evaluated. Spermatozoa viability was determined by eosin-nigrosine staining technique. A drop of spermatozoa suspension in PBS was mixed with one drop of aqueous eosin Y solution (1%), and incubated for 15 s. Thereafter, two drops of 10% aqueous nigrosine solution were added and mixed. An aliquot of this mixture was transferred to a glass slide, a thin smear was made, and air dried. Stained spermatozoa were examined under a light microscope, and the percentage of live sperm cells was determined. Live sperm cells appear white whereas dead sperm cells are coloured pink. Treatment of male B6 mice with Compound-1 and Compound-1F (8 mg/kg/d in drinking water) was started at an age of 3 months and continued until the end of the observation period at an age of 18 months.

Example 12: Measurement of Serum Level of Compound-1, Compound-1F and Compound-4 in Mice, Dogs and Humans Dog serum concentrations of Compound-1, Compound-1F and Compound-4 were determined with serum isolated from the blood of German shepherd dogs (age: 8-9 months) taken at different time points (2 h, 4 h, 6 h, 8, 10 h, 24 h) after oral drug intake. The steady-state serum concentrations of Compound-1, Compound-1F and Compound-4 were determined in mice with blood isolated at the end of the study by cardiac puncture. Serum proteins were removed by acetonitrile precipitation, and compounds were extracted by chloroform before separation on an HPLC-C18 column (Poroshell 120 EC-C18, Agilent) with an HPLC system (Agilent 1100 Series) and detection at OD 280 nm, for Compound-1 and Compound-1F. Detection of Compound-4 was performed at OD 310 nm. The same extraction method was also used to determine Compound-1F in the serum of healthy human research participants. Dog hematology and biochemical parameters were determined by the Center of Applied Analytical and Veterinary Studies, Cairo, Egypt. ECG and blood pressure were measured by Dr. Mohamed Elsaed, Electrocardiography Unit, Faculty of Veterinary Medicine, Cairo University. The study was approved by the ethical committee of the Center of Applied and Veterinary Studies, Cairo, Egypt. Clinical laboratory parameters of human research participants were determined by the Rabaa El Adaweya Medical Central Hospital, Cairo, Egypt.

Example 13: Clinical Study in Healthy Human Voluntary Research Participants

The study analysed the serum concentration and human clinical laboratory parameters of healthy voluntary human research participants before and after the oral intake of Compound-1F. The study was performed according to the study protocol.

Study design: The study was a three-part phase-1, randomized, placebo-controlled study of Compound-1F. The primary end-point was safety and tolerability. Secondary objectives were plasma pharmacokinetics data (part-1, part-2, part-3) and peripheral blood mononuclear cell MPP1 status (part-3).

The first part (part-1) was a single ascending dose-effect study with three cohorts of 4 healthy research participants each, who received a single dose of 20 mg, 40 mg or 60 mg in subsequent cohorts. Three drug-treated and one placebo-treated subjects were randomized in each cohort (2 males, 2 females; age: 35-65 years). After completion of safety assessment, blood was drawn for analysis of pharmacokinetics data.

In the second part (part-2) of the study, the daily dose was increased every two days until the final dose of 60 mg/day was reached, i.e. the daily dose was 20 mg on day-1 and day-2, 40 mg on day-3 and day-4, and 60 mg on day-5 until day-14. Blood was drawn before study begin for analysis of laboratory parameters and on day-14 for analysis of laboratory parameters and determination of pharmacokinetics data, at the indicated time points after administration of the last dose of 60 mg. All study participants (n=10; 7 males, 3 females; Caucasians; age: 37-66 years; 8 participants received drug, and two received placebo) were healthy and had the possibility to withdraw from the study at any time. All study participants wanted to complete the study.

In the third part (part-3) of the study, a cohort of 8 healthy elderly voluntary research participants (7 males, 1 female; age 60-73 years; all Caucasians) received a daily oral dose of 60 mg of Compound-1F for 28 days (6 participants received drug, 2 placebo). In part-3 of the study, blood was drawn before study begin for analysis of clinical laboratory parameters and MPP1 status, and on day-28 for analysis of laboratory parameters and MPP1 status, and 24 h after the last drug intake for measurement of serum concentration of Compound-1F. All participants of part-3 had the possibility to withdraw from the study at any time but all study participants wanted to complete the study.

The study participants were under the medical supervision of the Rabaa El Adaweya Medical Central Hospital, Cairo, Egypt (Clinical study director: Dr. Raafat Mahmood Fawzy). Clinical laboratory parameters, and cardiovascular examination data (blood pressure, heart rate) of all research participants (drug treatment group and placebo group) were within the normal range during the study and after completion of the study (observation period 4 weeks). One participant in the placebo group and 1 participant in the drug treatment group (part-2 of the study) reported softer stools beginning on day-3 after drug/placebo intake. This side effect ended after completion of the study, and was most likely due to the intake of mannitol, which was used as an additive for formulation of study drug and placebo. There were no other adverse effects in part-1, part-2 and part-3 of the study.

Study participants in the treatment group of part-2 of the study reported the following beneficial effects: (i) better sexual performance and climax (n=3 males), (ii) better physical performance (n=3), (iii) better memory (n=3), and better physical well-being (n=5). The two participants in the placebo group did not report any beneficial effect. Elderly healthy research participants of part-3 of the study reported better memory (n=4), better physical performance and well-being (n=5), and better sexual performance and climax (n=3 males). The two participants in the placebo group of part-3 of the study did not report any beneficial effect. The study protocol was conducted in accordance with the Declaration of Helsinki. All research participants provided written informed consent before participation. Research participants had the possibility to withdraw at any time from the study. But all participants wanted to complete the study.

Example 14: Identification of the Human Senescence Marker, MPP1, by Whole Genome Microarray Gene Expression Profiling of Human Peripheral Blood Mononuclear Cells Whole genome microarray gene expression profiling was performed with peripheral blood mononuclear cells. Peripheral blood mononuclear cells were isolated from blood plasma (anticoagulated by heparin) by density gradient centrifugation over Ficoll® Paque Plus (GE Healthcare. In a typical isolation, blood plasma (3 ml) was diluted 1:1 with sterile PBS and supplemented with 3 ml of Ficoll® Paque Plus. The medium was centrifuged for 30 min at 300×g, and the upper ring layer with enriched mononuclear cells was collected, diluted 1:3 with PBS and cells were isolated by centrifugation. Total RNA was isolated from peripheral blood mononuclear (PBMN) cells by the RNeasy Mini kit according to the protocol of the manufacturer (Qiagen). RNA purity was between 1.8 and 2 as determined by the absorbance ratio of 260 nm/280 nm. RNA quality and absence of signs of degradation were controlled by RNA electrophoresis on a denaturing agarose gel by the presence of bright bands of 28S and 18S ribosomal RNA. Total RNA was processed for whole genome microarray gene expression profiling with the GeneChip One-Cycle Target Labeling System (Affymetrix) according to the protocol of the manufacturer (Affymetrix GeneChip Expression Analysis Technical Manual Rev. 5). Hybridization with the GeneChip (Affymetrix GeneChip Human genome U133 Plus 2.0 Array) was done with 15 microg of fragmented cRNA in 200 microl of hybridization solution in a Hybridization Oven 640 (Affymetrix) at 45° C. for 16 h. Washing and staining of gene chips was done with the Affymetrix Fluidics Station 450 followed by scanning (Affymetrix GeneChip Scanner 7G). Signal processing was performed with GCOS (v. 1.4. Affymetrix). Data were scaled to a target value of 200. Probe sets (with call present and/or signal intensity ≥100) with significantly different signal intensity ($p<0.05$) indicative of different gene expression between the two different age groups were identified by TIGR MultiExperiment Viewer (MeV v4.9).

Conclusions on the Experimental Data of Examples 10 to 14

Development of fluorinated Compound-1F as an analogue of Compound-1 with modified physicochemical and pharmacokinetic properties. Compound-1F is the fluorinated analogue of Compound-1 (FIG. 5A) and was developed because the introduction of a fluorine into a small molecule can modulate various pharmacokinetic and physicochemical properties such as metabolic stability and enhanced membrane permeation (Shah and Westwell, J. Enzyme Inhibition Med. Chem. 22, 527-540, 2007; Böhm et al., Chembiochem 5, 637-643. 2004). Another potential application of the fluorine atom is the potential use of 18F as a radiolabel tracer atom in positron-emission tomography (PET) imaging (Shah and Westwell, J. Enzyme Inhibition Med. Chem. 22, 527-540, 2007). The pharmacokinetic measurements presented herein in dogs showed that fluorinated Compound-1F has a different pharmacokinetic profile compared to Compound-1, with a slower on-rate. This slower on-rate circumvents the high peak plasma levels, which is achieved by oral gavage of Compound-1 (cf. FIG. 13A-C). In this respect, Compound-1F mimics a modified release formulation with sustained release, which can be specifically useful, e.g., for treatment of a chronic disease state. In view of the modified pharmacokinetic properties of Compound-1 by fluorination without changing the therapeutic effect of this Compound (cf. FIG. 6, FIG. 7, FIG. 8, FIG. 10), the present invention encompasses the therapeutic use described above of all possible fluorinated analogues of Compound-1, with single and/or multiple fluorination of all possible free positions in this Compound-1 and Compound-1F (FIG. 5A).

Compound-1 and Compound-1F retard hippocampal insoluble amyloid-beta accumulation, neuronal loss and neuronal loss-causing PHF tau hyperphosphorylation in Tg2576 AD mice. The treatment effect of Compound-1F and Compound-1 was compared, and 12-month-old Tg2576 AD mice were treated for 6 months with Compound-1 and Compound-1F. It was found that Compound-1F retarded hippocampal accumulation of insoluble Abeta1-40 and Abeta1-42 indicative of a decreased Abeta plaque accumulation in aged Tg2576 AD mice (FIG. 6A,B). Retardation of hippocampal Abeta accumulation induced by Compound-1F was comparable to the treatment effect achieved by Compound-1 (FIG. 6A,B). In addition, Compound-1F also retarded the hippocampal neuronal loss induced by 3 months of CUMS (chronic unpredictable mild stress) in 15-month-old Tg2576 AD mice (FIG. 6C). Concomitantly, the neuronal cell loss-causing PHF tau hyperphosphorylation induced by 3 months of CUMS was also retarded by Compound-1F (FIG. 6D).

Compound-1 and Compound-1F retard the aging-induced decline in male fertility as a major symptom of aging. In view of the positive treatment effect of Compound-1, and Compound-1F on symptoms of AD-induced neurodegeneration, it was investigated whether Compound-1 and Compound-1F also retard other symptoms of aging because Alzheimer's disease is a typical "aging"-dependent disease. Notably, advanced age is the leading risk factor of sporadic Alzheimer's disease (Hara et al., Neurology 92, 84-93, 2019), which is the most frequent form of AD encompassing more than 99% of all AD cases. To address whether the compounds described herein retard symptoms of aging, well-established symptoms of aging were investigated. Reduced male and female fertility is one of the best-characterized symptoms of aging, not only in rodents and mice (Parkening T A, J. Rerprod. Fertil 87, 727-733, 1989) but also in humans (Pellicer A et al., Hum. Reprod. 10 Suppl. 2, 77-83; Matorras et al., Gynecol. Obstet. Invest. 71, 229-235, 2011). Therefore, it was investigated whether Compound-1 and Compound-1F also retard the decline in male and female fertility as a hallmark of aging. It was found that long-term treatment with Compound-1 and Compound-1F retarded the aging-induced decline in male and female fertility. Retardation of male aging is documented in FIG. 7, which shows that 15 months of treatment with Compound-1 and Compound-1F retarded the aging-induced decrease in sperm count and sperm vitality (FIG. 7A,B,E). Sperm vitality of Compound-1- and Compound-1F-treated 18-month-old B6 mice compared to untreated control mice was determined by eosin-nigrosine staining (FIG. 7B,E). Live sperm cells appear white whereas dead sperms of untreated B6 mice are coloured pink (FIG. 7E). In addition, treatment with Compound-1 and Compound-1F for 15 months significantly retarded the aging-induced decline in sperm motility (FIG. 7C,D). Notably, the decrease in progressive sperm motility was largely prevented by Compound-1 and Compound-1F (FIG. 7C,D). Concomitantly, the aging-induced epididymal degeneration of 18-month-old male B6 mice was also prevented by treatment for 15 months with Compound-1 and Compound-1F (FIG. 7F). Hematoxylin-eosin stained sections of the cauda epididymis show very few spermatozoa in tubule lumens of untreated aged mice compared to a high sperm abundance in treated mice (FIG. 7F). Without wishing to be bound by theory, the retardation of these major symptoms of aging could involve GRK2-inhibition-mediated prevention of mitochondrial dysfunction (Sato et al., J. Mol. Cell. Cardiol. 89, 360-364, 2015), which is a common cause of aging (Sun et al., Mol Cell 61, 654-666, 2016). In addition, GRK2 inhibition is known to enhance cAMP signalling (cf. patent application WO/2018/130537 (PCT/EP2018/050504)), which is an essential driver of sperm motility (Esposito et al., Proc. Nat. Acad. Sci. U.S.A. 101, 2993-2998, 2004).

Treatment with Compound-1 and Compound-1F retards the aging-induced decrease in fertility in female B6 mice. Compound-1 and Compound-1F also retarded symptoms of aging in female B6 mice, i.e. the aging-induced decrease in fertility (FIG. 8A,B). Taken together, Compound-1 and Compound-1F retard major symptoms of aging in mice: (i) the aging-dependent hippocampal accumulation of aggregated amyloid-beta, (ii) the stress-enhanced hippocampal neuronal loss, (iii) the neurodegeneration-enhancing tau hyperphosphorylation, and (iv) the aging-induced decline in male and female fertility.

MPP1 was identified as a human senescence marker in human peripheral blood mononuclear cells. MPP1 gene (Membrane Palmitoylated Protein 1) was found to have a highly significant increased gene expression in the older age group compared to the younger age group (FIG. 9F). A highly significant MPP1 up-regulation was found in peripheral blood cells (PBMN cells) of aged human research participants, and available data indicated that MPP1 expression is up-regulated in vitro, in cells by major aging-related processes. Hence, it was concluded that the data presented herein identified up-regulated MPP1 as a previously unrecognized senescence marker in human peripheral blood mononuclear cells.

Tg-MPP1 mice develop a phenotype of premature aging. Transgenic mice with ubiquitous expression of MPP1 under control of the CMV promoter were generated (FIG. 10A). Positive founder mice of the F0 generation were identified by genotyping PCR (FIG. 10B). As a control, immunoblot detection showed that mouse peripheral blood mononuclear cells from aged Tg-MPP1 mice had a significantly increased MPP1 protein content compared to age-matched non-transgenic FVB controls (FIG. 10C). This finding documents the transgenic MPP1 protein in mouse PBMN cells. The phenotype of Tg-MPP1 mice was characterized and it was found that increased systemic MPP1 expression induced a phenotype of premature senescence, which led to a significantly reduced lifespan of Tg-MPP1 mice (FIG. 10D). Thus, MPP1 is not only a marker of senescence in human PBMN cells but also an aging-inducing gene in vivo, in mice. The Mpp1 protein content in PBMN cells of aged 18-month-old B6 mice treated for 15 months with Compound-1 and Compound-1F in drinking water was determined (FIG. 10E). Immunoblot detection of Mpp1 in PBMN cells showed that treatment with Compound-1 and Compound-1F significantly decreased the content of the senescence marker, Mpp1, in PBMN cells from aged B6 mice (FIG. 10E). Because Compound-1 and Compound-1F retarded symptoms of aging (i.e. the decline in fertility) in non-transgenic B6 mice (cf. FIG. 7,8), the data presented herein demonstrate that (i) MPP1/Mpp1 is an aging marker in human and mouse PBMN cells, (ii) MPP1 induces a phenotype of premature senescence in vivo, and (iii) treatment with two different anti-aging drug candidates decreases the protein content of Mpp1 in PBMN cells of B6 mice and retards symptoms of aging.

Quantitative determination of Compound-1, Compound-1F in dog serum by HPLC. The oral bioavailability of Compound-1 and Compound-1F was investigated in dogs (German shepherd dogs) as a second animal model. The serum concentration of Compound-1 and Compound-1F was determined by HPLC. The calibration curve showed a linear relationship between increasing concentrations of Compound-1 and Compound-1F and the absorbance at 280 nm (FIG. 11A-C). The retention time of Compound-1 and Compound-1F was 5.43 min (FIG. 11C). The limit of detection for Compound-1F is below <2 ng when injected in a volume of 10 μl, which is equivalent to the concentration of 200 ng/ml (FIG. 11C).

Measurement of serum concentration shows that Compound-1 and Compound-1F have good oral bioavailability in dogs after oral treatment. The dog serum concentration was measured after oral gavage of Compound-1 and Compound-1F. There was a time-dependent linear increase in the dog serum concentration of Compound-1 after oral gavage (at t=0) of a single dose of 60 mg and 200 mg (FIG. 12A). The peak serum concentration was reached after 4 h after a single dose of 60 mg, and after 6 h after a single dose of 200 mg (FIG. 12A). The peak serum concentration of Compound-1 after a single dose of 60 mg was 2 microg/ml (FIG. 12A). The increase in the serum concentration of Compound-1 between male and female dogs was comparable (FIG. 12A). Also, the serum concentration was measured in dogs after repeated once daily oral dosing of Compound-1 and Compound-1F for 28 days. The serum concentration was measured at 24 h after the last dose. The steady-state serum concentrations of Compound-1 and Compound-1F were comparable (FIG. 12B). The steady-state serum concentration of Compound-1 and Compound-1F of dogs was compared with the serum concentration of mice. The data presented herein shows that by oral intake of Compound-1 and Compound-1F in mice (given in drinking water), the dose of 8 mg/kg/day in mice is roughly equivalent to a dose of 0.7 mg/kg day in dogs (FIG. 12B). This finding is in agreement with the equivalent surface area dosage rule, according to which mice usually require a 12-fold higher dose than dogs and humans. The concentration-time relationship of Compound-1 was determined and showed that there was a time-dependent increase in the serum concentration of Compound-1 after 28 days of repeated once daily dosing of Compound-1 at a daily dose of 20 mg/day, 60 mg/day and 200 mg/day (FIG. 12C). The peak concentration was reached after 4 h, and there was a dose-dependent increase in the peak serum concentration of Compound-1 (FIG. 12C).

Body-weight of male and female dogs is not changed by treatment with Compound-1 and Compound-1F for 28 days. Repeated oral dosing of Compound-1 and Compound-1F at a once daily dose of 20 mg/d, 60 mg/d, 120 mg/d and 200 mg/d for 28 days did not significantly change body weight in male and female dogs (FIG. 14A,B).

Treatment with Compound-1 and Compound-1F for 28 days had no effect on blood pressure and heart rate of dogs. Oral treatment of German shepherd dogs for 28 days with Compound-1 and Compound-1F at a once daily dose of 60 mg/d, 120 mg/d and 200 mg/d did not significantly change systolic and diastolic blood pressure (FIG. 15A,B). Repeated oral dosing for 28 days of Compound-1 and Compound-1F also did not significantly affect heart rate of male and female German shepherd dogs (FIG. 15C).

ECG parameters of dogs are not changed by treatment with Compound-1 and Compound-1F for 28 days. Repeated once daily oral dosing of Compound-1 and Compound-1F also did not significantly change heart function parameters of dogs as determined by ECG measurement (FIG. 16A,B). Notably, the P-R interval, QRS interval and Q-T interval were not significantly different before and after oral treatment with Compound-1 and Compound-1F for 28 days at a once daily dose of 60 mg, 120 mg and 200 mg (FIG. 16A,B).

Major hematologic parameters of dogs are not altered by treatment with Compound-1 and Compound-1F for 28 days. Blood analysis shows that major hematologic parameters were not changed by treatment with Compound-1 and Compound-1F for 28 days. i.e. hemoglobin (Hb), hematocrit (HCT), number of red blood cells (RBCs), mean corpuscular volume (MCV) and mean corpuscular hemoglobin concentration (MCHC) were not significantly different before and after oral treatment with Compound-1 (left panels) and Compound-1F (right panels) for 28 days at a once daily dose of 60 mg, 120 mg and 200 mg (FIG. 17).

Treatment of dogs with Compound-1 and Compound-1F does not significantly alter white blood cell number. The leukogram showed no significant differences before and after treatment of dogs with Compound-1 and Compound-1F for 28 days (FIG. 18). Notably, the total number of white blood cells was not altered by oral treatment with Compound-1 (left panels) and Compound-1F (right panels) for 28 days at a once daily dose of 60 mg, 120 mg and 200 mg (FIG. 18).

Biochemical parameters of liver and kidney function are not changed in dogs after treatment with Compound-1 and Compound-1F for 28 days. Treatment with Compound-1 and Compound-1F for 28 days did not significantly alter blood levels of aspartate transaminase (AST), alanine transaminase (ALT), alkaline phosphatase (ALP), blood urea nitrogen (BUN) and fasting blood glucose. Clinical laboratory parameters of liver and kidney function were determined before and after oral treatment of dogs with Compound-1 and Compound-1F for 28 days at a once daily dose of 60 mg, 120 mg and 200 mg (FIG. 19). Taken together, there were no significant adverse effects on major cardiovascular, hematologic, liver and kidney function parameters by repeated once daily oral treatment of dogs with Compound-1 and Compound-1F for 28 days up to a daily dose of 200 mg. At the highest dose of 200 mg, the dogs showed sedation. After, cessation of drug intake, this side effect disappeared within 24 h. At a daily dose of 120 mg/d, there was no sedation. Therefore, it is concluded that the no-observed-adverse-effect-level (NOAEL) of Compound-1 and Compound-1F in dogs is ≤200 mg/day, if sedation is not a desired side effect.

Compound-4 shows oral bioavailability in dogs, and improves mood. The oral bioavailability of Compound-4 was analysed in dogs because Compound-4 also showed anti-aging and neuroprotective effects and prevented the hippocampal accumulation of aggregated amyloid-beta, neuronal loss and neurodegeneration-promoting tau hyperphosphorylation in aged Tg-2576 AD mice (cf. FIGS. 1-2). Compound-4 also counteracted the hippocampal formation of hyperphosphorylated PHF tau in rats subjected to CUMS and transgenic Tg-TauP301L mice as a model of tauopathy (cf. FIGS. 3-4). By repeated oral dosing, Compound-4 achieved a peak serum concentration of 0.56±0.10 microg/ml in dogs at a daily dose of 200 mg (FIG. 20A,B). The peak serum level was reached 2 h after drug intake (FIG. 20A,B). Thereafter, the serum concentration declined and was undetectable at t=8 h after intake (FIG. 20). The peak serum levels of Compound-4 at 2 h after drug intake showed a dose-dependent increase at doses of 120 mg, 200 mg and 300 mg (FIG. 20C). Clinical laboratory parameters were within the normal range after drug intake for 28 days at a daily dose of 120 mg, 200 mg and 300 mg per day. In addition, blood pressure and heart rate were not different before and after drug intake of Compound-4 for 28 days. As early as 3 days of repeated oral dosing, Compound-4 increased the alertness of the dogs at a daily dose of 120 mg, 200 mg and 300 mg per day. In addition, their appetite was increased as measured by the slightly increased daily food intake. This observation also was made in rats as early as one week after repeated once daily oral dosing of 50 mg/kg and 25 mg/kg. Together these observations indicate a mood-improving activity of Compound-4. Hence, the present invention encompasses the use of Compound-4 for treatment of symptoms of depression, psychoses and other psychiatric illnesses and for the treatment of psychiatric symptoms of anorexia, low appetite, muscle wasting. Taken together, three different representative compounds, i.e. Compound-1, Compound-1F and Compound-4 show good oral bioavailability in dogs as a second animal with an excellent tolerability and without detectable negative side effects in the therapeutic dose range.

Determination of serum concentration of healthy human research participants after single and repeated oral dosing of Compound-1F. In frame of a three-part, placebo-controlled, randomized phase-1 study, the serum concentration and clinical laboratory parameters of healthy human voluntary research participants were analysed before and after the oral intake of Compound-1F. There was a dose-dependent increase in the serum concentration of Compound-1F in all research participants (FIG. 21A,C). Compound-1F was absent in sera from the placebo-treated participants (FIG. 21A,B). Safety assessment showed no treatment related adverse effects. After repeated dosing with 60 mg/day of Compound-1F, HPLC measurement of serum concentration of Compound-1F showed a peak serum concentration at 6 h after drug intake (FIG. 21C,D). After repeated dosing, the peak serum concentration at t=6 h was 5.33±0.76 microg/ml (n=8), and the serum concentration at 24 h after intake of the last dose of Compound-1F was 1.47±0.33 microg/ml (FIG. 21C,D). This serum concentration is within the therapeutic range to exert anti-aging activity in mice.

Normal hematologic parameters, white blood cell count, and liver and kidney function parameters in healthy human research participants after repeated oral dosing of Compound-1F. The primary end-point of the study was safety and tolerability. Regarding the primary end-point, analysis of clinical laboratory parameters shows that major hematologic parameters were not changed by repeated oral dosing of Compound-1F at a once daily dose of 60 mg for 10 days (i.e. after 14 days of study). Notably, hemoglobin (Hb), hematocrit (HCT), mean corpuscular volume (MCV), mean corpuscular hemoglobin concentration (MCHC), and number of red blood cells (RBCs) were not significantly different before and after repeated oral treatment with Compound-1F at a once daily dose of 60 mg (FIG. 22A-E). In addition, the total number of white blood cells was not altered, and the percentage of neutrophils and lymphocytes was within the normal range after 14 days of repeated, once daily oral dosing of Compound-1F (FIG. 22F-H). Kidney function parameters, i.e. serum urea and serum creatinine concentration, and liver function parameters, i.e. AST, and ALT levels, were also within the normal range before and after repeated once daily dosing of Compound-1F at a dose of 60 mg/d (FIG. 22I-L). Safety assessment documented that clinical laboratory parameters, and cardiovascular examination data (blood pressure, heart rate) of all research participants (drug treatment group and placebo group) were within the normal range during the study and after completion of the study (observation period 4 weeks). Study participants in the treatment group of part-2 of the study reported the following beneficial effects: (i) better sexual performance and climax (n=3 males), (ii) better physical performance (n=3), (iii) better memory (n=3), and better physical well-being (n=5). The two participants in the placebo group did not report any beneficial effect.

Down-regulation of the senescence-promoting peripheral blood mononuclear cell marker, MPP1, after treatment of elderly human research participants with Compound-1F for 28 days. Safety assessment confirmed that all clinical laboratory findings were within the normal range before and after 28 days of once daily oral drug intake of 60 mg of Compound-1F. Safety assessment showed no drug-related adverse events. Quantitative evaluation of immunoblot data shows that treatment of elderly human research participants for 28 days with Compound-1F at a daily dose of 60 mg led to a significant decrease of the senescence marker protein, MPP1, in PBMN cells compared to the cellular MPP1 content before treatment (FIG. 23A). Concomitantly with down-regulation of the senescence marker protein, MPP1, elderly healthy research participants reported better memory (n=4), better physical performance and well-being (n=5), and better sexual performance and climax (n=3). The two participants in the placebo group of part-3 did not report any beneficial effect. As a control, the steady-state serum concentration of Compound-1F in the elderly research participants was 1.54±0.31 microg/ml, at 24 h after the last drug intake after 28 days of repeated oral drug dosing at a once daily dose of 60 mg (FIG. 23B). Taken together, treatment of elderly healthy human research participants for 28 days with a daily dose of 60 mg of Compound-1F is safe and significantly decreased the senescence marker MPP1 in peripheral blood mononuclear cells.

The invention claimed is:

1. A method for the treatment of a disease in a patient, the method comprising administering a therapeutically or prophylactically effective amount of a compound, wherein:

the compound has the chemical structure:

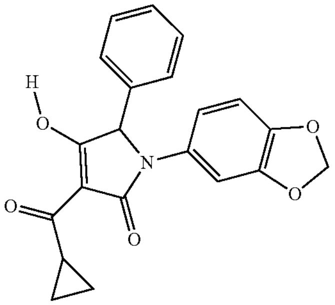 [SMILES: O=C(C1=C(O)C(c2ccccc2)N(c2ccc3c(c2)OCO3)C1=O)C1CC1]

(1-(1,3-benzodioxol-5-yl)-4-(cyclopropanecarbonyl)-3-hydroxy-2-phenyl-2H-pyrrol-5-one),

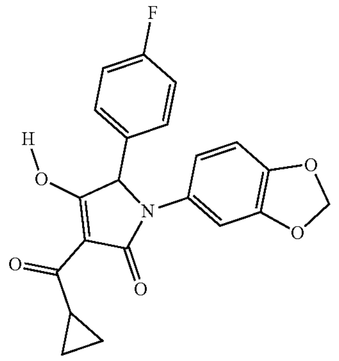 [SMILES: O=C(C1=C(O)C(c2ccc(F)cc2)N(c2ccc3c(c2)OCO3)C1=O)C1CC1]

(1-(1,3-Benzodioxol-5-yl)-4-(cyclopropanecarbonyl)-2-(4-fluorophenyl)-3-hydroxy-2H-pyrrol-5-one), or a pharmaceutically acceptable salt thereof; and the disease is selected from the group consisting of Alzheimer's disease, neurodegenerative symptoms of ageing, decline of male fertility, and decline of female fertility.

2. The method according to claim 1, wherein the compound has the chemical structure

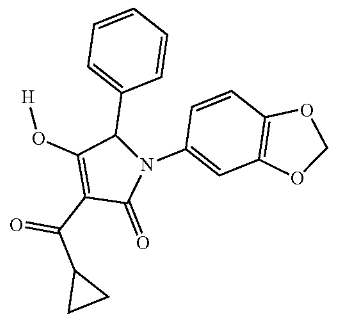 [SMILES: O=C(C1=C(O)C(c2ccccc2)N(c2ccc3c(c2)OCO3)C1=O)C1CC1]

(1-(1,3-benzodioxol-5-yl)-4-(cyclopropanecarbonyl)-3-hydroxy-2-phenyl-2H-pyrrol-5-one).

3. The method according to claim 1, wherein the compound inhibits at least one of (1) PHF (paired helical filament) Tau hyperphosphorylation, (2) phosphorylation of the serine/arginine-rich splicing factor 1 (SRSF1, ASF-1, SF2) by a kinase, formation and/or accumulation of A-beta peptides and A-beta plaques, (3) neurodegeneration, (4) neuronal loss, or (5) hippocampal neuronal loss.

4. The method according to claim 1, wherein the compound is comprised in a pharmaceutical composition comprising an excipient, a carrier, or both an excipient and a carrier.

5. The method according to claim 1, wherein the disease is selected from the group consisting of Alzheimer's disease, decline of male fertility, and decline of female fertility.

6. The method according to claim 1, wherein the treatment is selected from the group consisting of:

(i) therapeutic treatment of familial and sporadic forms of Alzheimer's Disease; and (ii) therapeutic treatment of low sperm quality and vitality, and low fertility in women.

7. The method according to claim 1, wherein the patient is a mammalian or human patient.

8. The method of claim 1, wherein the compound is:

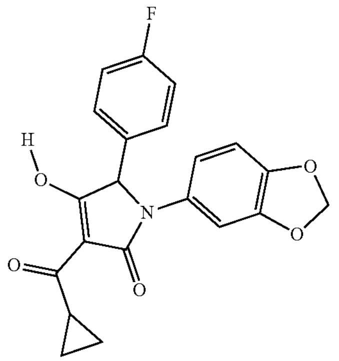 [SMILES: O=C(C1=C(O)C(c2ccc(F)cc2)N(c2ccc3c(c2)OCO3)C1=O)C1CC1]

(1-(1,3-Benzodioxol-5-yl)-4-(cyclopropanecarbonyl)-2-(4-fluorophenyl)-3-hydroxy-2H-pyrrol-5-one).

* * * * *